US006265609B1

(12) United States Patent
Jackson et al.

(10) Patent No.: US 6,265,609 B1

(45) Date of Patent: Jul. 24, 2001

(54) THIO-SUBSTITUTED PENTANEDIOIC ACID DERIVATIVES

(75) Inventors: Paul F. Jackson, Bel Air; Keith M. Maclin; Eric Wang, both of Baltimore; Barbara S. Slusher, Kingsville; Rena Lapidus, Baltimore, all of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/228,391

(22) Filed: Jan. 12, 1999

Related U.S. Application Data

(63) Continuation-in-part of application No. 09/110,186, filed on Jul. 6, 1998, now abandoned.

(51) Int. Cl.[7] .................................................... C07C 55/02

(52) U.S. Cl. .......................... 562/594; 562/489; 546/348; 564/162; 564/191; 564/192; 514/574; 514/277; 514/569; 514/570

(58) Field of Search .................................... 562/594, 489, 562/191; 514/574, 277, 569, 570; 546/348; 564/162, 192

(56) References Cited

U.S. PATENT DOCUMENTS

| | | |
|---|---|---|
| H1312 | 5/1994 | Coughlin et al. . |
| 4,151,172 | 4/1979 | Ondetti et al. . |
| 4,168,267 | 9/1979 | Petrillo, Jr. . |
| 4,316,896 | 2/1982 | Thorsett et al. . |
| 4,337,201 | 6/1982 | Petrillo, Jr. . |
| 4,374,131 | 2/1983 | Petrillo, Jr. . |
| 4,444,765 | 4/1984 | Karanewsky et al. . |
| 4,448,772 | 5/1984 | Karanewsky . |
| 4,452,790 | 6/1984 | Karanewsky et al. . |
| 4,452,791 | 6/1984 | Ryono et al. . |
| 4,468,519 | 8/1984 | Krapcho . |
| 4,547,324 | 10/1985 | Wong et al. . |
| 4,555,506 | 11/1985 | Karanewsky et al. . |
| 4,560,680 | 12/1985 | Ryono et al. . |
| 4,560,681 | 12/1985 | Karanewsky . |
| 4,567,166 | 1/1986 | Karanewsky et al. . |
| 4,616,005 | 10/1986 | Karanewsky et al. . |
| 4,671,958 | 6/1987 | Rodwell et al. . |
| 4,703,043 | 10/1987 | Karanewsky et al. . |
| 4,715,994 | 12/1987 | Parsons et al. . |
| 4,716,155 | 12/1987 | Karanewsky et al. . |
| 4,741,900 | 5/1988 | Alvarez et al. . |
| 4,849,525 | 7/1989 | Weller, III et al. . |
| 4,853,326 | 8/1989 | Quash et al. . |
| 4,867,973 | 9/1989 | Goers et al. . |
| 4,885,283 | 12/1989 | Broadhurst et al. . |
| 4,906,779 | 3/1990 | Weber et al. . |
| 4,918,064 | 4/1990 | Cordi et al. . |
| 4,927,966 | 5/1990 | Kalman . |
| 4,937,183 | 6/1990 | Ultee et al. . |
| 4,950,738 | 8/1990 | King et al. . |
| 4,959,493 | 9/1990 | Ohfume et al. . |
| 4,962,097 | 10/1990 | Parsons et al. . |
| 4,966,999 | 10/1990 | Coughlin et al. . |
| 4,988,681 | 1/1991 | Ishikawa et al. . |
| 4,994,446 | 2/1991 | Sokolovsky et al. . |
| 5,030,732 | 7/1991 | Morita et al. . |
| 5,041,644 | 8/1991 | Morita et al. . |
| 5,047,227 | 9/1991 | Rodwell et al. . |
| 5,061,806 | 10/1991 | Morita et al. . |
| 5,093,525 | 3/1992 | Weber et al. . |
| 5,099,063 | 3/1992 | Parsons et al. . |
| 5,136,080 | 8/1992 | Miller et al. . |
| 5,140,104 | 8/1992 | Coughlin et al. . |
| 5,143,908 | 9/1992 | Parsons et al. . |
| 5,145,990 | 9/1992 | Parsons et al. . |
| 5,147,867 | 9/1992 | Parsons et al. . |
| 5,156,840 | 10/1992 | Goers et al. . |
| 5,162,504 | 11/1992 | Horoszewicz . |
| 5,162,512 | 11/1992 | King et al. . |
| 5,190,976 | 3/1993 | Weber et al. . |
| 5,196,510 | 3/1993 | Rodwell et al. . |
| 5,242,915 | 9/1993 | Ueda et al. . |

(List continued on next page.)

FOREIGN PATENT DOCUMENTS

WO 96/26272 8/1996 (WO) .

OTHER PUBLICATIONS

Subasinghe, N. et al., "Synthesis of Acyclic and Dehydroaspartic Acid Analogues of Ac–Asp–Glu–OH and Their Inhibition of Rat Brain N–acetylated α–linked Acidic Dipeptidase (NAALA Dipeptidase)," *J. Med. Chem.*, 33, p. 2734–2744, (1990).

Slusher, B. et al., "Rat brain N–acetylated α–linked acidic dipeptidase activity," *The J. of Biological Chemistry*, vol. 265, No. 34, p. 21297–21301, (1990).

Tsai, G. et al., "Reductions in acidic amino acids and N–acetylaspartylglutamate in amyotrophic lateral sclerosis," *Brain Research*, 556, p. 151–161 (1991).

Meyerhoff, J. et al., "Genetically epilepsy–prone rats have increased brain regional activity of an enzyme which liberates glutamate from N–acetyl–aspartyl–glutamate," *Brain Research*, 593, p. 140–143 (1992).

Koenig, M. et al., "N–acetyl–aspartyl–glutamate (NAAG) elicits rapid increase in intraneuronal $Ca^{2+}$ in vitro," *NeuroReports*, 5, p. 1063–1068 (1994).

(List continued on next page.)

*Primary Examiner*—Johann Richter
*Assistant Examiner*—Rosalynd Keys
(74) *Attorney, Agent, or Firm*—Lyon & Lyon LLP

(57) ABSTRACT

The present invention relate to thio-substituted pentanedioic acid derivatives that inhibit N-Acetylated α-Linked Acidic Dipeptidase (NAALADase) enzyme activity, pharmaceutical compositions comprising the same, and methods of using the same to inhibit NAALADase enzyme activity, to effect neuronal activities, to inhibit angiogenesis, and to treat glutamate abnormalities, compulsive disorders and prostate diseases.

35 Claims, 36 Drawing Sheets

U.S. PATENT DOCUMENTS

| | | |
|---|---|---|
| 5,262,568 | 11/1993 | Weber et al. . |
| 5,326,856 | 7/1994 | Coughlin et al. . |
| 5,336,689 | 8/1994 | Weber et al. . |
| 5,449,761 | 9/1995 | Belinka, Jr. et al. . |
| 5,474,547 | 12/1995 | Aebischer et al. . |
| 5,489,525 | 2/1996 | Pastan . |
| 5,495,042 | 2/1996 | Belinka, Jr. et al. . |
| 5,500,420 | 3/1996 | Maiese . |
| 5,508,273 | 4/1996 | Beers et al. . |
| 5,527,885 | 6/1996 | Coughlin et al. . |
| 5,538,866 | 7/1996 | Israeli et al. . |
| 5,538,957 | 7/1996 | Tsaklakidis et al. . |
| 5,672,592 | 9/1997 | Jackson et al. . |
| 5,698,402 | 12/1997 | Luderer et al. . |
| 5,795,877 | 8/1998 | Jackson et al. . |

OTHER PUBLICATIONS

Vornov, J. et al., "Toxic NMDA–receptor activation occurs during recovery in a tissue culture model of ischemia," *J. of Neurochemistry*, 65, p. 1681–1691 (1995).

Carter, R. et al., "Prostate–specific membrane antigen is a hydrolase with substrate and pharmacologic characteristics of neuropeptidase," *Proc. Nat. Acad. Sci.*, 93, p. 749–753 (1996).

Anderson, B., et al., Anti–free Radical Mechanisms in Captopril Protection against Reperfusion Injury in Isolated Rat Hearts, Can. J. Cardiol., 1996, 12(10): 1099–1104.

Birincioglu, M., et al., Protective Effect of ACE Inhibitors on Ischemia–reperfusion–induced Arrhythmias in Rats: Is this Effect Related to the Free Radical Scavenging Action of These Drugs?, 1997, Free Rad. Res., 27 (4): 389–396.

Li, G.L., et al., Effects of Alpha–phenyl–n–tert–butyl Nitrone (PBN) on Compression Injury of Rat Spinal Cord, Free Rad. Res., 1997, 27: 187–196.

Krishan, P., et al., Effect of Angiotensin Converting Enzyme Inhibitors on Ischemia–reperfusion–induced Renal Injury in Rats, Pharmacological Research, 1998, 37 (1): 23–29.

Mizuno, A., et al., Inhibitory Effect of MCI–186, a Free Radical Scavenger, on Cerebral Artery Occlusion, Gen. Pharmac., 1998, 30 (4): 575–578.

La Penna, D., et al., Captopril has no significant Scavenging Antioxidant Activity in Human Plasma in vitro or in vivo, Brit. J. Clin. Pharmacol., 1996, 42:451–456.

Noda, Y., et al., Free Radical Scavenging Properties of Alacepril Metabolites and Lisinopril, Res. Comm. Mol. Path. Pharm., 1997, 96(2):125–136.

Packer, L., et al., Neuroprotection by the Metabolic Antioxidant Alpha–lipoic Acid, Free Radical Bio. Med., 1997, 22 (1/2):359–378.

de la Torre, J., et al., Reversal of Ischemic–induced Chronic Memory Dysfunction in Aging Rats with a Free Radical Scavenger–glycolytic Intermedicate Combination, Brain Research, 1998, 779:285–288.

Yamamoto, T., et al., Delayed Neuronal Death Prevented by Inhibition of Increased Hydroxyl Radical Formation in a Transient Cerebral Ischemia, Brain Research, 1997, 762:240–242.

Yuki, S. and Kogure, K., The Changes of LCGU and rCBF in the MCA Occlusion–Recirculation Model in Rats and the Ameliorating Effect of MCI–186, a Novel Free Radical Scavenger, Mol. Chem. Neuropathology, 1997, 32:123–128.

Stauch, B. et al., "The effects of N–acetylated alpha linked acidic dipeptidase (NAALADase) inhibitors on [$^3$H] NAAG catabolism in vivo," *Neuroscience Letters*, 100, p. 295–300 (1989).

Rothstein, J. et al., "Abnormal excitatory amino acid metabolism in amyotrophic lateral sclerosis," *Anals of Neurology*, vol. 28, p. 18–25 (1990).

Coyle, J. et al., "N–acetyl–aspartyl glutamate," *Excitatory Amino Acids*, p. 69–77 (1990).

Meyerhoff, J. et al., "Activity of a NAAG–hydrolyzing enzyme in brain may affect seizure susceptibility in genetically epilepsy–prone rats," *Molecular Neurobiology of Epilepsy*, p. 163–172 (1992).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315, p. 217–229 (1992).

Tsai, G. et al., "Immunocytochemical distribution of N–acetylaspartylglutamate in the rat forebrain and glutamergic pathways," *J. of Chem. Neuroanatomy*, 6, p. 277–292 (1993).

Tsai, G. et al., "Changes of excitatory neurotransmitter metabolism in schizophrenic brains," *Salmon Lecturer of the New York Academy of Medicine*, (Dec. 2–3, 1993).

Slusher, B. et al., "NAALADase: A Potential Regulator of Synaptic Glutamate," *Biotech Update DuPont NEN*, 9, p. 37–39 (1994).

Jackson, P. et al., "Design, synthesis, and biological activity of a potent inhibitor of the neuropeptidase N–acetylated α–linked acidic dipeptidase," *J. of Medicinal Chemistry*, (1995).

Woods, D. et al., "Gender–linked injury after focal cerebral ischemia," *Soc. For Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuroscience 1996 Abstract Form*, (1996).

Heston, W., "Bedeutung des prostataspezifischen Membranantigens (PSMA)," *Urologe*, 35, p. 400–407 (1996).

Barren III, R. et al., "Method for Identifying Prostate Cells in Semen Using Flow Cytometry," *The Prostate*, 36, p. 181–188 (1998).

Richard B. Silverman, The Organic Chemistry of Drug Design and Drug Action, pp. 15–22, 1992.*

* cited by examiner

COMPOUND 3 IS NEUROPROTECTIVE IN A CELL CULTURE MODEL OF STROKE

NAAG TOXICITY

COMPOUND 3 IS NEUROPROTECTIVE WHEN ADMINISTERED POST - ISCHEMIA

Compound 3 Enhances Myelination in Dorsal Root-Schwann Cell Co-Cultures

A - Control B - Ascorbic Acid (50 μg/ml) C - Ascorbic Acid (50 μg/ml) + Compound 3 (100nM)

Compound 2 Enhances Myelination in Dorsal Root-Schwann Cell Co-Cultures
FIG. 6A
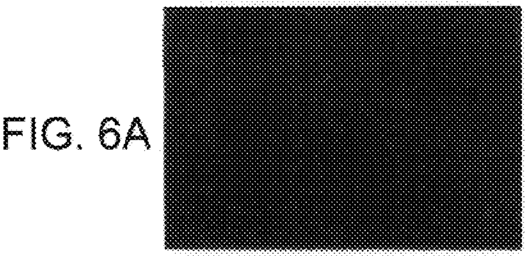
FIG. 6B
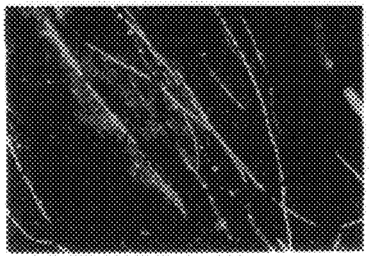
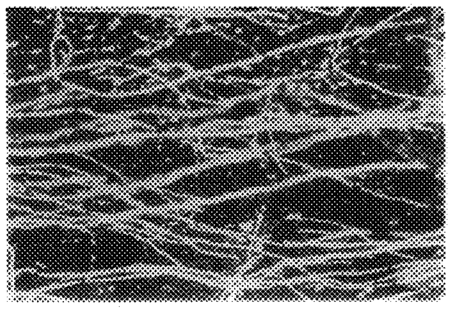
FIG. 6C
A - Control
B - Ascorbic Acid (50 μg/ml)
C - Ascorbic Acid (50 μg/ml) + Compound 2 (100nM)

STRIATUM

PARIETAL CORTEX

FRONTAL CORTEX

Extracellular Glutamate
(% baseline)

Compound 3 Administration Following Sciatic Nerve Crush

Vehicle Polymer

Compound 3 Polymer
2 ug drug / day

COMPOUND 3 PROTECTS AGAINST MPTP - TOXICITY IN CD1 MICE

COMPOUND 3 IS NEUROPROTECTIVE IN A DYNORPHIN - INDUCED SPINAL CORD INJURY MODEL

COMPOUND 3 IS NEUROPROTECTIVE IN A SPINAL CORD CULTURE MODEL OF ALS

COMPOUND 3 IS NEUROPROTECTIVE IN SPINAL CORD ORGANOTYPIC CULTURE MODEL OF ALS:
DOSE RESPONSE STUDY

Effect of 2-(phosphonomethyl) pentanedioic acid on LNCaP Human Prostate Xenografts Compound 3 Decreases the Growth of Rat Dunning Prostate Cancer Cell Xenografts GPI
mg/kg

0

3

30

Angiogenesis

Vehicle

Angiogenesis 1 ug/day

Angiogenesis 10 ug/day

Angiogenesis

100ug/day

FORMALIN PAIN TEST

+ STATISTICAL DIFFERENCE BETWEEN DRUG GROUP AND CONTROLS p<.02
‡ STATISTICAL DIFFERENCE BETWEEN DRUG GROUP AND CONTROLS p<.005

COMPOUND 1 VS. 0.6% ACETIC ACID INDUCED WRITHING

THIO-SUBSTITUTED PENTANEDIOIC ACID DERIVATIVES

This application is a continuation-in-part of U.S. patent application Ser. No. 09/110,186, filed Jul. 6, 1998 now abandoned.

BACKGROUND OF THE INVENTION

1. Field of the Invention

The present invention relates to thio-substituted pentanedioic acid derivatives that inhibit N-Acetylated α-Linked Acidic Dipeptidase (NAALADase) enzyme activity, pharmaceutical compositions comprising the same, and methods of using the same to inhibit NAALADase enzyme activity, to effect neuronal activities, to inhibit angiogenesis, and to treat glutamate abnormalities, compulsive disorders and prostate diseases.

2. Description of the Prior Art

Glutamate Abnormalities

Glutamate serves as the predominant excitatory neurotransmitter in the central nervous system (CNS). Neurons release glutamate in great quantities when they are deprived of oxygen, as may occur during an ischemic brain insult such as a stroke or a heart attack. This excess release of glutamate in turn causes over-stimulation (excitotoxicity) of N-methyl-D-aspartate (NMDA), AMPA, Kainate and MGR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause over-stimulation of the neurons. The over-stimulated neurons secrete more glutamate, creating a domino-effect which ultimately results in cell death via the production of proteases, lipases and free radicals.

Excessive activation of glutamate receptors has been implicated in various neurological diseases and conditions, including epilepsy, stroke, Alzheimer's disease, Parkinson's Disease, Amyotrophic Lateral Sclerosis (ALS), Huntington's Disease, schizophrenia, chronic pain, ischemia and neuronal loss following hypoxia, hypoglycemia, ischemia, trauma, and nervous insult. Recent studies have also advanced a glutamatergic basis for compulsive disorders, particularly drug dependence.

As an example, neurophysiological and pathological effects of ethanol have been found to be mediated through the glutamatergic system. Specifically, acute exposure to ethanol disrupts glutamatergic neurotransmission by inhibiting ion flow through channels in glutamate receptors, whereas chronic exposure up-regulates the number of glutamate receptors and thereby increases ion flow. Acute withdrawal from ethanol results in hyperexcitability and seizures in the presence of up-regulated channels, thereby making postsynaptic neurons vulnerable to excitotoxic damage.

Post mortem examinations of histologically normal brains from alcoholics have shown that chronic alcoholism moderately increases the density of the NMDA subtype of glutamate receptors in the frontal cortex. This up-regulation may represent a stage of ethanol-induced chronic neurotoxicity. As such, neurobiological effects of alcoholism, including intoxication, withdrawal seizures, delirium tremens, Wernicke-Korsakoff syndrome and fetal alcohol syndrome, can be understood as a spectrum of the consequences of ethanol's effect on the glutamatergic system. In this regard, alcoholism may be considered another member of the expanding family of glutamate-related neurological disorders.

The glutamatergic system has also been implicated in the behavioral effects of other abused drugs. For example, studies have shown that glutamatergic antagonists block motor-stimulating activities induced by amphetamine and cocaine, and glutamatergic agonists cause the same stereotypy as that produced by amphetamine. These results represent pharmacological evidence that the expression of the stereotypic effect of psychomotor stimulants involves the glutamatergic system.

Epidemiologic studies have revealed a strong correlation between drug dependence and other compulsive disorders. Additionally, a common genetic anomaly has been found among people with alcoholism, cocaine dependence, nicotine dependence, pathological gambling, attention deficit disorder (ADD), Tourette's syndrome, compulsive overeating and obesity. Such disorders are believed to be manifestations of the effects of excitotoxicity.

Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is currently no known effective treatment for glutamate abnormalities.

Prostate Cancer

Prostate cancer is the leading form of cancer and the second leading cause of death from cancer for men in the United States. The American Cancer Society has estimated that in 1996 alone, 317,100 new cases of prostate cancer were diagnosed and 41,400 deaths were caused by prostate cancer. The incidence rate of prostate cancer increased 65% between 1980 and 1990, and will continue to rise with improved screening tests and longer life expectancies. While most men used to die of other illnesses before prostate cancer had a chance to develop, higher prostate cancer mortality rates are expected as men live longer and the disease has more time to progress.

In 1993, the molecular cloning of Prostate Specific Membrane Antigen (PSMA) was reported as a potential prostate carcinoma marker and hypothesized to serve as a target for imaging and cytotoxic treatment modalities for prostate cancer. PSMA antibodies, particularly indium-111 labelled and itrium labelled PSMA antibodies, have been described and examined clinically for the diagnosis and treatment of prostate cancer. PSMA is expressed in prostatic ductal epithelium and is present in seminal plasma, prostatic fluid and urine. In 1996, it was found that the expression of PSMA cDNA confers the activity of NAALADase.

Angiogenesis

The term "angiogenesis" describes the process whereby new capillaries are formed. Angiogenesis is essential for normal physiological processes, such as growth, fertility and soft tissue wound healing. However, a significant percentage of all diseases are also dependent upon angiogenesis.

Cancer, for example, is an angiogenesis-dependent disease. Cancer tumor cells secrete or release angiogenic substances that activate nearby endothelial cells. These endothelial cells respond by expressing a cell autonomous pattern of behavior that culminates in the formation of new blood vessels. Research during the last three decades has demonstrated that angiogenesis is necessary to sustain the growth, invasion and metastasis of cancer tumors.

In addition to cancer, ailments such as rheumatoid arthritis, cardiovascular disease, neovascular diseases of the eye, peripheral vascular disorders, and dermatologic ulcers are dependent upon angiogenesis.

Research has shown that inhibiting angiogenesis offers a treatment that is complementary to, or an alternative to, traditional anti-angiogenic treatment options, such as surgical, chemo- and radiation therapies.

NAALADase Inhibitors

NAAG and NAALADase have been implicated in several human and animal pathological conditions. For example, it has been demonstrated that intra-hippocampal injections of NAAG elicit prolonged seizure activity. More recently, it was reported that rats genetically prone to epileptic seizures have a persistent increase in their basal level of NAALADase activity. These observations support the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors may be clinically useful in curbing the progression of ALS if increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

The findings described above suggest that NAALADase inhibitors could be useful in treating glutamate abnormalities. In fact, the results of studies conducted by the inventors confirm that NAALADase inhibitors are effective in treating glutamate abnormalities (particularly stroke, Parkinson's Disease, Amyotrophic Lateral Sclerosis (ALS), spinal cord injury, alcoholism and nicotine dependence), as well as prostate diseases (particularly prostate cancer).

While a few NAALADase inhibitors have been identified, they have only been used in non-clinical research. Examples of such inhibitors include general metallopeptidase inhibitors such as o-phenanthroline, metal chelators such as EGTA and EDTA, and peptide analogs such as quisqualic acid and β-NAAG. Accordingly, a need exists for new NAALADase inhibitors, as well as pharmaceutical compositions and methods using such new and known NAALADase inhibitors to treat glutamate abnormalities and prostate diseases.

SUMMARY OF THE INVENTION

The present invention relates to a compound of formula I

I

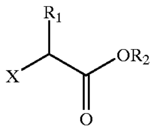

or a pharmaceutically acceptable salt, hydrate, metabolite, or prodrug thereof, wherein:

X is a moiety of formula II, III, or IV

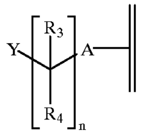

II

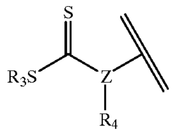

III

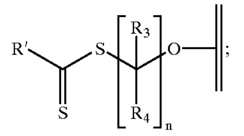

IV m and n are independently 0, 1, 2, 3 or 4;

Y is $SR_5$, $SO_3R_5$, $SO_2R_5$, $SOR_5$, $SO(NR_5)R_6$ or $S(N_2R_5R_6)R_7$;

Z is N or $CR_8$;

A is O, S, CR"R'" or $(CR"R'")_mS$;

R, R', R", R'", $R_1$, $R_2$, $R_3$, $R_4$, $R_5$, $R_6$, $R_7$ and $R_8$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl, or oxy, wherein said alkyl, alkenyl, cycloalkyl, cycloalkenyl and $Ar_1$ are independently unsubstituted or substituted with one or more substituent(s); and $Ar_1$ is a carbocyclic or heterocyclic moiety, which is unsubstituted or substituted with one or more substituent(s);

provided that when X is a moiety of formula II, $R_1$ is $(CH_2)_2COOR$ or $(CH_2)_2CONHR$, A is $CH_2$, n is 0, Y is $SR_5$, then $R_5$ is not hydrogen or COR; when X is a moiety of formula III, Z is N, and $R_1$ is $(CH_2)_2COOH$, then $R_4$ is not hydrogen; when X is a moiety of formula II and A is O, then n is 2, 3 or 4; when X is a moiety of formula II and A is S, then n is 2, 3 and 4; and when X is a moiety of formula II and A is $(CR"R'")_mS$, then n is 0, 2, 3 and 4.

The present invention also relates to a method of treating a glutamate abnormality in an animal, comprising administering to said animal an effective amount of a compound of formula I.

The present invention further relates to a method of inhibiting NAALADase activity in an animal, comprising administering to said animal an effective amount of a compound of formula I.

Additionally, the present invention relates to a method of effecting a neuronal activity in an animal, comprising administering to said animal an effective amount of a compound of formula I.

The present invention also relates to a method of treating a compulsive disorder, comprising administering to a patient in need thereof an effective amount of a compound of formula I.

The present invention further relates to a method of treating a prostate disease in an animal, comprising administering to said animal an effective amount of a compound of formula I.

Moreover, the present invention relates to a method of inhibiting angiogenesis in an animal, comprising administering to said animal an effective amount of a compound of formula I.

Finally, the present invention relates to a pharmaceutical composition comprising:

(i) an effective amount of a compound of formula I; and (ii) a pharmaceutically acceptable carrier.

BRIEF DESCRIPTION OF THE DRAWINGS

FIG. 6A is a microphotograph of an immunostained dorsal root ganglia-Schwann cell co-culture following treatment with progesterone.

FIG. 6B is a microphotograph of an immunostained dorsal root ganglia-Schwann cell co-culture following treatment with ascorbic acid.

FIG. 6C is a microphotograph of an immunostained dorsal root ganglia-Schwann cell co-culture following treatment with ascorbic acid and 2-[[(pentafluorobenzyl) hydroxyphosphinyl]methyl]pentanedioic acid.

DETAILED DESCRIPTION OF THE INVENTION

Definitions

Figure 1:
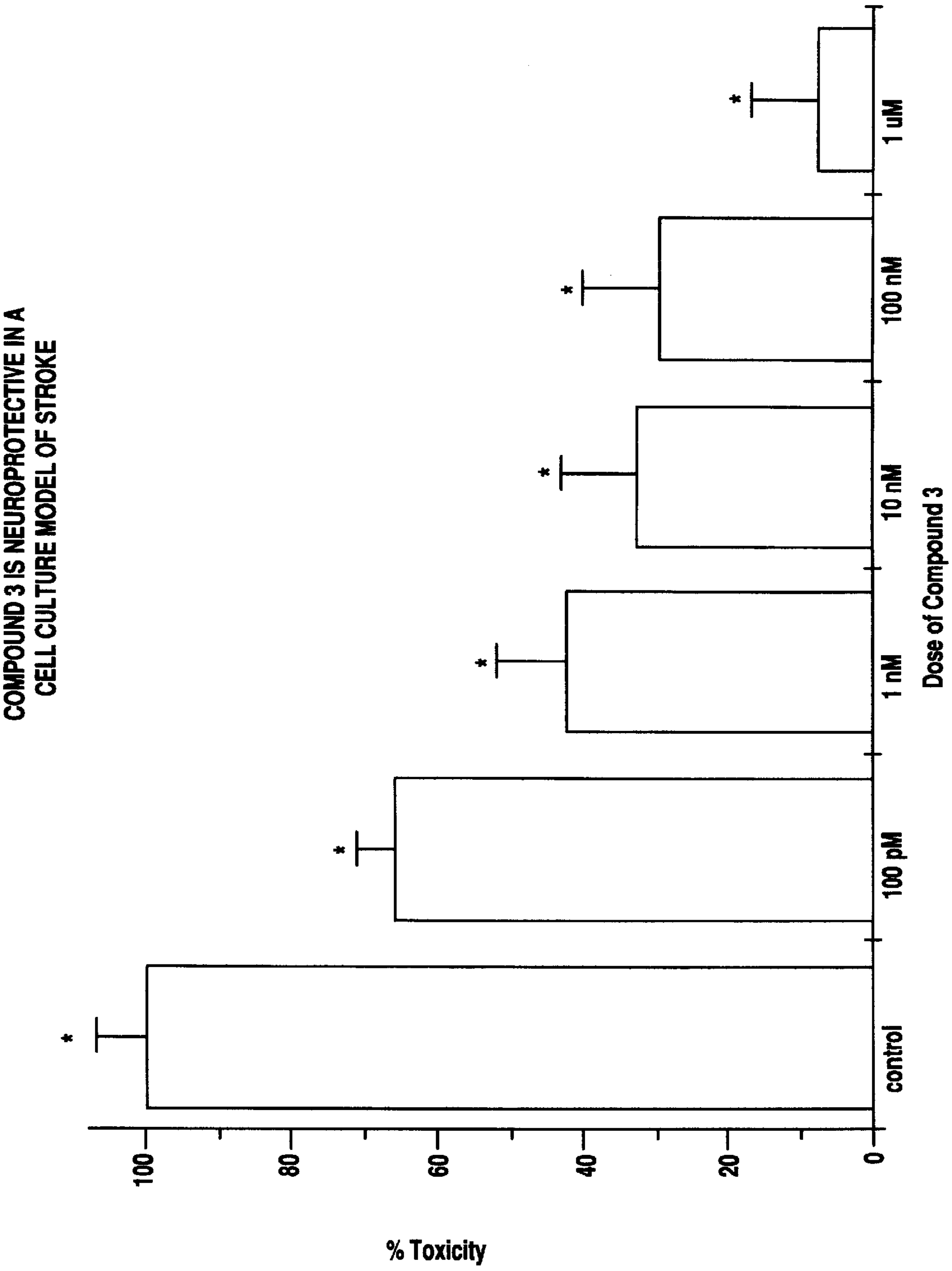
FIG. 1 is a bar graph plotting in vitro toxicity of ischemic insult (potassium cyanide and 2-deoxyglucose) against various doses of 2-(phosphonomethyl)pentanedioic acid with which cortical cell cultures were treated.

"Alkyl" refers to a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 6 carbon atoms.

"Attention Deficit Disorder" refers to a disorder characterized by developmentally inappropriate inattention and impulsivity, with or without hyperactivity. Inattention means a failure to finish tasks started, easy distractibility, seeming lack of attention, and difficulty concentrating on tasks requiring sustained attention. Impulsivity means acting before thinking, difficulty taking turns, problems organizing work, and constant shifting from one activity to another. Hyperactivity means difficulty staying seated and sitting still, and running or climbing excessively.

"Compound 1" refers to 2-(2-sulfanylethyl)pentanedioic acid.

"Compound 2" refers to 2-[[(pentafluorobenzyl) hydroxyphosphinyl]methyl]pentanedioic acid.

"Compound 3" refers to 2-(phosphonomethyl) pentanedioic acid.

"Compulsive disorder" refers to any disorder characterized by irresistible impulsive behavior. Examples of compulsive disorders include without limitation drug dependence, eating disorders, pathological gambling, ADD and Tourette's syndrome.

"Drug dependence" refers to a psychologic addiction or a physical tolerance to a drug. Tolerance means a need to increase the dose progressively in order to produce the effect originally achieved by smaller amounts.

"Eating disorder" refers to compulsive overeating, obesity or severe obesity. Obesity means body weight of 20% over standard height-weight tables. Severe obesity means over 100% overweight.

"Glutamate abnormality" refers to any disease, disorder or condition in which glutamate is implicated, including pathological conditions involving elevated levels of glutamate. Examples of glutamate abnormalities include epilepsy, stroke, Alzheimer's disease, Parkinson's Disease, Amyotrophic Lateral Sclerosis (ALS), Huntington's Disease, schizophrenia, acute pain, chronic pain, ischemia, neuronal insult and compulsive disorders.

"Glutamate modulator" refers to any composition of matter which alone or in combination with another agent affects the level of glutamate in an animal.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound which is required to cause a 50% inhibition of the target enzyme.

"Ischemia" refers to localized tissue anemia due to obstruction of the inflow of arterial blood. Global ischemia occurs when blood flow to the entire brain ceases for a period of time, such as may result from cardiac arrest. Focal ischemia occurs when a portion of the brain is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Isomers" refer to compounds having the same number and kind of atoms, and hence the same molecular weight, but differing in respect to the arrangement or configuration of the atoms. "Stereoisomers" are isomers that differ only in the arrangement of the atoms in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Metastasis" refers to "[t]he ability of cells of a cancer to disseminate and form new foci of growth at noncontiguous sites (i.e., to form metastases)." See Hill, R. P, Chapter 11, "Metastasis", pp. 178–195 in *The Basic Science of Oncology*, Tannock et al., Eds., McGraw-Hill, N.Y. (1992), herein incorporated by reference. "The transition from in situ tumor growth to metastatic disease is defined by the ability of tumor cells of the primary site to invade local tissues and to cross tissue barriers . . . To initiate the metastatic process, carcinoma cells must first penetrate the epithelial basement membrane and then invade the interstitial stroma . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* 71: 1368–1383 (1993), herein incorporated by reference.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate (NAA) and glutamate:

Catabolism of NAAG by NAALADase

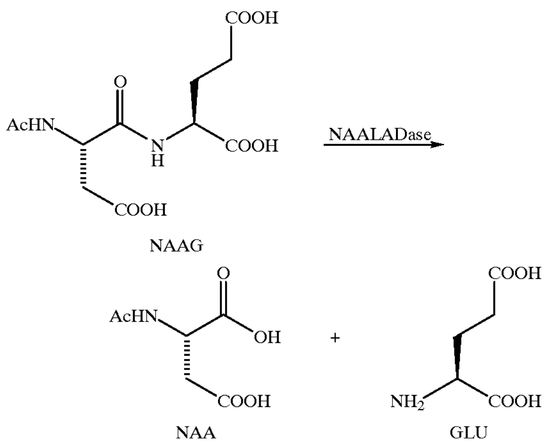

NAAG

NAA

GLU

NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Nervous function" refers to the various functions of the nervous system, which among other things provide an awareness of the internal and external environments of the body, make possible voluntary and reflex activities between the various structural elements of the organism, and balance the organism's response to environmental changes.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination process, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuroprotective" refers to the effect of reducing, arresting or ameliorating nervous insult, and protecting, resuscitating or reviving nervous tissue which has suffered nervous insult.

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995). For example, the inventive compounds can be transformed into prodrugs by converting one or more of the hydroxy or carboxy groups into esters.

"Radiosensitizer" refers to a low molecular weight compound administered to animals in therapeutically effective amounts to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention.

In relation to stroke, "therapeutic window of opportunity" or "window" refers to the maximal delay between the onset of ischemia and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

In relation to drug dependence, "treating" refers to suppressing the psychologic addiction or physical tolerance to the drug of abuse, and relieving or preventing a withdrawal syndrome resulting from the drug dependence.

"Withdrawal syndrome" refers to a disorder characterized by untoward physical changes that occur when the drug is discontinued or when its effect is counteracted by a specific antagonist.

COMPOUNDS OF THE PRESENT INVENTION

The present invention relates to a compound of formula I

I

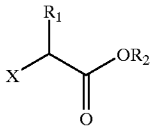

or a pharmaceutically acceptable salt, hydrate, metabolite, or prodrug thereof, wherein:

X is a moiety of formula II, III, or IV

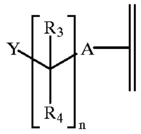

II

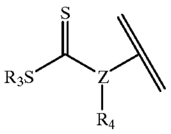

III

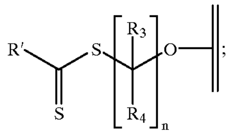

IV m and n are independently 0, 1, 2, 3 or 4;

Y is $SR_5$, $SO_3R_5$, $SO_2R_5$, $SOR_5$, $SO(NR_5)R_6$ or $S(N_2R_5R_6)R_7$;

Z is N or $CR_8$;

A is O, S, CR"R'" or $(CR"R'")_mS$;

R, R', R", R'", $R_1$, $R_2$, $R_3$, $R_4$, $R_5$, $R_6$, $R_7$ and $R_8$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl, or oxy, wherein said alkyl, alkenyl, cycloalkyl, cycloalkenyl and $Ar_1$ are independently unsubstituted or substituted with one or more substituent(s); and $Ar_1$ is a carbocyclic or heterocyclic moiety, which is unsubstituted or substituted with one or more substituent(s);

provided that when X is a moiety of formula II, $R_1$ is $(CH_2)_2COOR$ or $(CH_2)_2CONHR$, A is $CH_2$, n is 0, Y is $SR_5$, then $R_5$ is not hydrogen or COR; when X is a moiety of formula III, Z is N, and $R_1$ is $(CH_2)_2COOH$, then $R_4$ is not hydrogen; when X is a moiety of formula II and A is O, then n is 2, 3 or 4; when X is a moiety of formula II and A is S, then n is 2, 3 and 4; and when X is a moiety of formula II and A is $(CR''R''')_mS$, then n is 0, 2, 3 and 4.

Examples of useful alkyl groups include, without limitation, methyl, ethyl, propyl, isopropyl, butyl, tert-butyl, n-pentyl, 2-methyl pentyl and the like.

Possible substituents of said alkenyl, cycloalkyl, cycloalkenyl, and Ar, include, without limitation, $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment, $R_1$ is $—(CH_2)_2COO_9$; $R_9$ is hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_2$, wherein $R_9$ is unsubstituted or substituted with one or more substituent(s); and $Ar_2$ is a carbocyclic or heterocyclic moiety which is unsubstituted or substituted with one or more substituent(s).

In a more preferred embodiment, $R_1$ is $(CH_2)_2COOH$; and $R_2$ is hydrogen.

Preferred compounds of formula I wherein X is a moiety of formula II, A is CR''R''', n is 1, $R_1$ is $(CH_2)_2COOH$, and $R_2$ is hydrogen, include:

2-(2-sulfanylethyl)pentanedioic acid;
2-(2-sulfanylpropyl)pentanedioic acid;
2-(2-sulfanylbutyl)pentanedioic acid;
2-(2-sulfanylpentyl)pentanedioic acid;
2-(2-sulfanylhexyl)pentanedioic acid;
2-(2-phenyl-2-sulfanylethyl)pentanedioic acid;
2-(2-naphthyl-2-sulfanylethyl)pentanedioic acid;
2-(2-(4-pyridyl)-2-sulfanylethyl)pentanedioic acid;
2-(1-methyl-2-sulfanylethyl)pentanedioic acid;
2-(1-ethyl-2-sulfanylethyl)pentanedioic acid;
2-(1-benzyl-2-sulfanylethyl)pentanedioic acid;
2-(1-methyl-2-sulfanylpropyl)pentanedioic acid;
2-(1-ethyl-2-sulfanylpropyl)pentanedioic acid;
2-(1-propyl-2-sulfanylpropyl)pentanedioic acid;
2-(1-butyl-2-sulfanylpropyl)pentanedioic acid;
2-(2-sulfoethyl)pentanedioic acid;
2-[2-(methylsulfonyl)ethyl]pentanedioic acid;
2-[2-(ethylsulfonyl)ethyl]pentanedioic acid;
2-[2-(propylsulfonyl)ethyl]pentanedioic acid;
2-[2-(butylsulfonyl)ethyl]pentanedioic acid;
2-[2-(methylsulfanyl)-3-phenylpropyl]pentanedioic acid;
2-[2-(ethylsulfanyl)-3-phenylpropyl]pentanedioic acid;
2-[2-(propylsulfanyl)-3-phenylpropyl]pentanedioic acid;
2-[2-(butylsulfanyl)-3-phenylpropyl]pentanedioic acid;
2-[2-(methylsulfanyl)-3-(4-pyridyl)propyl]pentanedioic acid;
2-[2-(ethylsulfanyl)-3-(4-pyridyl)propyl]pentanedioic acid;
2-[2-(propylsulfanyl)-3-(4-pyridyl)propyl]pentanedioic acid;
2-[2-(butylsulfanyl)-3-(4-pyridyl)propyl]pentanedioic acid;
2-[1-benzyl-2-(methylsulfonyl)ethyl]pentanedioic acid;
2-[1-phenyl-2-(methylsulfonyl)ethyl]pentanedioic acid;
2-[1-(4-pyridyl)-2-(methylsulfonyl)ethyl]pentanedioic acid;
2-[1-benzyl-2-(ethylsulfonyl)ethyl]pentanedioic acid;
2-[1-phenyl-2-(ethylsulfonyl)ethyl]pentanedioic acid;
2-[1-(4-pyridyl)-2-(ethylsulfonyl)ethyl]pentanedioic acid;
2-(1-benzyl-2-sulfoethyl)pentanedioic acid;
2-(1-phenyl-2-sulfoethyl)pentanedioic acid;
2-(1-(4-pyridyl)-2-sulfoethyl)pentanedioic acid;
2-(1-methyl-2-sulfopropyl)pentanedioic acid;
2-(-ethyl-2-sulfopropyl)pentanedioic acid;
2-(1-propyl-2-sulfopropyl)pentanedioic acid;
2-(1-butyl-2-sulfopropyl)pentanedioic acid;
2-(1-benzyl-2-sulfobutyl)pentanedioic acid;
2-(1-phenyl-2-sulfobutyl)pentanedioic acid;
2-(1-(4-pyridyl)-2-sulfobutyl)pentanedioic acid;
2-[2-(methylsulfonyl)-1-phenylethyl]pentanedioic acid;
2-[2-(ethylsulfonyl)-1-phenylethyl]pentanedioic acid;
2-[2-(propylsulfonyl)-1-phenylethyl]pentanedioic acid;
2-[2-(butylsulfonyl)-1-phenylethyl]pentanedioic acid;
2-[2-(methylsulfonyl)-1-(4-pyridyl)ethyl]pentanedioic acid;
2-[2-(ethylsulfonyl)-1-(4-pyridyl)ethyl]pentanedioic acid;
2-[2-(propylsulfonyl)-1-(4-pyridyl)ethyl]pentanedioic acid;
2-[2-(butylsulfonyl)-1-(4-pyridyl)ethyl]pentanedioic acid;
2-[1-(sulfomethyl)propyl]pentanedioic acid;
2-[1-(sulfomethyl)butyl]pentanedioic acid;
2-(1-phenyl-2-sulfopropyl)pentanedioic acid;
2-(1-(4-pyridyl)-2-sulfopropyl)pentanedioic acid;
2-(1-phenyl-2-sulfobutyl)pentanedioic acid;
2-(1-(4-pyridyl)-2-sulfobutyl)pentanedioic acid; and
pharmaceutically acceptable salts, hydrates, metabolites, and prodrugs thereof.

The most preferred compounds of this embodiment are:

2-(2-sulfanylethyl)pentanedioic acid;
2-(2-sulfanylpropyl)pentanedioic acid;
2-(2-sulfanylbutyl)pentanedioic acid;
2-(2-sulfanylhexyl)pentanedioic acid;

2-(2-phenyl-2-sulfanylethyl)pentanedioic acid;

2-(2-(4-pyridyl)-2-sulfanylethyl)pentanedioic acid;

2-(1-methyl-2-sulfanylpropyl)pentanedioic acid;

2-(1-ethyl-2-sulfanylpropyl)pentanedioic acid;

2-(1-propyl-2-sulfanylpropyl)pentanedioic acid;

2-(1-butyl-2-sulfanylpropyl)pentanedioic acid;

2-(2-sulfoethyl)pentanedioic acid;

2-[2-(ethylsulfonyl)ethyl]pentanedioic acid; and pharmaceutically acceptable salts, hydrates, metabolites, and prodrugs thereof.

Preferred compounds of formula I, wherein X is a moiety of formula II, A is CR"R'", n is 0, Y is $SR_5$, $R_1$ is $(CH_2)_2COOH$, and $R_2$ is hydrogen, include:

2-(1-sulfanylethyl)pentanedioic acid;

2-(2-phenyl-1-sulfanylethyl)pentanedioic acid;

2-(2-phenyl-1-sulfanylpropyl)pentanedioic acid;

2-(2-phenyl-1-sulfanylbutyl)pentanedioic acid;

2-(2-(4-pyridyl)-1-sulfanylethyl)pentanedioic acid;

2-(2-(4-pyridyl)-1-sulfanylpropyl)pentanedioic acid;

2-[2-(4-pyridyl)-1-sulfanylbutyl]pentanedioic acid;

2-(2-methyl-1-sulfanylpropyl)pentanedioic acid;

2-(2-methyl-1-sulfanylbutyl)pentanedioic acid; and pharmaceutically acceptable salts, hydrates, metabolites, and prodrugs thereof.

The most preferred compounds of this embodiment are:

2-(1-sulfanylethyl)pentanedioic acid;

2-(2-phenyl-1-sulfanylethyl)pentanedioic acid;

2-(2-phenyl-1-sulfanylpropyl)pentanedioic acid;

2-(2-phenyl-1-sulfanylbutyl)pentanedioic acid;

2-[2-(4-pyridyl)-1-sulfanylbutyl]pentanedioic acid;

2-(2-methyl-1-sulfanylbutyl)pentanedioic acid; and pharmaceutically acceptable salts, hydrates, metabolites, and prodrugs thereof.

Preferred compounds of formula I, wherein X is a moiety of formula III, $R_1$ is $(CH_2)_2COOH$, $R_2$ is hydrogen, and Z is $CR_8$, include:

2-(dithiocarboxymethyl)pentanedioic acid;

2-(1-dithiocarboxyethyl)pentanedioic acid;

2-{[methylthio(thiocarbonyl)]methyl}pentanedioic acid;

2-{[ethylthio(thiocarbonyl)]methyl}pentanedioic acid;

2-{[propylthio(thiocarbonyl)]methyl}pentanedioic acid;

2-{[butylthio(thiocarbonyl)]methyl}pentanedioic acid;

2-(2-dithiocarboxy-1-phenylethyl)pentanedioic acid;

2-(2-dithiocarboxy-1-(4-pyridyl)ethyl)pentanedioic acid;

2-[dithiocarboxy(phenyl)methyl]pentanedioic acid;

2-[dithiocarboxy(4-pyridyl)methyl]pentanedioic acid; and pharmaceutically acceptable salts, hydrates, metabolites, and prodrugs thereof.

The most preferred compounds of this embodiment are:

2-(dithiocarboxymethyl)pentanedioic acid;

2-(1-dithiocarboxyethyl)pentanedioic acid; and pharmaceutically acceptable salts, hydrates, metabolites, and prodrugs thereof.

Preferred compounds of formula I, wherein X is a moiety of formula III, $R_1$ is $(CH_2)_2COOH$, $R_2$ is hydrogen, and Z is N, include:

2-[(methylsulfanylthiocarbonyl)amino]pentanedioic acid;

2-[(ethylsulfanylthiocarbonyl)amino]pentanedioic acid;

2-[(propylsulfanylthiocarbonyl)amino]pentanedioic acid;

2-[(butylsulfanylthiocarbonyl)amino]pentanedioic acid;

2-[(dithiocarboxy)amino]pentanedioic acid;

2-[(N-methyldithiocarboxy)amino]pentanedioic acid; and pharmaceutically acceptable salts, hydrates, metabolites, and prodrugs thereof.

The most preferred compounds of this embodiment are:

2-dithiocarboxyaminopentanedioic acid;

2-[(N-methyldithiocarboxy)amino]pentanedioic acid; and pharmaceutically acceptable salts, hydrates, metabolites, and prodrugs thereof.

Preferred compounds of formula I, wherein X is a moiety of formula II, A is O, n is 1, 2, 3 or 4, Y is $SR_5$, $R_1$ is $(CH_2)_2COOH$, and $R_2$ is hydrogen include:

2-(2-sulfanylethoxy)pentanedioic acid;

2-(2-sulfanylpropoxy)pentanedioic acid;

2-(2-sulfanylbutoxy)pentanedioic acid;

2-(2-sulfanyl-2-phenyl-1-ethoxy)pentanedioic acid;

2-(2-sulfanyl-2-phenyl-1-propoxy)pentanedioic acid;

2-(2-sulfanyl-2-phenyl-1-butoxy)pentanedioic acid;

2-(2-sulfanyl-2-(4-pyridyl)-1-ethoxy)pentanedioic acid;

2-(2-sulfanyl-2-(4-pyridyl)-1-propoxy)pentanedioic acid;

2-(2-sulfanyl-2-(4-pyridyl)-1-butoxy)pentanedioic acid;

2-(1-sulfanylethoxy)pentanedioic acid;

2-(1-sulfanylpropoxy)pentanedioic acid;

2-(1-sulfanylbutoxy)pentanedioic acid;

2-(1-sulfanyl-2-phenyl-1-ethoxy)pentanedioic acid;

2-(1-sulfanyl-2-phenyl-1-propoxy)pentanedioic acid;

2-(1-sulfanyl-2-phenyl-1-butoxy)pentanedioic acid;

2-(1-sulfanyl-2-(4-pyridyl)-1-ethoxy)pentanedioic acid;

2-(1-sulfanyl-2-(4-pyridyl)-1-propoxy)pentanedioic acid;

2-(1-sulfanyl-2-(4-pyridyl)-1-butoxy)pentanedioic acid; and pharmaceutically acceptable salts, hydrates, metabolites, and prodrugs thereof.

The most preferred compounds of this embodiment are:

2-(2-sulfanylethoxy)pentanedioic acid;

2-(2-sulfanylpropoxy)pentanedioic acid;

2-(2-sulfanylbutoxy)pentanedioic acid;

2-(2-sulfanyl-2-phenyl-1-propoxy)pentanedioic acid;

2-(1-sulfanylethoxy)pentanedioic acid;

2-(1-sulfanylpropoxy)pentanedioic acid;

2-(1-sulfanylbutoxy)pentanedioic acid;

2-(1-sulfanyl-2-phenyl-1-propoxy)pentanedioic acid; and pharmaceutically acceptable salts, hydrates, metabolites, and prodrugs thereof.

In another preferred embodiment, $R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein $R_1$ is unsubstituted or substituted with one or more substituent(s).

Preferred compounds of this embodiment include:

2-benzyl-4-sulfanylbutanoic acid;

2-benzyl-4-sulfanylpentanoic acid;

2-phenyl-4-sulfanylbutanoic acid;

2-phenyl-4-sulfanylpentanoic acid;

2-(4-pyridyl)-4-sulfanylbutanoic acid;

2-(4-pyridyl)-4-sulfanylpentanoic acid;

2-(3-pyridylmethyl)-4-sulfanylpentanoic acid;

2-(3-pyridylmethyl)-4-sulfanylhexanoic acid;

2-benzyl-3-sulfanylpropanoic acid;

2-benzyl-3-sulfanylbutanoic acid;

2-benzyl-3-sulfanylpentanoic acid;

2-phenyl-3-sulfanypropanoic acid;

2-phenyl-3-sulfanylbutanoic acid;

2-phenyl-3-sulfanylpentanoic acid;

2-(4-pyridyl)-3-sulfanylpropanoic acid;

2-(4-pyridyl)-3-sulfanylbutanoic acid;

2-(4-pyridyl)-3-sulfanylpentanoic acid;

2-(4-pyridylmethyl)-3-sulfanylpropanoic acid;

2-(4-pyridylmethyl)-3-sulfanylbutanoic acid;

2-(4-pyridylmethyl)-3-sulfanylpentanoic acid; and pharmaceutically acceptable salts, hydrates, metabolites, and prodrugs thereof.

The most preferred compounds of this embodiment are:

2-benzyl-4-sulfanylbutanoic acid;

2-benzyl-4-sulfanylpentanoic acid;

2-(3-pyridylmethyl)-4-sulfanylpentanoic acid;

2-(3-pyridylmethyl)-4-sulfanylhexanoic acid;

2-benzyl-3-sulfanylpropanoic acid;

2-benzyl-3-sulfanylpentanoic acid;

2-(4-pyridylmethyl)-3-sulfanylpentanoic acid; and pharmaceutically acceptable salts, hydrates, metabolites, and prodrugs thereof.

Preferred compounds of formula I, wherein X is a moiety of formula II, A is CR"R'", n is 2, 3 or 4, and Y is $SR_5$ include:

2-(3-sulfanylpropyl)pentanedioic acid;

2-(3-sulfanyl-2-methylpropyl)pentanedioic acid;

2-(3-sulfanyl-3-methylpropyl)pentanedioic acid;

2-(3-sulfanyl-3-phenylpropyl)pentanedioic acid;

2-[3-sulfanyl-2-(phenylmethyl)propylpentanedioic acid;

2-(4-sulfanylbutyl)pentanedioic acid;

2-[2-(sulfanylmethyl)butyl]pentanedioic acid;

2-(3-sulfanyl-4-phenylbutyl)pentanedioic acid;

2-[3-sulfanyl-4-(4-pyridinyl)butyl]pentanedioic acid;

2-(4-sulfanyl-2-methylbutyl)pentanedioic acid;

2-(4-sulfanyl-3-methylbutyl)pentanedioic acid;

2-(4-sulfanyl-4-methylbutyl)pentanedioic acid; and 2-(3-sulfanyloc tyl)pentanedioic acid.

The most preferred compounds of this embodiment include:

2-(3-sulfanylpropyl)pentanedioic acid;

2-(3-sulfanyl-2-methylpropyl)pentanedioic acid; and 2-(4-sulfanylbutyl)pentanedioic acid.

Preferred compounds of formula I, wherein X is a moiety of formula II, A is S, and n is 2, 3 or 4 include:

2-[(2-sulfanylethyl)thio]pentanedioic acid; and

2-[(2-sulfanyl-1-methylethyl)thio]pentanedioic acid.

Preferred compounds of formula I, wherein X is a moiety of formula II, A is (CR"R'")$_m$S, and n is 0, 2, 3 or 4 include:

2-[2-[(3,5-dicarboxypentyl)dithio]ethyl]pentanedioic acid;

2-[[(2-sulfanylethyl)thio]methyl]pentanedioic acid;

2-[[(3-sulfanylpropyl)thio]methyl]pentanedioic acid;

2-[[(2-sulfanyl-1-methylethyl)thio]methyl]pentanedioic acid;

2-[[(2-sulfanylpropyl)thio]methyl]pentanedioic acid;

2-[[(2-sulfanyl-2-phenylethyl)thio]methyl]pentanedioic acid; and

2-[[(2-sulfanyl-3-phenylpropyl)thio]methylpentanedioic acid.

The structures and names of representative compounds of formula I are set forth below.

| Structure | Name |
|---|---|
| 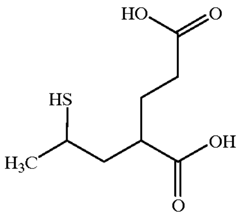 | 2-(2-sulfanylpropyl)-pentanedioic acid |
| 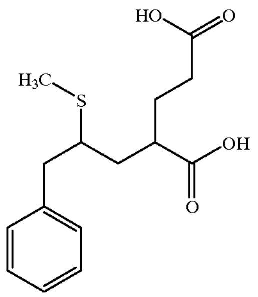 | 2-[2-(methylsulfanyl)-3-phenylpropyl]pentane-dioic acid |
| 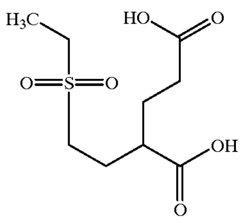 | 2-[2-(ethylsulfonyl)-ethyl]pentanedioic acid |
| 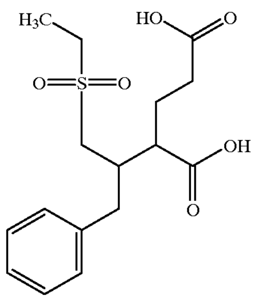 | 2-[1-benzyl-2-(ethylsulfonyl)ethyl]-pentanedioic acid |
| 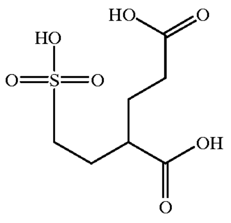 | 2-(2-sulfoethyl)-pentanedioic acid |

-continued

| Structure | Name |
|---|---|
| 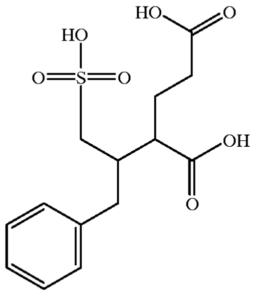 | 2-(1-benzyl-2-sulfoethyl)pentanedioic acid |
| 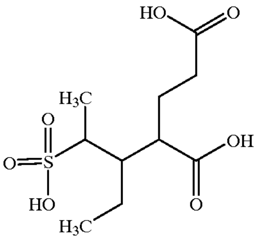 | 2-(1-ethyl-2-sulfopropyl)pentanedioic acid |
| 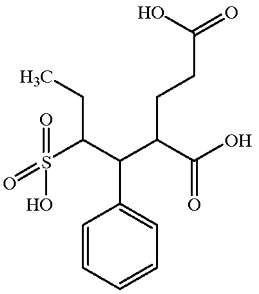 | 2-(1-phenyl-2-sulfobutyl)pentanedioic acid |
| 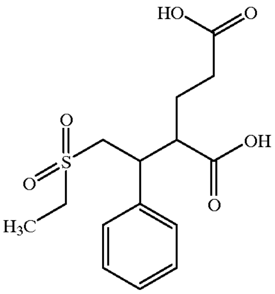 | 2-[2-(ethylsulfonyl)-1-phenylethyl]pentanedioic acid |
| 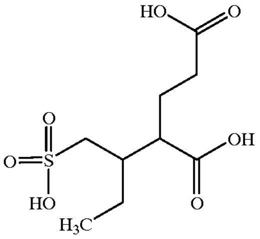 | 2-[1-(sulfomethyl)-propyl]pentanedioic acid |

-continued

| Structure | Name |
|---|---|
| 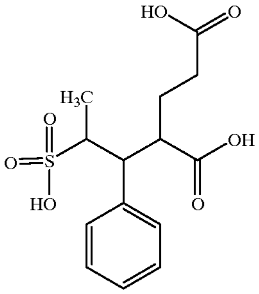 | 2-(1-phenyl-2-sulfopropyl)pentanedioic acid |
| 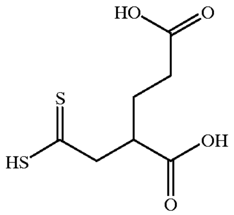 | 2-(dithiocarboxymethyl)-pentanedioic acid |
| 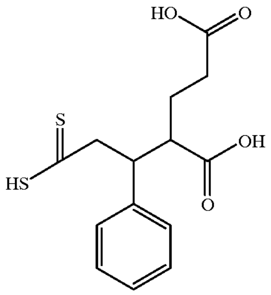 | 2-(2-dithiocarboxy-1-phenylethyl)pentanedioic acid |
| 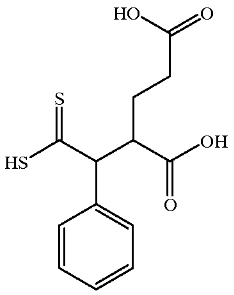 | 2-[dithiocarboxy-(phenyl)-methyl]pentane-dioic acid |
| 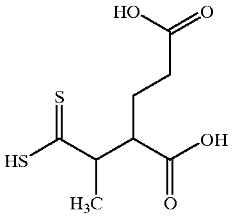 | 2-(1-dithiocarboxyethyl)-pentanedioic acid |

-continued

| Structure | Name |
| --- | --- |
| 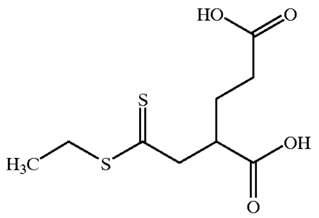 | 2-{[ethylthio-(thiocarbonyl)]methyl}-pentanedioic acid |
| 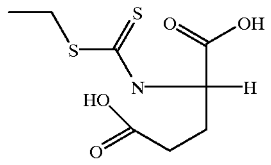 | 2-[(ethylsulfanylthio-carbonyl)amino]-pentanedioic acid |
| 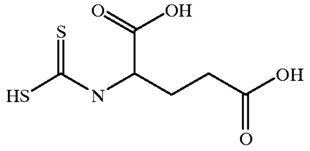 | 2-[(dithio-carboxy)amino]-pentanedioic acid |
| 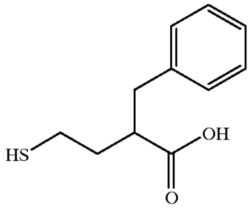 | 2-benzyl-4-sulfanyl-butanoic acid |
| 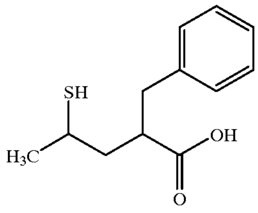 | 2-benzyl-4-sulfanylpentanoic acid |
| 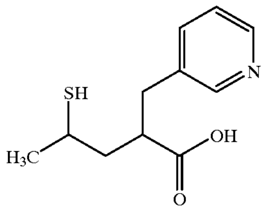 | 2-(3-pyridylmethyl)-4-sulfanylpentanoic acid |
| 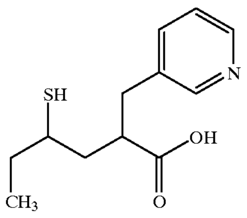 | 2-(3-pyridylmethyl)-4-sulfanylhexanoic acid |

-continued

| Structure | Name |
| --- | --- |
| 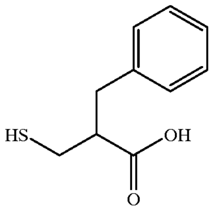 | 2-benzyl-3-sulfanyl-propanoic acid |
| 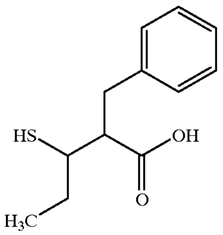 | 2-benzyl-3-sulfanylpentanoic acid |
| 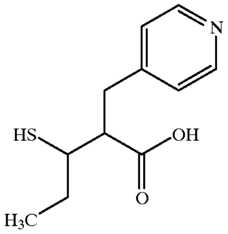 | 2-(4-pyridylmethyl)-3-sulfanylpentanoic acid |
| 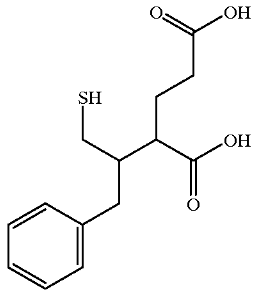 | 2-(1-benzyl-2-sulfanylethyl)-pentanedioic acid |
| 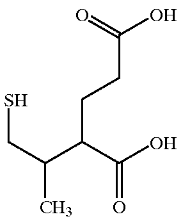 | 2-(1-methyl-2-sulfanylethyl)-pentanedioic acid |
| 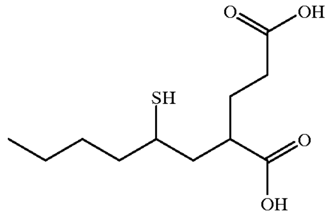 | 2-(2-sulfanylhexyl)-pentanedioic acid |

-continued

| Structure | Name |
|---|---|
| 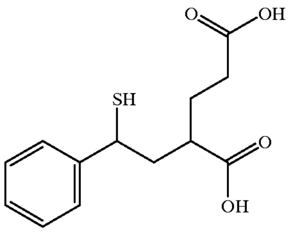 | 2-(2-phenyl-2-sulfanylethyl)-pentanedioic acid |
| 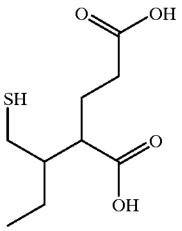 | 2-(1-ethyl-2-sulfanylethyl)-pentanedioic acid |
| 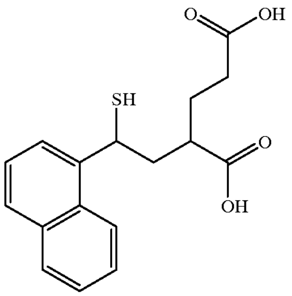 | 2-(2-naphthyl-2-sulfanylethyl)-pentanedioic acid |
| 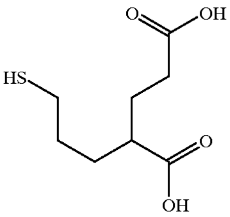 | 2-(3-sulfanylpropyl)-pentanedioic acid |
| 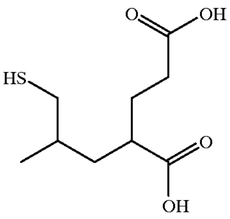 | 2-(3-sulfanyl-2-methylpropyl)-pentanedioic acid |
| 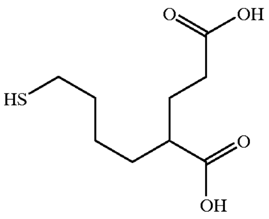 | 2-(4-sulfanylbutyl)-pentanedioic acid |

-continued

| Structure | Name |
|---|---|
| 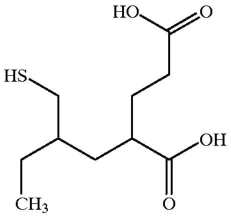 | 2-[2-(sulfanylmethyl)-butyl]pentanedioic acid |
| 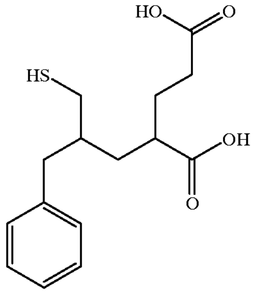 | 2-[3-sulfanyl-2-(phenylmethyl)propyl]-pentanedioic acid |
| 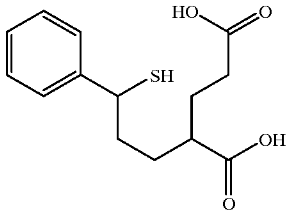 | 2-(3-sulfanyl-3-phenylpropyl)pentane-dioic acid |
| 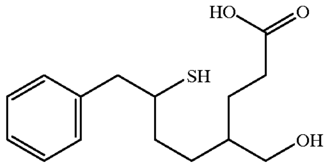 | 2-(3-sulfanyl-4-phenylbutyl)pentanedioic acid |
| 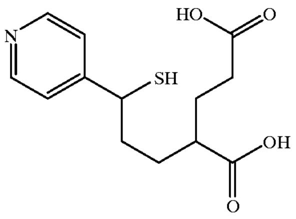 | 2-[3-sulfanyl-4-(4-pyridinyl)butyl]-pentanedioic acid |
| 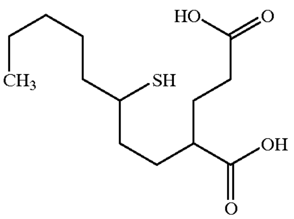 | 2-(3-sulfanyloctyl)-pentanedioic acid |

-continued

| Structure | Name |
|---|---|
| 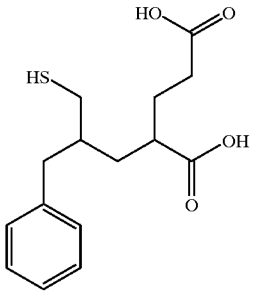 | 2-[3-sulfanyl-2-(phenylmethyl)propyl]-pentanedioic acid |
| 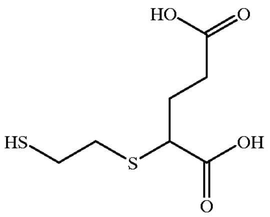 | 2-[(2-sulfanylethyl)-thio]pentanedioic acid |
| 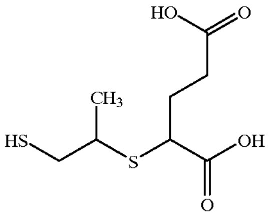 | 2-[(2-sulfanyl-1-methylethyl)thio]-pentanedioic acid |
| 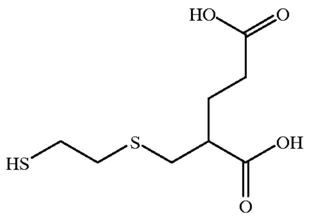 | 2-[[(2-sulfanylethyl)-thio]methyl]pentanedioic acid |
| 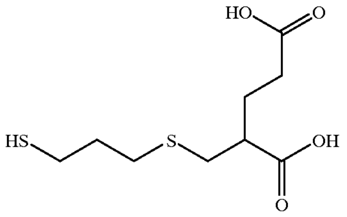 | 2-[[(3-sulfanylpropyl)-thio]methyl]pentanedioic acid |
| 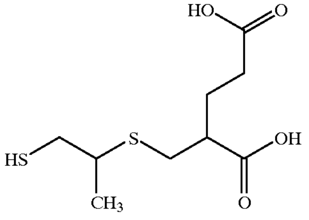 | 2-[[(2-sulfanyl-1-methyl-ethyl)thio]methyl]-pentanedioic acid |

-continued

| Structure | Name |
|---|---|
| 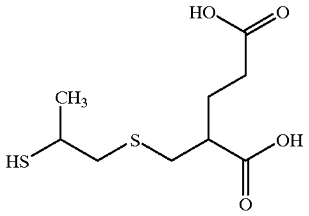 | 2-[[(2-sulfanylpropyl)-thio]methyl]pentanedioic acid |
| 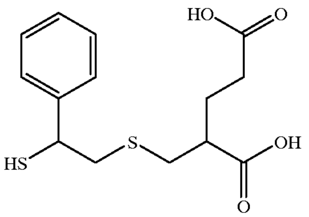 | 2-[[(2-sulfanyl-2-phenylethyl)thio]methyl-pentanedioic acid |
| 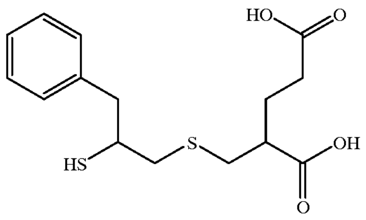 | 2-[[(2-sulfanyl-3-phenyl-propyl)thio]methyl] pentanedioic acid |
| 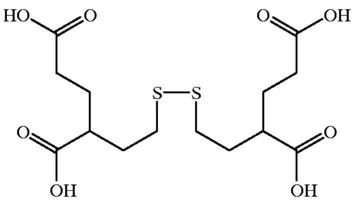 | 2-[2-[(3,5-dicarboxypentyl)dithio]-ethyl]pentanedioic acid |

The compounds of the present invention possess one or more asymmetric center(s) and thus can be produced as mixtures (racemic and non-racemic) of stereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of formula I. It is understood that the compounds of the present invention encompass optical isomers, individual stereoisomers as well as mixtures (racemic and non-racemic) of stereoisomers.

As discussed in greater detail below, the inventive compounds possess various pharmacological and pharmaceutical properties. In particular, the inventive compounds inhibit NAALADase enzyme activity. It is postulated that by inhibiting NAALADase enzyme activity, the inventive compounds regulate presynaptic release of glutamate which occurs during neurodegeneration.

The inventive compounds also protect against neurodegeneration in in vitro as well as in vivo animal models. Several inventive compounds have been demonstrated to be neuroprotective in tissue culture models of ischemia, when administered both pre- and post-ischemia. The inventive compounds provided significant neuroprotective effects when administered up to 60 minutes following ischemic damage in the in vitro model.

Moreover, the inventive compounds have been shown to afford significant protection in in vivo rat MCAO stroke model, and to be protective when administered at 60, 120, 180 and 360 minutes post-ischemia. Thus, the inventive compounds are effective for treating stroke in an animal when administered at least 60 minutes, at least 120 minutes, at least 180 minutes, and at least 360 minutes following the onset of stroke. One of ordinary skill in the art would expect such compounds to be equally, if not more, effective when administered within 60 minutes following onset of stroke. Likewise, compounds which are effective for treating stroke when administered at least 360 minutes following onset of stroke would be expected to embody compounds which are effective when administered at anytime beyond 360 minutes following onset of stroke. In addition to providing neuroprotection, it is possible that the inventive compounds are effective for treating stroke by providing behavioral functional recovery after stroke.

Synthesis of Compounds

The compounds of formula I wherein X is a moiety of formula II, and A is O or CR"R'" can be readily prepared by standard techniques of organic chemistry, utilizing the general synthetic pathways depicted below in Schemes I–X. Precursor compounds can be prepared by methods known in the art.

Scheme I

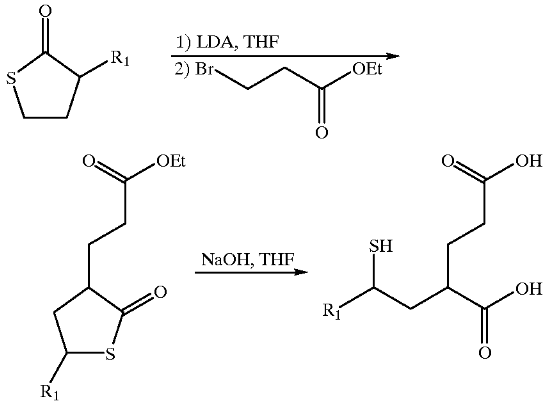

Scheme II

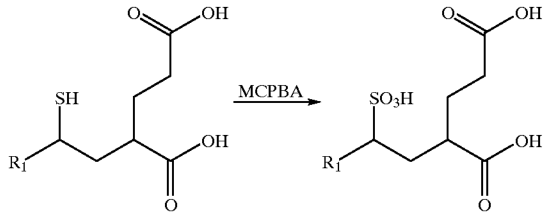

Scheme III

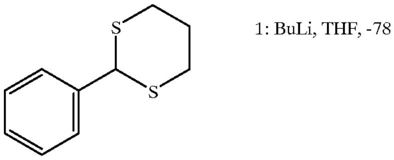

-continued

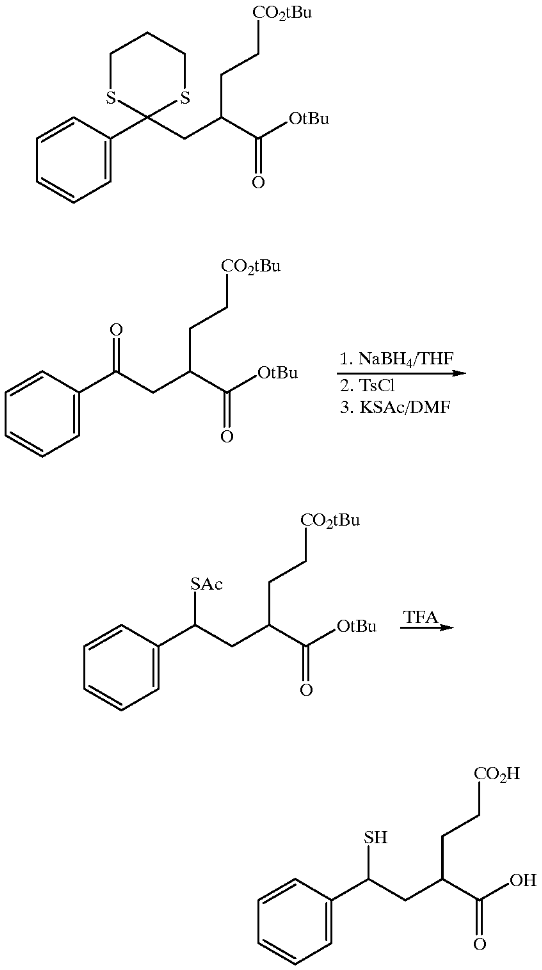

Scheme IV

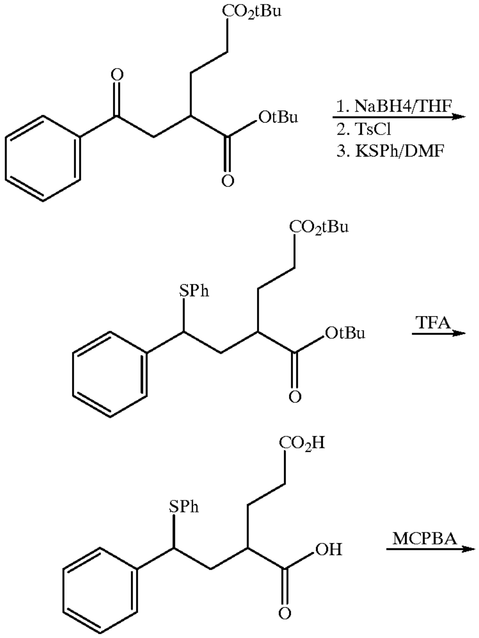

-continued
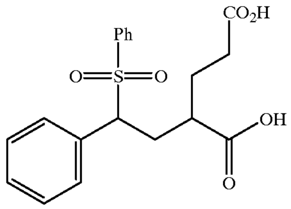
Scheme V
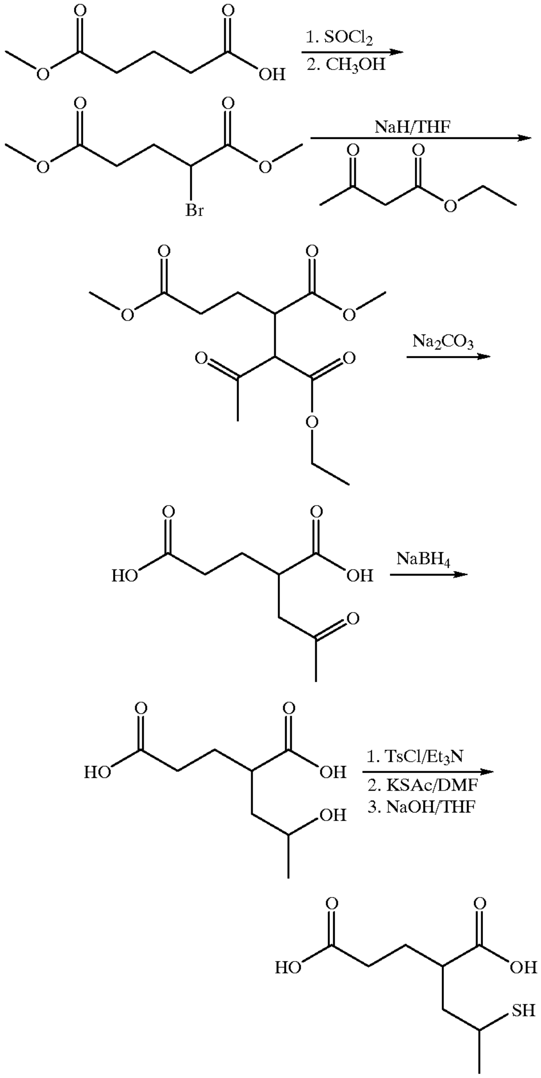
Scheme VI
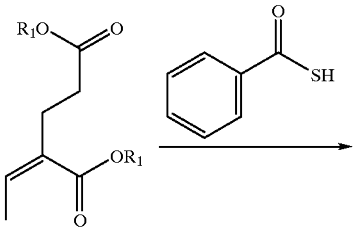
-continued
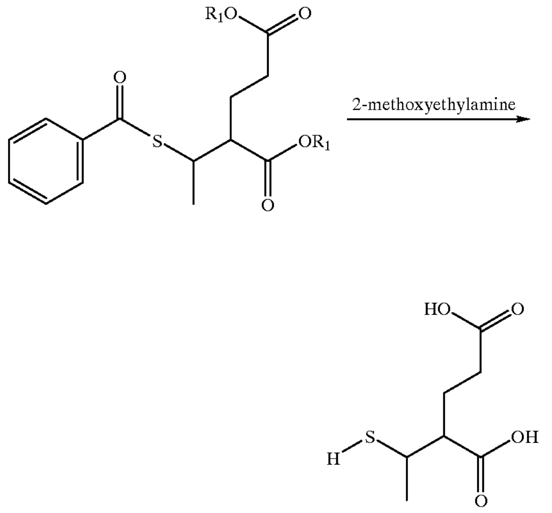
Scheme VII
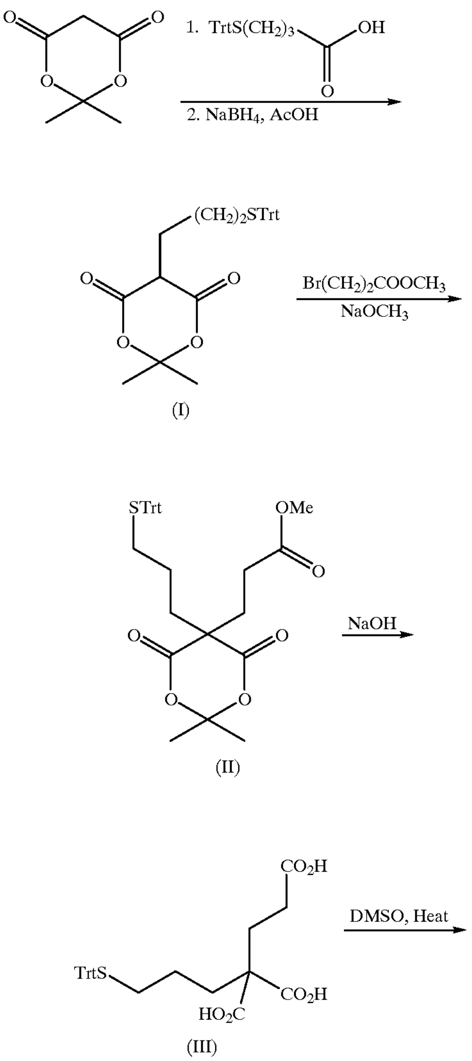
(I)
(II)
(III)

-continued

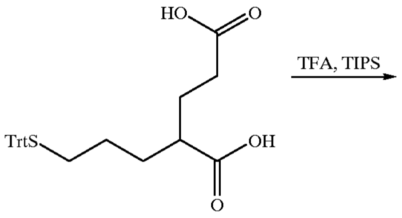

(IV)

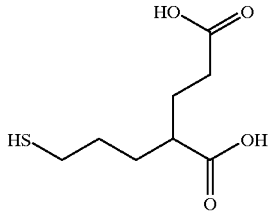

(V)

Scheme VIII

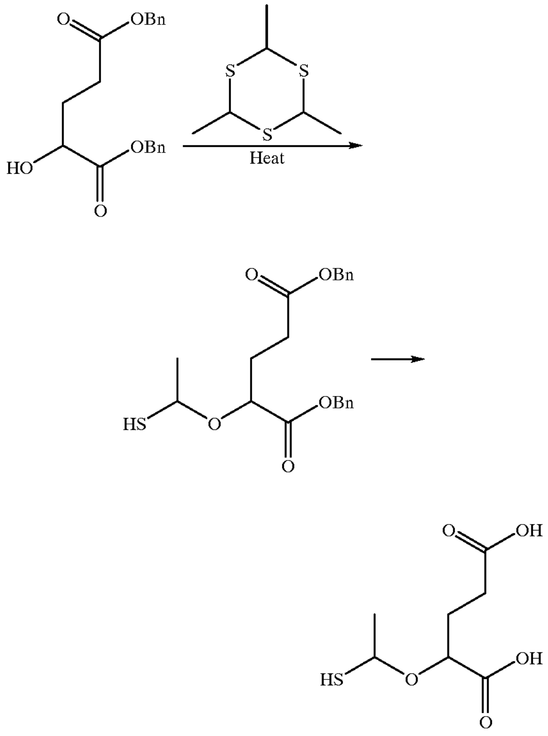

Scheme IX

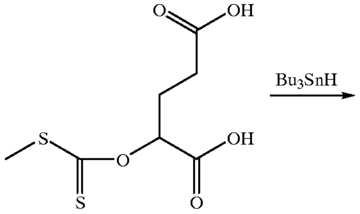

-continued

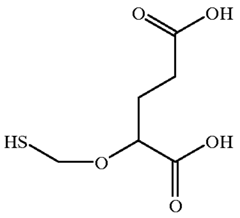

SCHEME X

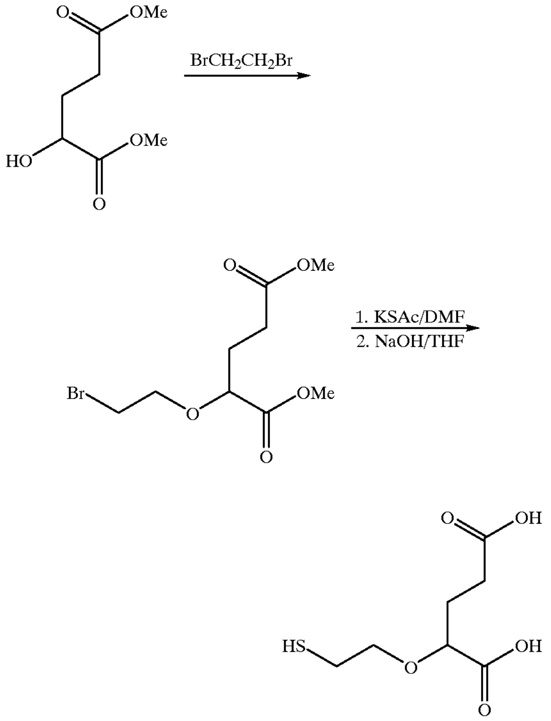

The compounds of formula I wherein X is a moiety of formula II and A is $(CR''R''')_mS$ can be readily prepared via standard synthetic methods such as oxidation of the corresponding thiol.

The compounds of formula I wherein X is a moiety of formula II and A is S can be readily prepared via standard synthetic techniques. For example, scheme X can be modified by starting with an appropriately substituted thio compound. In addition, compounds of this class can also be prepared by Michael addition of an appropriately substituted thiol derivative to an α-, β-unsaturated ester.

The compounds of formula I wherein X is a moiety of formula III can be readily prepared using standard synthetic pathways, such as reacting a glutamate derivative with carbon disulfide.

PHARMACEUTICAL COMPOSITIONS OF THE PRESENT INVENTION

The present invention also relates to a pharmaceutical composition comprising:

(i) an effective amount of a compound of formula I; and (ii) a pharmaceutically acceptable carrier.

Preferred compounds of formula I are set forth above.

In a preferred embodiment of the inventive pharmaceutical composition, the amount of the compound of formula I is effective for treating a glutamate abnormality in an animal.

In another preferred embodiment, the amount of the compound of formula I is effective for inhibiting NAALADase enzyme activity in an animal.

In a further preferred embodiment, the amount of the compound of formula I is effective for effecting a neuronal activity in an animal.

In an additional preferred embodiment, the amount of the compound of formula I is effective for treating a compulsive disorder in an animal.

In another preferred embodiment, the amount of the compound of formula I is effective for treating a prostate disease in an animal.

In a final preferred embodiment, the amount of the compound of formula I is effective for inhibiting angiogenesis in an animal.

METHODS OF THE PRESENT INVENTION

METHOD OF INHIBITING NAALADASE ENZYME ACTIVITY

Studies show that the compounds of formula I inhibit NAALADase enzyme activity.

Accordingly, the present invention further relates to a method of inhibiting NAALADase enzyme activity in an animal, comprising administering an effective amount of the compound of formula I to said animal.

METHOD OF TREATING GLUTAMATE ABNORMALITY

Although not limited to any one particular theory, it is believed that the compounds of the present invention modulate levels of glutamate by acting on a storage form of glutamate which is hypothesized to be upstream from the effects mediated by the NMDA receptor.

Accordingly, the present invention further relates to a method of treating a glutamate abnormality in an animal, comprising administering an effective amount of a compound of formula I to said animal.

The glutamate abnormality may be any disease, disorder or condition in which glutamate is implicated, including pathological conditions involving elevated levels of glutamate. Examples of glutamate abnormalities include without limitation epilepsy, stroke, Alzheimer's disease, Parkinson's Disease, Amyotrophic Lateral Sclerosis (ALS), Huntington's Disease, schizophrenia, acute pain, chronic pain, ischemia, peripheral neuropathy (including diabetic neuropathy), traumatic brain injury and physical damage to the spinal cord. In a preferred embodiment, the glutamate abnormality is selected from the group consisting of ischemia, stroke, Parkinson's Disease, Amyotrophic Lateral Sclerosis (ALS) and spinal cord injury.

Free radical scavengers have been postulated to be involved in various types of acute and chronic pathologic conditions in the brain and neural tissue. Recent research studies have revealed protective effects of these compounds in cerebral ischemia-reperfusion, excitotoxic amino acid brain injury, mitochondrial dysfunction, diabetes, diabetic neuropathy, inborn errors of metabolism, and other causes of acute or chronic damage to the brain or neural tissue. Krishan et al., *Pharmacological Research*, Vol. 37, No. 1, pp. 23–9 (January 1998); Noda et al., *Research Communications in Molecular Pathology and Pharmacology*, Vol. 96, No. 2, pp. 125–36 (May 1997); Anderson et al., *Canadian Journal of Cardiology*, Vol. 12, No. 10, pp. 1099–104 (October 1996); Mizuno et al., *General Pharmacology*, Vol. 30, No. 4, pp. 575–8 (April 1998); de la Torre et al., *Brain Research*, Vol. 779, Nos. 1–2, pp. 285–8 (January 1998); Yuki et al., *Molecular and Chemical Nueropathology*, Vol. 32, Nos. 1–3, pp. 123–8 (September–December 1997); Yamamoto et al., *Brain Research*, Vol. 762, Nos. 1–2, pp. 240–2 (Jul. 11, 1997). Since the compounds of the present invention contain a thiol moiety, it is hypothesized that the free radical scavenging properties of this functional group may contribute to the compounds' therapeutic efficacy. As such, the inventive compounds could be particularly effective in treating brain disorders involving free radical injury.

METHOD OF TREATING COMPULSIVE DISORDER

The inventors have unexpectedly found that the compounds of the present invention are effective in treating glutamate-related compulsive disorders.

Accordingly, the present invention also relates to a method of treating a compulsive disorder, comprising administering an effective amount of the compound of formula I to a patient in need thereof.

The compulsive disorder may be any disorder characterized by irresistible impulsive behavior. Examples of compulsive disorders treatable by the methods of the present invention include drug dependence, eating disorders, pathological gambling, ADD and Tourette's syndrome.

Preferably, the compulsive disorder is drug dependence. Commonly used drugs with potential for dependence include CNS depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

More preferably, the drug dependence is alcohol, nicotine, heroin or cocaine dependence.

METHOD OF EFFECTING NEURONAL ACTIVITY

The inventors have also discovered that inhibition of NAALADase promotes nerve regeneration and myelin formation.

Accordingly, the present invention further relates to a method of effecting a neuronal activity in an animal, comprising administering an effective amount of the compound of formula I to said animal.

The neuronal activity that is effected by the method of the present invention may be selected from the group consisting of: stimulation of damaged neurons, promotion of neuronal regeneration, prevention of neurodegeneration and treatment of a neurological disorder.

Examples of a neurological disorder that is treatable by the method of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; and Parkinson's disease.

The method of the present invention is particularly useful for treating a neurological disorder selected from the group consisting of: peripheral neuropathy caused by physical injury or disease state, traumatic brain injury, physical damage to the spinal cord, stroke associated with brain damage, demyelinating diseases and neurological disorders relating to neurodegeneration. Examples of demyelinating diseases include multiple sclerosis and peripheral demyelinating disease such as peripheral neuropathies and Charcot-Marie Tooth disease. Examples of neurological disorders relating to neurodegeneration include Alzheimer's Disease, Parkinson's Disease, and amyotrophic lateral sclerosis (ALS).

METHOD OF TREATING PROSTATE DISEASE

Additionally, the present invention relates to a method of treating a prostate disease in an animal, comprising administering an effective amount of the compound of formula I to said animal.

In a preferred embodiment, prostate disease is prostate cancer such as adenocarcinoma and metastatic cancers of the prostate, or a condition characterized by abnormal growth of prostatic epithelial cells such as benign prostatic hyperplasia.

METHOD OF TREATING CANCER

In addition to prostate cancer, other forms of cancer that may be treated with the compounds of the present invention include without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in treating cancer of tissues where NAALADase enzymes reside. Such tissues include the prostate as well as the brain, kidney and testis.

METHOD OF INHIBITING ANGIOGENESIS

The inventors have unexpectedly found that the compounds of the present invention are also effective in inhibiting angiogenesis.

Accordingly, the present invention further relates to a method of inhibiting angiogenesis in an animal, comprising administering to said animal an effective amount of a compound of formula I.

The angiogenesis to be inhibited may be necessary for fertility, necessary for metastasis of cancer tumors, or related to an angiogenic-dependent disease. Angiogenic-dependent diseases treatable by the methods of the present invention include without limitation rheumatoid arthritis, cardiovascular diseases, neovascular diseases of the eye, peripheral vascular disorders, and cancerous tumor growth, invasion, and metastasis.

ROUTE OF ADMINISTRATION

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, intracranial or intraosseous injection and infusion techniques. Invasive techniques are preferred, particularly direct administration to damaged neuronal tissue.

To be effective therapeutically as central nervous system targets, the compounds of the present invention should readily penetrate the blood-brain barrier when peripherally administered. Compounds which cannot penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

DOSAGE

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

In a preferred embodiment, the compounds are administered in lyophilized form. In this case, 1 to 100 mg of a compound of the present invention may be lyophilized in individual vials, together with a carrier and a buffer, such as mannitol and sodium phosphate. The compound may be reconstituted in the vials with bacteriostatic water before administration.

In treating global ischemia, the compounds of the present invention are preferably administered orally, rectally, parenterally or topically at least 1 to 6 times daily, and may follow an initial bolus dose of higher concentration.

The compounds of the present invention may be administered in combination with one or more therapeutic agents, including chemo-therapeutic agents. TABLE I provides known median dosages for selected chemotherapeutic agents. Specific dose levels for these agents and other therapeutic agents will depend upon considerations such as those identified above for the compounds of the present invention.

TABLE I

| CHEMOTHERAPEUTIC AGENT | MEDIAN DOSAGE |
|---|---|
| Aldesleukin | 22 million units |
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg–2 gm |
| Cyclophosphamide (non-lyophilized) | 100 mg–2 gm |
| Cytarabine (lyophilized powder) | 100 mg–2 gm |
| Dacarbazine | 100 mg–200 mg |
| Dactinomycin | 0.5 mg |
| Daunorubicin | 20 mg |
| Diethylstilbestrol | 250 mg |
| Doxorubicin | 10–150 mg |
| Epoetin Alfa | 2,000–10,000 units |
| Etidronate | 300 mg |
| Etoposide | 100 mg |
| Filgrastim | 300–480 mcgm |
| Floxuridine | 500 mg |
| Fludarabine Phosphate | 50 mg |
| Fluorouracil | 500 mg–5 gm |
| Goserelin | 3.6 mg |
| Granisetron Hydrochloride | 1 mg |
| Idarubicin | 5–10 mg |
| Ifosfamide | 1–3 gm |
| Immune Globulin | 500 mg–10 gm |
| Interferon Alpha-2a | 3–36 million units |
| Interferon Alpha-2b | 3–50 million units |
| Leucovorin Calcium | 50–350 mg |
| Leuprolide | 3.75–7.5 mg |
| Levamisole | 50 mg |
| Mechlorethamine | 10 mg |
| Medroxyprogesterone | 1 gm |
| Melphalan | 50 gm |
| Methotrexate | 20 mg–1 gm |
| Mitomycin | 5–40 mg |
| Mitoxantrone | 20–30 mg |
| Octreotide | 1,000–5,000 mcgm |
| Ondansetron Hydrochloride | 40 mg |
| Paclitaxel | 30 mg |
| Pamidronate Disodium | 30–*90 mg |
| Pegaspargase | 750 units |
| Plicamycin | 2,500 mcgm |
| Sargramostim | 250–500 mcgm |
| Streptozocin | 1 gm |
| Teniposide | 50 mg |
| Thiotepa | 15 mg |
| Vinblastine | 10 mg |
| Vincristine | 1–5 mg |

ADMINISTRATION REGIMEN

For the methods of the present invention, any administration regimen regulating the timing and sequence of drug delivery can be used and repeated as necessary to effect treatment. Such regimen may include pretreatment and/or co-administration with additional therapeutic agents.

To maximize protection of nervous tissue from nervous insult, the compounds should be administered to the affected cells as soon as possible. In situations where nervous insult is anticipated, the compounds should be administered before the expected nervous insult. Such situations of increased likelihood of nervous insult include surgery (cartoid endarterectomy, cardiac, vascular, aortic, orthopedic); endovascular procedures such as arterial catherization (cartoid, vertebral, aortic, cardia, renal, spinal, Adamkiewicz); injections of embolic agents; coils or balloons for hemostasis; interruptions of vascularity for treatment of brain lesions; and predisposing medical conditions such as crescendo transient ischemic attacks, emboli and sequential strokes. Where pretreatment for stroke or ischemia is impossible or impracticable, it is important to get the compounds to the affected cells as soon as possible during or after the event. In the time period between strokes, diagnosis and treatment procedures should be minimized to save the cells from further damage and death.

It is clear that both in animal models of stroke and in humans, the effect of cerebral ischemia are manifest on the cerebral metabolism rapidly, with a timescale measured in minutes or hours. Any form of potential neuroprotective treatment should therefore be given by the most rapidly effective route, which in practice means intravenously. The optimal duration and route of administration of treatment will depend on the individual pharmacokinetic properties of the neuroprotective compound, on the adverse-effect profile of the drug, and on the nature of the insult that gave rise to the stroke. Excitotoxic injury following stroke evolves over at least 4 hours in rodents and possibly beyond 48 hours in humans. Dyker et al., "Duration of Neuroprotective Treatment for Ischemic Stroke," Stroke, Vol. 29, pp. 535–542 (1998) Thus, it would be desirable to provide neuroprotection throughout this critical time period. Ideally, any compound for the treatment of stroke should adequately cross the blood-brain barrier and obtain sufficiently therapeutic levels within the brain and CSF.

For patients with prostate cancer that is neither advanced nor metastatic, the compounds of the present invention may be administered (i) prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic prostate cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

COMBINATION WITH OTHER TREATMENTS a. Nervous Insult

In methods of treating nervous insult (particularly acute ischemic stroke and global ischemia caused by drowning and head trauma), the compounds of the present invention can be co-administered with one or more therapeutic agents, preferably agents which can reduce the risk of stroke (such as aspirin), and more preferably agents which can reduce the risk of a second ischemic event (such as ticlopidine).

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

b. Angiogenesis-Dependent Disease

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

c. Cancer

Surgery and Radiation Treatment

In general, surgery and radiation treatment are employed as potentially curative therapies for patients with localized cancer who are under 70 years of age and are expected to live at least 10 more years.

If treated with surgery alone, however, many patients will experience recurrence of the cancer. Radiation treatment can also be problematic as the radiotherapeutic agents are toxic to normal tissues, and often create life-threatening side effects.

Use of the present invention in conjunction with surgery and radiation treatment could prevent remission and allow lower dosage levels of toxic radiotherapeutic agents. Based on the above statistics, there is considerable opportunity to use the present invention in conjunction with, or as an alternative to, surgery and/or radiation treatment.

Radiosensitizers

Radiosensitizers are known to increase the sensitivity of cancerous cells to the toxic effects of electromagnetic radiation. Several mechanisms for the mode of action of radiosensitizers have been suggested in the literature, including: hypoxic cell radiosensitizers (e.g., 2-nitroimidazole compounds and benzotriazine dioxide compounds) promote the reoxygenation of hypoxic tissue, and/or catalyze the generation of damaging oxygen radicals; non-hypoxic cell radiosensitizers (e.g., halogenated pyrimidines), which can be analogs of DNA bases, preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include without limitation: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) employs visible light as the electromagnetic radiation activator of the sensitizing agent. Examples of photodynamic electromagnetic radiosensitizers include without limitation: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

The compounds of the present invention may be administered in combination with electromagnetic radiosensitizers to increase the sensitivity of cancerous cells to the toxic effects of electromagnetic radiation. Use of the present invention in conjunction with electromagnetic radiosensitizers could prevent remission and allow lower dosage levels of electromagnetic radiation. Combining electromagnetic radiation with the compounds, compositions and methods of the present invention should be more effective than electromagnetic radiation alone in treating cancer.

When combined with electromagnetic radiosensitizers, the compounds of the present invention may also be administered in conjunction with one or more of the following compounds: compounds which promote the incorporation of radiosensitizers to the target cells; compounds which control the flow of therapeutics, nutrients and/or oxygen to the target cells; chemotherapeutic agents which act on the tumor with or without additional electromagnetic radiation; or other therapeutic agents for treating cancer or other diseases. Examples of such therapeutic agents include without limitation: 5-fluorouracil, leucovorin, 5'-amino-5'deoxythymidine, oxygen, carbogen, red cell transfusions, perfluorocarbons (e.g. Fluosol-DA), 2,3-DPG, BW12C, calcium channel blockers, pentoxyfylline, hydralazine, and L-BSO. Examples of chemotherapeutic agents are listed in TABLE I.

Hormonal Therapy

Hormonal ablation by medication and/or orchiectomy is used to block hormones that promote further growth and metastasis of cancer. With time, both the primary and metastatic tumors of virtually all of these patients become hormone-independent and resistant to therapy. Continuous supplementation with the compounds of the present invention may be used to prevent or reverse this potentially metastasis-permissive state.

Chemotherapy

Chemotherapy has been successful in treating some forms of cancer. However, in treating other forms of cancer, chemotherapy has been reserved only as a last resort. In any case, chemotherapy can be problematic as chemotherapeutic agents are toxic to normal tissues and often create life threatening side effects. Additionally, chemotherapy often has high failure and/or remission rates.

Use of the present invention in conjunction with chemotherapy could prevent remission and allow lower dosage levels of toxic chemotherapeutic agents. Combining chemotherapy with the methods of the present invention should be more effective than chemotherapy alone in treating cancer.

Immunotherapy

The compounds of the present invention may also be used in combination with monoclonal antibodies to treat cancer. The present invention may also be used with immunotherapies based on polyclonal or monoclonal antibody-derived reagents. These reagents are well known in the art, and include radiolabeled monoclonal antibodies such as monoclonal antibodies conjugated with strontium-89.

In Vivo Toxicity of NAALADase Inhibitors

To examine the toxicological effect of NAALADase inhibition in vivo, a group of mice were injected with 2-(phosphonomethyl)pentanedioic acid (Compound 3), a NAALADase inhibitor of high activity, in doses of 1, 5, 10, 30, 100, 300 and 500 mg/kg body weight. The mice were subsequently observed two times per day for 5 consecutive days. The survival rate at each dose level is provided below in TABLE II. The results show that the NAALADase inhibitor is non-toxic to mice, suggesting that it would be similarly non-toxic to humans when administered at therapeutically effective amounts.

TABLE II

TOXICOLOGICAL EFFECTS OF NAALADASE INHIBITORS

| Dose (mg/kg) | 1 | 5 | 10 | 30 | 100 | 300 | 500 |
|---|---|---|---|---|---|---|---|
| Survival Rate After 5 days (%) | 100 | 100 | 100 | 100 | 100 | 100 | 66.7 |

In Vitro Inhibition of NAALADase Activity

A compound of formula I was tested for in vitro inhibition of NAALADase activity. The results are provided below in TABLE III.

TABLE III

IN VITRO INHIBITION OF NAALADASE ACTIVITY

| Compound | $K_I$ (nM) |
|---|---|
| 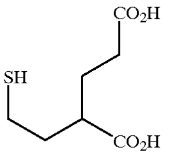 2-(2-sulfanylethyl)pentanedioic acid | 510 |
| 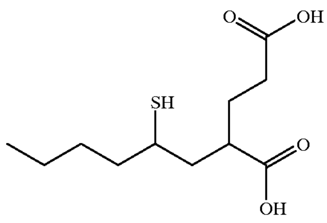 2-(2-sulfanylhexyl)pentanedioic acid | 4750 |
| 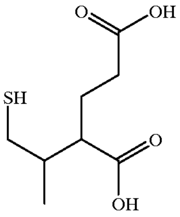 2-(1-methyl-2-sulfanylethyl)pentanedioic acid | 843 |
| 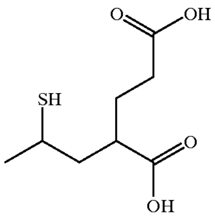 2-(2-sulfanylpropyl)pentanedioic acid | 158 |
| 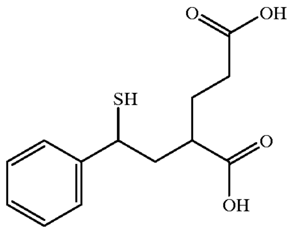 2-(2-phenyl-2-sulfanylethyl)petanedioic acid | 4650 |

TABLE III-continued

| IN VITRO INHIBITION OF NAALADASE ACTIVITY | |
|---|---|
| Compound | $K_I$ (nM) |
| 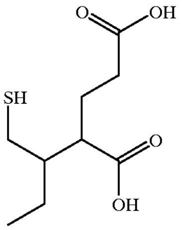 2-(1-ethyl-2-sulfanylethyl)pentanedioic acid | 1550 |
| 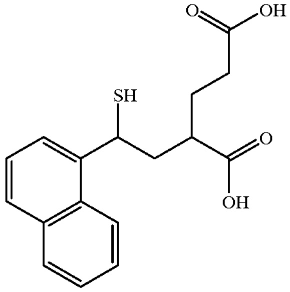 2-(2-naphthyl-2-sulfanylethyl)pentanedioic acid | 10000 |
| 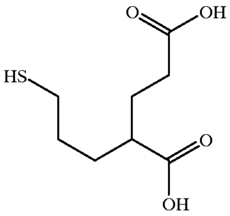 2-(3-sulfanylpropyl)pentanedioic acid | 100 |
| 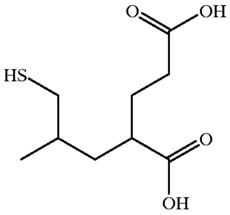 2-(3-sulfanyl-2-methylpropyl)pentanedioic acid | 239 |
| 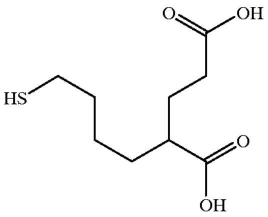 2-(4-sulfanylbutyl)pentanedioic acid | 1128 |

TABLE III-continued

| IN VITRO INHIBITION OF NAALADASE ACTIVITY | |
|---|---|
| Compound | $K_I$ (nM) |
| 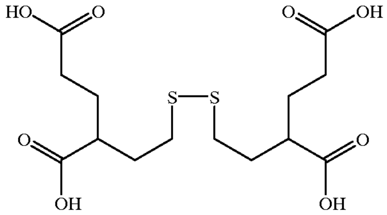 2-[2-[(3,5-dicarboxypentyl)dithio]ethyl]pentanedioic acid | 16500 |

Protocol for Assaying In Vitro Inhibition of NAALADase Activity

The amount of [$^3$H]Glu liberated from [$^3$H]NAAG in 50 mM Tris-Cl buffer was measured for 15 minutes at 37° C. using 30–50 μg of synaptosomal protein. Substrate and product were resolved by anion-exchange liquid chromatography. Duplicate assays were performed so that no more than 20% of the NAAG was digested, representing the linear range of peptidase activity. Quisqualate (100 μM) was included in parallel assay tubes to confirm the specificity of the measurements.

In Vitro Assay of NAALADase Inhibitors on Ischemia

To examine the in vitro effect of NAALADase inhibitors on ischemia, cortical cell cultures were treated with 2-(2-sulfanylethyl)pentanedioic acid during an ischemic insult (potassium cyanide and 2-deoxyglucose) and for one hour thereafter (for experimental details, see Vornov et al., *J. Neurochem.*, Vol. 65, No. 4, pp. 1681–1691 (1995)).

The neuroprotective effect of the tested compound is provided below in TABLE IV(a). Neuroprotective is effect is expressed as $EC_{50}$, the concentration which is required to cause a 50% reduction in glutamate toxicity following an ischemic insult.

TABLE IV(a)

| Compound | $EC_{50}$ (nM) |
|---|---|
| 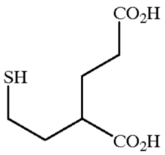 2-(2-sulfanylethyl)pentanedioic acid | 2 |
| 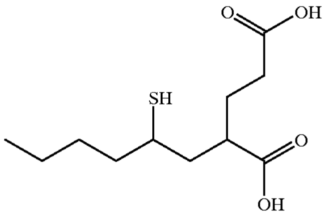 2-(2-sulfanylhexyl)pentanedioic acid | 1000 |

TABLE IV(a)-continued

| Compound | $EC_{50}$ (nM) |
| --- | --- |
| 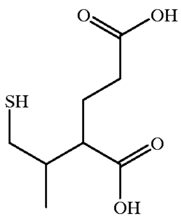 2-(1-methyl-2-sulfanylethyl)pentanedioic acid | 141 |
| 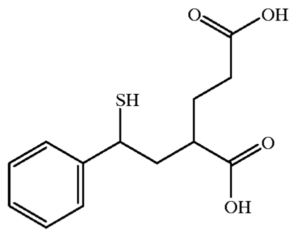 2-(2-phenyl-2-sulfanylethyl)pentanedioic acid | 29 |
| 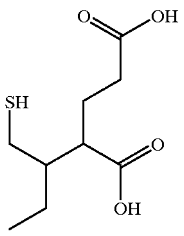 2-(1-ethyl-2-sulfanylethyl)pentanedioic acid | 62 |
| 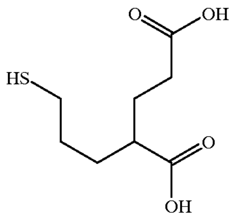 2-(3-sulfanylpropyl)pentanedioic acid | 13 |
| 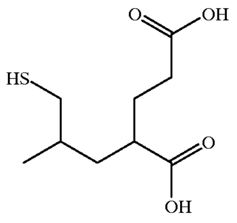 2-(3-sulfanyl-2-methylpropyl)pentanedioic acid | 80 |
| 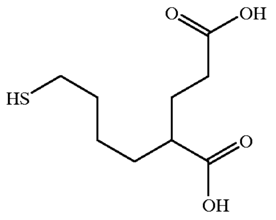 2-(4-sulfanylbutyl)pentanedioic acid | 36 |

TABLE IV(a)-continued

| Compound | $EC_{50}$ (nM) |
| --- | --- |
| 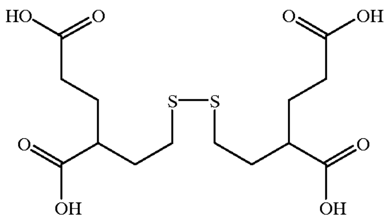 2-[2-[(3,5-dicarboxypentyl)dithio]ethyl]pentanedioic acid | 17.4 |

The dose-response of this effect, as measured by the % toxicity at different concentrations of NAALADase inhibitor 2-(phosphonomethyl)pentanedioic acid (Compound 3), is provided below in TABLE IV(b) and graphically presented in FIG. 1.

TABLE IV(b)

| Dose | % Toxicity | |
| --- | --- | --- |
| Control | 100.00 ± 9.0 | (n = 5) |
| 100 pM | 66.57 ± 4.38 | (n = 5) |
| 1 nM | 42.31 ± 9.34 | (n = 5) |
| 10 nM | 33.08 ± 9.62 | (n = 5) |
| 100 nM | 30.23 ± 9.43 | (n = 5) |
| 1 $\mu$M | 8.56 ± 8.22 | (n = 5) |

The results show that toxicity decreased as the concentration of 2-(phosphonomethyl)pentanedioic acid increased, suggesting that NAALADase inhibitors would be effective in treating ischemia or neuronal damage caused by ischemia.

The methods for this assay are described in detail below. Specifically, cell cultures were exposed to potassium cyanide and 2-deoxyglucose (2-DG)(10 mM) and analyzed for release of lactate dehydrogenase (LDH).

In Vitro Toxicity of NAAG

To examine the in vitro toxicity of NAAG, cortical cell cultures were treated with NAAG (in concentrations ranging from 3 $\mu$M to 3 mM) for 20 minutes. The toxicity measurement for each concentration of NAAG is provided below in TABLE V and graphically presented in FIG. 2.

TABLE V

| Dose of NAAG | % Toxicity | |
| --- | --- | --- |
| 3 $\mu$M | 3.51 | (n = 1) |
| 10 $\mu$M | 4.30 ± 3.12 | (n = 3) |
| 30 $\mu$M | 11.40 ± 6.17 | (n = 3) |
| 100 $\mu$M | 12.66 ± 5.50 | (n = 3) |
| 300 $\mu$M | 13.50 ± 4.0 | (n = 3) |
| 1 mM | 21.46 ± 4.20 | (n = 3) |
| 3 mM | 45.11 ± 4.96 | (n = 3) |

The results show that toxicity increased as the concentration of NAAG increased. The toxicity is attributed to the release of glutamate by NAAG when cleaved by NAALADase.

In Vitro Assay of NAALADase Inhibitors on Toxicity of NAAG

To examine the effect of NAALADase inhibitors on in vitro toxicity of NAAG, cortical cell cultures were treated with 1 $\mu$M 2-(phosphonomethyl)pentanedioic acid (Compound 3) during exposure to NAAG and for one hour thereafter. The toxicity measurement for each concentration of NAAG is provided below in TABLE VI and graphically presented in FIG. 3.

TABLE VI

| Dose of NAAG | % Toxicity | |
|---|---|---|
| 3 $\mu$M | −4.71 | (n = 1) |
| 10 $\mu$M | −3.08 ± 0.81 | (n = 3) |
| 30 $\mu$M | −4.81 ± 1.13 | (n = 3) |
| 100 $\mu$M | −2.87 ± 0.78 | (n = 3) |
| 300 $\mu$M | −2.09 ± 0.48 | (n = 3) |
| 1 mM | 0.26 ± 1.11 | (n = 3) |
| 3 mM | 16.83 ± 8.76 | (n = 3) |

Figure 2:
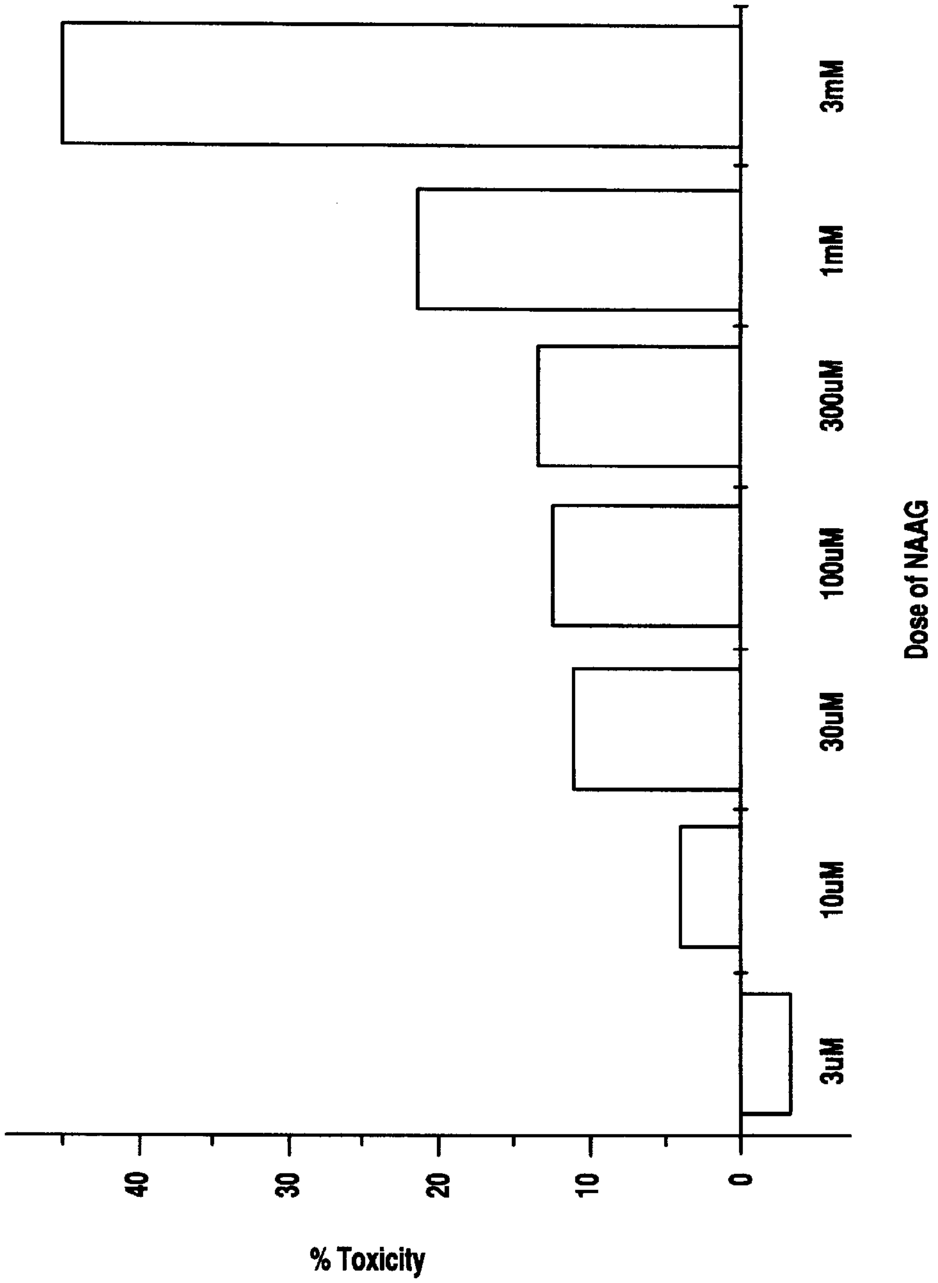
FIG. 2 is a bar graph plotting in vitro toxicity against various doses of NAAG to which cortical cell cultures were exposed.
Figure 3:
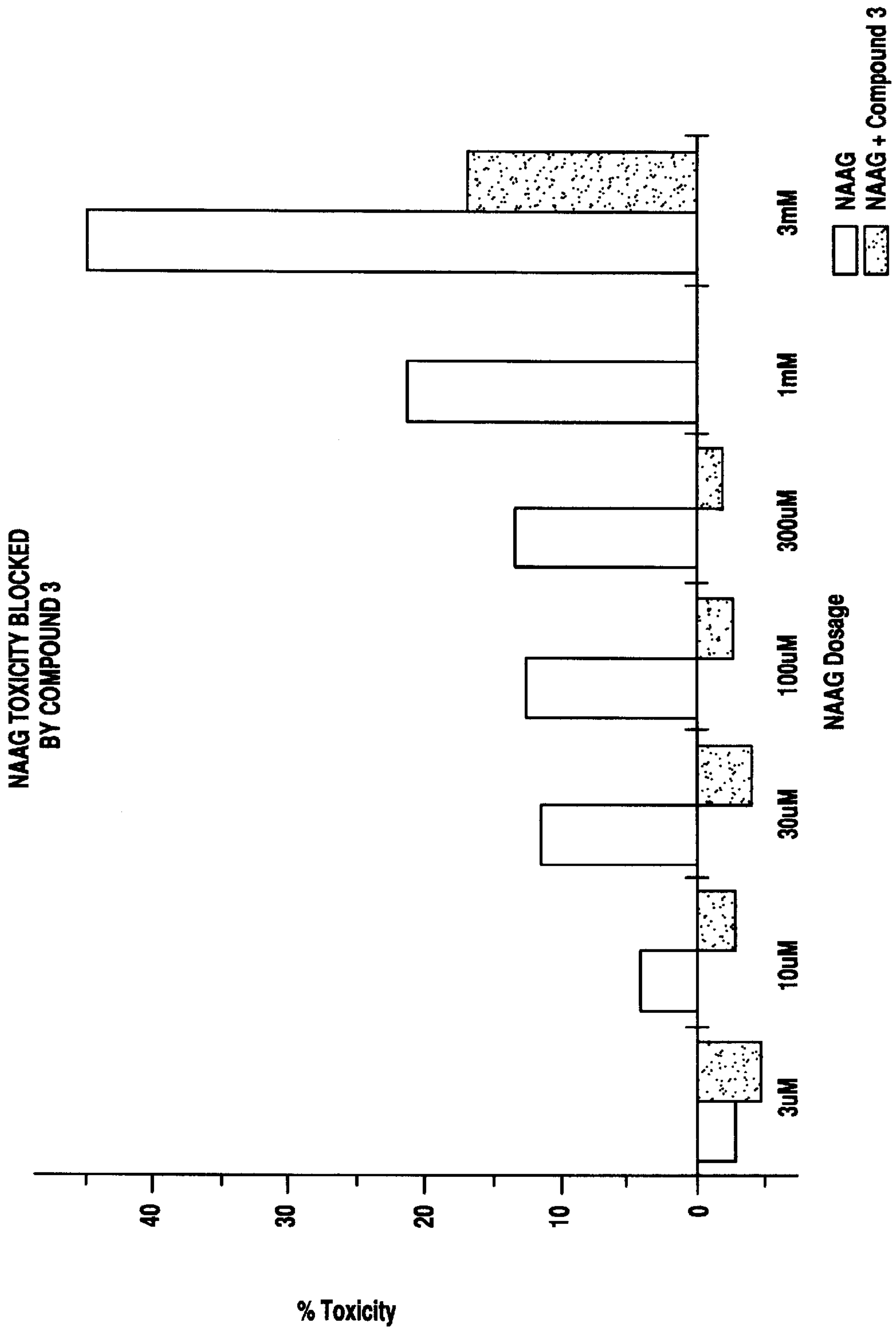
FIG. 3 is a bar graph plotting in vitro toxicity following treatment with 2-(phosphonomethyl)pentanedioic acid, against various doses of NAAG to which cortical cell cultures were exposed.

When compared to the results of FIG. 2/TABLE V, the results of FIG. 3/TABLE VI show that toxicity decreased considerably after treatment with the NAALADase inhibitor, suggesting that it would be effective in treating glutamate abnormalities.

Figure 4:
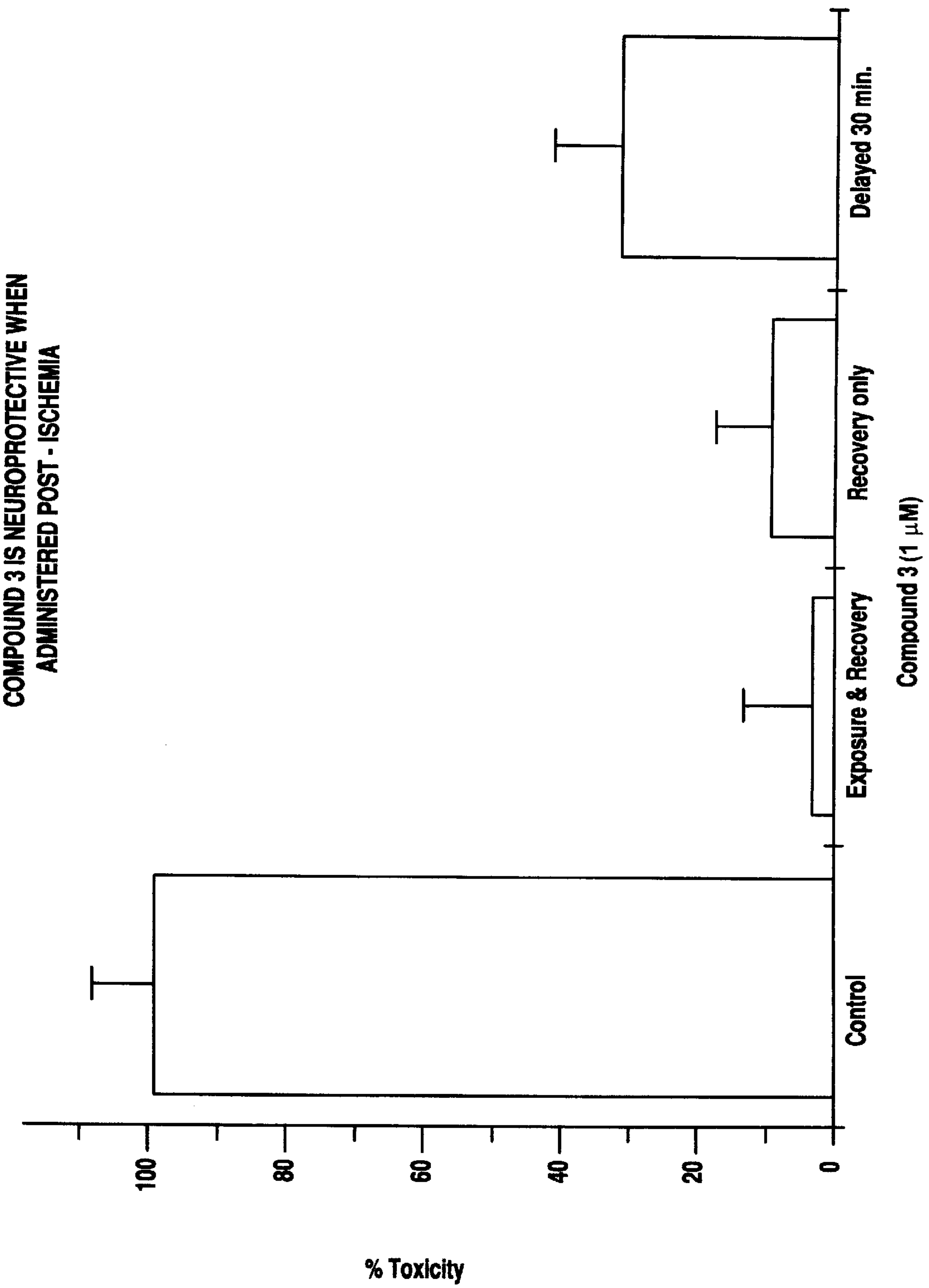
FIG. 4 is a bar graph plotting in vitro toxicity of ischemic insult against various times at which cortical cell cultures were treated with 2-(phosphonomethyl)-pentanedioic acid.
Figures 5A, 5B, 5C:
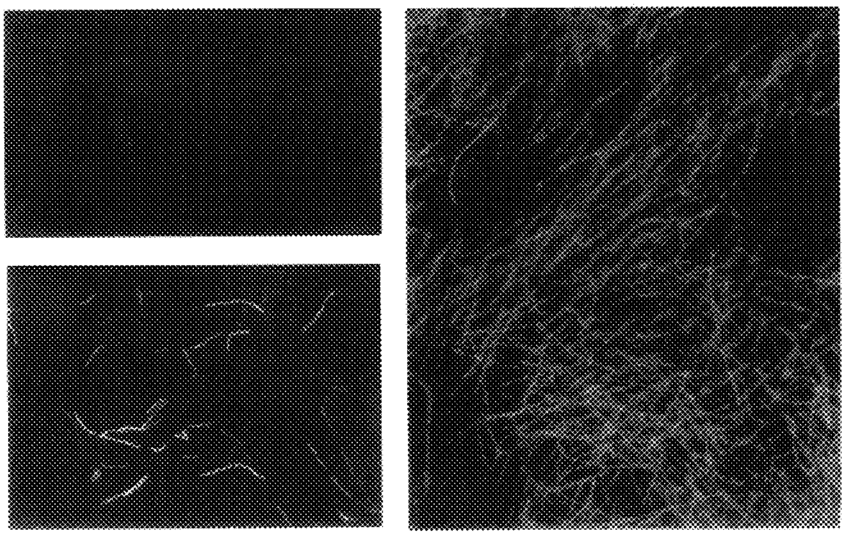
FIG. 5A is a microphotograph of an immunostained dorsal root ganglia-Schwann cell co-culture following treatment with progesterone.
FIG. 5B is a microphotograph of an immunostained dorsal root ganglia-Schwann cell co-culture following treatment with ascorbic acid.
FIG. 5C is a microphotograph of an immunostained dorsal root ganglia-Schwann cell co-culture following treatment with ascorbic acid and 2-(phosphonomethyl)-pentanedioic acid.

In Vitro Assay of NAALADASE Inhibitors on Ischemia at Different Times of Administration To examine the effect of NAALADase inhibitors on in vitro ischemic toxicity at different times of administration, cortical cell cultures were treated with 2-(phosphonomethyl) pentanedioic acid (Compound 3) (i) during an ischemic insult and for one hour thereafter (exposure and recovery); (ii) for one hour following ischemic insult (recovery only); and (iii) for one hour beginning 30 minutes after ischemic insult (delayed 30 minutes). The toxicity measurement for each time of administration is provided below in TABLE VII and graphically presented in FIG. 4.

TABLE VII

| Time of Administration Relative to Ischemic Insult | % Toxicity |
|---|---|
| Control | 100.00% |
| Exposure & Recovery | 2.54% |
| Recovery Only | 9.03% |
| Delayed 30 Minutes | 31.49% |

The results show that significant neuronal protection is achieved when NAALADase inhibitors are administered during exposure and recovery from an ischemic insult, and even after a 30 minute delay following the ischemic insult.

Protocol for In Vitro Toxicity Assay a. Cell Culture

Dissociated cortical cell cultures are prepared using the papain-dissociation method of Heuttner and Baughman (1986) as modified by Murphy and Baraban (1990). See TABLE VIII for the Dissociated Culture Protocol as used herein. Fetuses of embryonic day 17 are removed from timed pregnancy rats (Harlan Sprague Dawley). The cortex is rapidly dissected out in Dulbecco's phosphate-buffered saline, stripped of meninges, and incubated in a papain solution for 15 minutes at 37° C. The tissue is then mechanically triturated and pelleted at 500 g (1000–2000 rpm on swinging bucket Beckman). The pellet is resuspended in a DNAase solution, triturated with a 10 ml pipette x15-20, layered over a "10x10" solution containing albumin and trypsin inhibitor (see TABLE VIII for an example of a "10x10" solution), repelleted, and resuspended in a plating medium containing 10% fetal bovine serum (HyClone A-1111-L), 5% heat-inactivated Equine serum (HyClone A-3311-L), and 84% modified Earle's basal medium (MEM) (Gibco 51200-020) with high glucose (4.5 g/L), and 1 g/L $NaHCO_3$. Each 24-well plate is pretreated with poly-D-lysine (0.5 ml/well of 10 $\mu$g/ml) for 1 h and rinsed with water before plating. Cultures are plated at $2.5\times10^6$ cells/ml with each well of a 24 well plate receiving 500 $\mu$l/well. Alternatively, 35 mm dishes can be plated at 2 ml/dish, 6 well plates at 2 ml/well, or 12 well plates at 1 ml/well. After plating, 50% of the medium is changed every 3–4 days with growth serum containing 5% heat-inactivated Equine serum (HyClone A-3311-L), 95% modified Earle's basal medium (MEM) (Gibco 51200-020), and 1% L-Glutamine (Gibco 25030-081). Experiments are performed after 21 days in cultures. Cultures are maintained in a 5% $CO_2$ atmosphere at 37° C. These methodologies are described in further detail below in the TABLE VIII.

TABLE VIII

| DISSOCIATED CULTURE PROTOCOL | |
|---|---|
| I. PREPARE SOLUTIONS<br>Stocks/Solutions | |
| DNAase Stock, 1 ml (100x)<br>5 mg DNAase I (Worthington LS002004);<br>1 ml dissoc. EBSS;<br>freeze as 50 $\mu$l aliquots. | Dulbecco's PBS, 500 ml<br>4 gm NaCl (J. T. Baker 3624-01);<br>1.06 gm $Na_2HPO_4.7H_20$ (Fisher S373-3);<br>100 mg KCl (Fisher P217–500);<br>100 mg $KH_2PO_4$ (Siqma P-0662);<br>500 ml $dH_2O$;<br>adjust pH to 7.4 and sterile filter. |
| Dissociated EBSS, 500 ml<br>1.1 gm $NaHCO_3$;<br>50 ml EBSS stock (Gibco 14050-025);<br>450 ml $dH_2O$;<br>sterile filter. | EDTA Stock, 10 ml<br>184.2 mg EDTA sodium salt (Sigma ED4S);<br>10 ml $dH_{20;}$<br>sterile filter. |
| 10 and 10 Stock, 10 ml<br>100 mg BSA (Sigma A-4919);<br>100 mg Trypsin Inhibitor from Egg White (Sigma T-2011);<br>10 ml dissoc. EBSS;<br>sterile filter. | Poly-D-Lysine Stock, 5 ml<br>5 mg Poly-D-Lysine, 100–500 K (Sigma P-6407);<br>5 ml sterile water;<br>keep frozen. |
| Media | |
| Dissociated growth, 500 ml<br>500 ml MEM (Gibco 51200-020) containing glucose and $NaHCO_3$<br>(2.25 gm glucose and 0.5 gm $NaHCO_3$);<br>25 ml heat-inactivated Equine Serum (HyClone A-3311-L);<br>5 ml L-Glutamine (200 mM, 100x stock, Gibco 25030-081);<br>sterile filter.<br>15 ml heat-inactivated Equine Serum (HyClone A-z3311-L);<br>3 ml L-Glutamine (200 mM, 100x stock, Gibco 25030-081); (Gibco 15140-015);<br>1 ml Penicillin-Streptomycin stock. | Plating media, 300 ml<br>250 ml MEM containing glucose and sodium bicarbonate (2.25 gm glucose and 0.5 gm $NaHCO_3$ in 500 ml Gibco MEM 51200-020);<br>30 ml Fetal Bovine Serum (HyClone A-1111-L). |

TABLE VIII-continued

DISSOCIATED CULTURE PROTOCOL

| For papain dissociation: | For DNAase treatment: |
| --- | --- |
| 4 mg Cysteine (C-8277); | DNAase, 5 ml |
| 25 ml dissoc. EBSS; | 4.5 ml dissoc. EBSS; |
| 250 μl Papain stock (Worthington LS003126); | 500 μl "10 and 10" stock; |
| place in 37° C. waterbath until clear. | 50 μl DNAase stock. |
| | "10 and 10", 5 ml |
| | 4.5 ml of EBSS; |
| | 500 μl "10 and 10" stock. |

II. COAT DISHES
Use poly-d-lysine stock at 1:100 dilution to coat 24-well plates (0.5 ml/well) or at 1:10 dilution to coat 35 mm glass cover slips (1.0 ml/coverslip).
Leave until end of dissection.
III. DISSECT TISSUE
Use Harlan Sprague-Dawley timed pregnancy rats, ordered to arrive at E-17
Decapitate, spray abdomen down with 70% EtOH.
Remove uterus through midline incision and place in sterile dPBS.
Remove brains from embryos, leaving them in dPBS.
Brain removal: Penetrate skull and skin with fine forceps at lambda. Pull back to open posterior fossa. Then move forceps anteriorly to separate sagittal suture. Brain can be removed by scooping back from olfactory bulbs under the brain.
Move brains to fresh dPBS; subsequently, dissect away from cortex.
IV. PAPAIN DISSOCIATION
Transfer cortices equally to two 15 ml tubes containing sterile papain solution, maintained at 37° C.
Triturate xl with sterile 10 ml pipette.
Incubate only for 15 minutes at 37° C.
Spin at 500 G for 5 minutes (1000–2000 RPM on swinging bucket Beckman).
V. DNAase TREATMENT
Remove supernatant and any DNA gel layer from cell pellet (or pick up and remove pellet with pipette).
Move cell pellet to DNAase solution.
Triturate with 10 ml pipette, ×15–20.
Layer cell suspension over the "10 and 10" solution by pipetting it against the side of the tubes.
Spin again at 500 G for 5 minutes (cells will spin into "10 and 10" layer).
Wash tube sides with plating media without disturbing pellet.
Pipette off the media wash and repeat the wash.
VI. PLATE
Add about 4.5 ml plating media to each pellet for 5 ml volume.
Re-suspend with 10 ml pipette.
Pool cells into a single tube.
Quickly add 10 μl of the suspended cells to a hemocytometer so that they do not settle.
Count cells per large square, corresponding to 10 million cells/ml.
Put re-suspended cells into a larger container so that they number 2.5 million cells/ml.
Triturate to homogeneity.
Finish coating plates:
Aspirate or dump Lysine;
Wash ×1 with sterile water and dump.
Add plating media, with cells, to the plates as follows:

| | |
| --- | --- |
| 35 mm dishes | 2 ml/dish; |
| 6 well plate | 2 ml/well; |
| 12 well plate | 1 ml/well; |
| 24 well plate | 500 μl/well. |

VII. FEED
Cultures are usually made on Thursdays.
Start feeding twice a week; beginning the following Monday, feedings on Mondays and Fridays.
Remove 50% of volume and replace with fresh growth media.

b. Ischemic Insult Using Potassium Cyanide and 2-deoxyglucose

Twenty-one to twenty-four days following the initial cortical cell plating, the experiment is performed. The cultures are washed three times in HEPES buffered saline solution containing no phosphate. The cultures are then exposed to potassium cyanide (KCN)(5 mM) and 2-deoxyglucose (2-DG)(10 mM) for 20 minutes at 37° C. These concentrations were shown previously to induce maximal toxicity (Vornov et al., *J. Neurochem*, Vol. 65, No. 4, pp. 1681–1691 (1995)). At the end of 24 hours, the cultures are analyzed for release of the cytosolic enzyme lactate dehydrogenase (LDH), a standard measure of cell lysis. LDH measurements are performed according to the method of Koh and Choi, *J. Neuroscience Methods* (1987).

c. NAAG Induced Neurotoxicity

Cultures are assessed microscopically and those with uniform neuronal densities are used in the NAAG neurotoxicity trials.

At the time of the experiment, the cultures are washed once in HEPES-buffered saline solution (HBSS; NaCl 143.4 mM, HEPES 5 mM, KCl 5.4 mM, $MgSO_4$ 1.2 mM, $NaH_2PO_4$ 1.2 mM, $CaCl_2$ 2.0 mM, D-glucose 10 mM) (Vornov et al., 1995) and then exposed to various concentrations of NAAG for 20 minutes at 37° C. NAAG concentrations range from 3 μM to 3 mM, and include 3 μM, 10 μM, 30 μM, 100 μM, 300 μM, 1 mM, and 3 mM. At the end of exposure, the cells are washed once with HEPES buffered saline solution and then replaced with serum free modified Earle's basal medium. The cultures are then returned to the $CO_2$ incubator for 24 hour recovery.

d. Lactate Dehydrogenase Assay

Release of the cytosolic enzyme lactate dehydrogenase (LDH), a standard measure of cell lysis, is used to quantify injury (Koh and Choi, 1987). LDH-activity measurements are normalized to control for variability between culture preparations (Koh and Choi, 1987). Each independent experiment contains a control condition in which no NAALADase inhibitors are added; a small amount of LDH activity is found in these controls. This control measurement is subtracted from each experimental point. These values are normalized within each experiment as a percentage of the injury caused by NAAG/ischemia. Only main effects of NAALADase inhibitors are considered; interactions between dose and condition are not examined statistically.

A measurement of the potency of each compound tested is made by measuring the percentage of LDH release into the growth media after exposure to NAAG/ischemia plus NAALADase inhibitor or NAAG/ischemia plus saline (control). Since high concentrations of glutamate may be toxic to cells in certain circumstances, measurement of glutamate toxicity is observed using LDH as a standard measurement technique.

In Vivo Assay of NAALADase Inhibitors on Brain Injury following MCAO in Sprague-Dawley Rats To examine the neuroprotective effect of NAALADase inhibitors on brain injury in vivo, Sprague-Dawley rats were treated with a vehicle, 2-(2-sulfanylethyl)pentanedioic acid, or 2-(3-sulfanylpropyl)pentanedioic acid.

The control group received Hepes buffered saline.

Four drug treated groups received 2-(2-sulfanylethyl) pentanedioic acid. For each rat, the treatment was initiated at 60 minutes post middle cerebral artery occlusion (MCAO) by an IV bolus injection which was immediately followed by IV infusion for 4 hours at rate of 0.5 ml/hr. Group 1 (n=9) received a dose of 100 mg/kg IV bolus followed by 20 mg/kg/hr IV infusion for 4 hours. Group 2 (n=11) received a dose of 30 mg/kg IV bolus followed by 6 mg/kg/hr IV infusion for 4 hours. Group 3 (n=9)received a dose of 10 mg/kg IV bolus followed by 2 mg/kg/hr IV infusion for 4 hours. Group 3 rats were also treated at 120 minutes, 180 minutes and 360 minutes post-occlusion. Group 4 (n=8) received a dose of 3 mg/kg IV bolus followed by 3 mg/kg/hr IV infusion for 4 hours.

Two additional drug treated groups received 2-(3-sulfanylpropyl)pentanedioic acid. For each rat, the treatment was initiated at 120 minutes post middle cerebral artery occlusion (MCAO) by an IV bolus injection which was immediately followed by IV infusion for 4 hours at rate of 0.5 ml/hr. Group 5 received a dose of 30 mg/kg IV bolus followed by 6 mg/kg/hr IV infusion for 4 hours. Group 6 received a dose of 10 mg/kg IV bolus followed by 2 mg/kg/hr IV infusion.

Twenty two hours following the reperfusion, the rats were euthanized and their brains were removed. Seven coronal sections (2 mm thick) were taken and stained with 1% solution of 2,3,5-triphenyltetraxolium chloride (TTC) for 20 minutes and then fixed in 10% formalin. The anterior and posterior surface of the most rostral brain section and the posterior surface of each of the remaining 6 sections were imaged. The quantification of infarct size of each brain was obtained using a computer aided-digital imaging analysis system (LOATS). The brain regions completely lacking TTC-staining were characterized as representative of infarcted tissue. The total infarct volume for each rat was calculated by numeric integration of the respective sequential brain areas.

The total infarct volume for each group of rats is provided below in TABLES IX(a) and IX(b).

TABLE IX(a)

Rats treated with 2-(2-sulfanylethyl)pentanedioic acid

| Dose (mg/kg) | Admin. Time (minutes) | % Protect | p value |
|---|---|---|---|
| 100 | 60 post | 44 | 0.0142 |
| 30 | 60 post | 52 | 0.0020 |
| 10 | 60 post | 50 | 0.0058 |
| 10 | 120 post | 33 | 0.021 |
| 10 | 180 post | 47 | 0.014 |
| 10 | 360 post | 50 | 0.002 |
| 3 | 60 post | 52 | 0.0037 |
| 1 | 60 post | 20 | 0.3611 |

TABLE IX(b)

Rats treated with 2-(3-sulfanylpropyl)pentanedioic acid

| Dose (mg/kg) | Admin. Time (minutes) | % Protect | p value |
|---|---|---|---|
| 30 | 120 post | 52 | 0.0003 |
| 10 | 120 post | 21 | 0.29 |

Vehicle treated rats exhibited a mean total brain infarct volume of 265±33 $mm^3$.

Rats treated with 2-(2-sulf anylethyl)pentanedioic acid exhibited significantly smaller infarct size. The mean total brain infarct volumes for the four 2-(2-sulfanylethyl) pentanedioic acid treated groups were: 123±31 $mm^3$ for Group 1 (p=0.014 vs. vehicle group); 141±78 $mm^3$ for Group 2 (p=0.002 vs. vehicle group); 152±32 $mm^3$ for Group 3 (treated at 60 minutes post-occlusion; p=0.0058 vs. vehicle group); 117±22 $mm^3$ for Group 4 (p=0.0037 vs. vehicle group). These results indicate that 2-(2-sulfanylethyl)pentanedioic acid is neuroprotective in rat MCAO model of stroke when administered 60 minutes, 120 minutes, 180 minutes and 360 minutes post-occlusion.

Rats treated with 2-(3-sulfanylpropyl)pentanedioic acid at 30 mg/kg IV bolus followed by 6 mg/kg/hr IV infusion for 4 hours also exhibited significantly smaller infarct size than the vehicle treated rats. Thus, at that particular dose level, 2-(3-sulfanylpropyl)pentanedioic acid is neuroprotective in rat MCAO model of stroke when administered at 120 minutes post-occlusion.

Stroke patients often experience a significant temporal delay between the onset of ischemia and the time to initiation of therapy. Thus, there is a need for neuroprotectants with a long therapeutic window of opportunity. The data above shows that the inventive compounds have a therapeutic window of opportunity of at least 6 hours in rat MCAO model of stroke. One of ordinary skill in the art would expect that window to be greater in humans.

Protocol for In Vivo Assay of NAALADase Inhibitors on Brain Injury

Male Sprague-Dawley rats (260–320 g) were used. They were individually housed and allowed free access to food and water. Two days prior to the experiment, they were given restricted food if necessary to maintain the body weight. Each rat received two surgeries: femoral vein cannulation for IV infusion and MCAO. During surgeries, the rat was anesthetized with 1.5% halothane delivered in oxygen via an inhalation mask. The body temperature was monitored and regulated at normothermic level using a homeothermic heating system. First, a catheter was inserted into the left femoral vein. Thirty minutes later, the rat was reanesthetized for MCAO surgery. The MCAO was achieved using the endovascular suture method described by Long et al., Stroke, Vol. 20, pp. 84–91 (1989). Specifically, the right external carotid artery (ECA) was exposed, coagulated and transected. A 3-0 monofilament nylon suture with a blunted tip and a coat of 0.05% Poly-1-Lysine was introduced into the proximal stump of the ECA via an arteriotomy. It was advanced 22 mm from the carotid bifurcation until it lodged in the proximal region of the anterior cerebral artery, thereby occluding the origin of the MCA. The rats were allowed to wake up; 2 hours later, the rats were reanesthetized for reperfusion, during which the nylon suture was retracted to the stump of the ECA allowing blood recirculation to the MCA.

In Vivo Assay of NAALADase Inhibitors on Stroke-Induced Rise in Brain Glutamate Levels To examine the effect of NAALADase inhibitors on hyperglutamatergic disorders in vivo, rats with stroke-induced rise in brain glutamate levels were treated with a vehicle or 2-(phosphonomethyl)pentanedioic acid (Compound 3).

Figure 7:
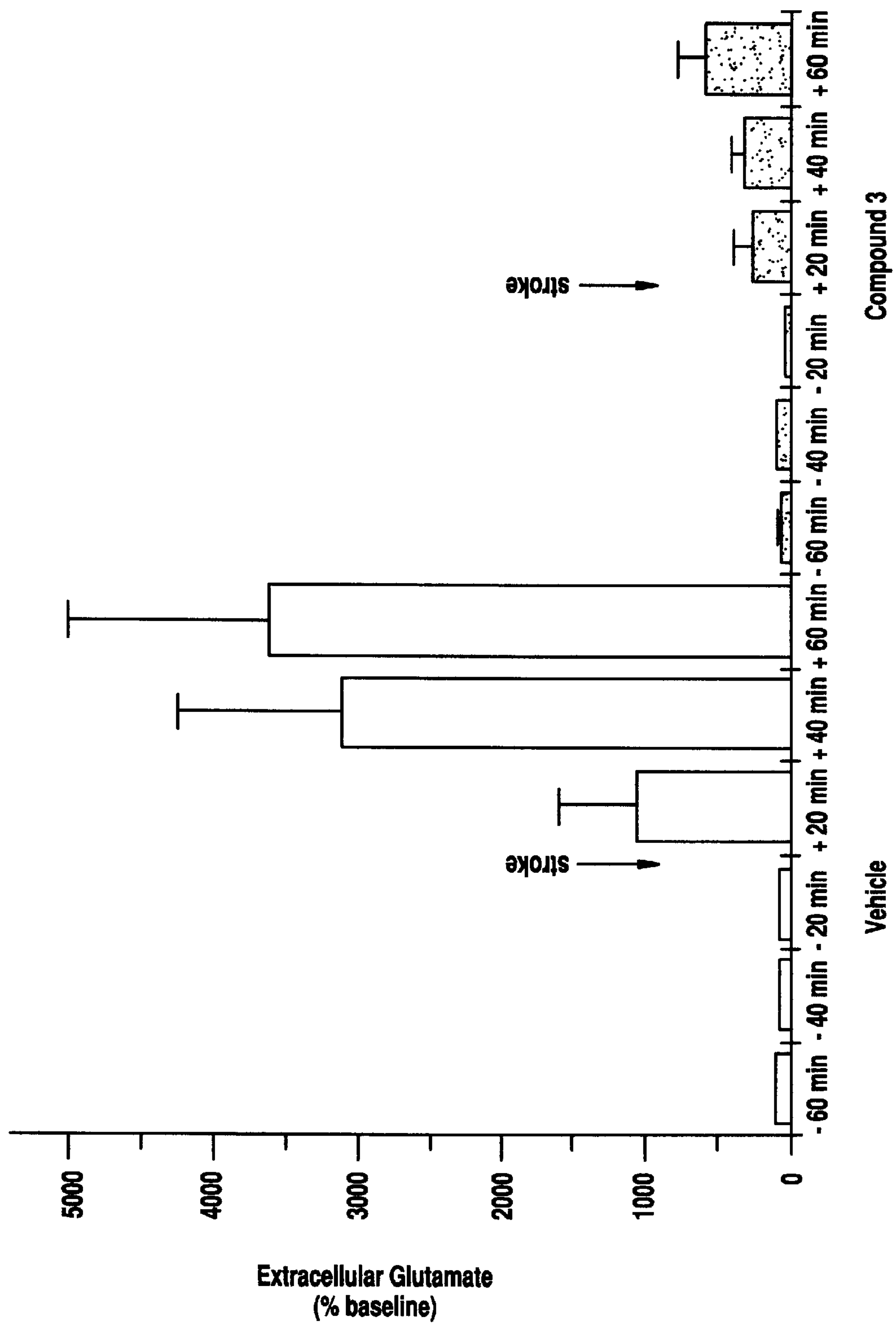
FIG. 7 is a bar graph plotting in vivo extracellular glutamate increases in the striatum of rats treated with a vehicle or 2-(phosphonomethyl)pentanedioic acid after sustaining middle cerebral artery occlusion.
Figure 8:
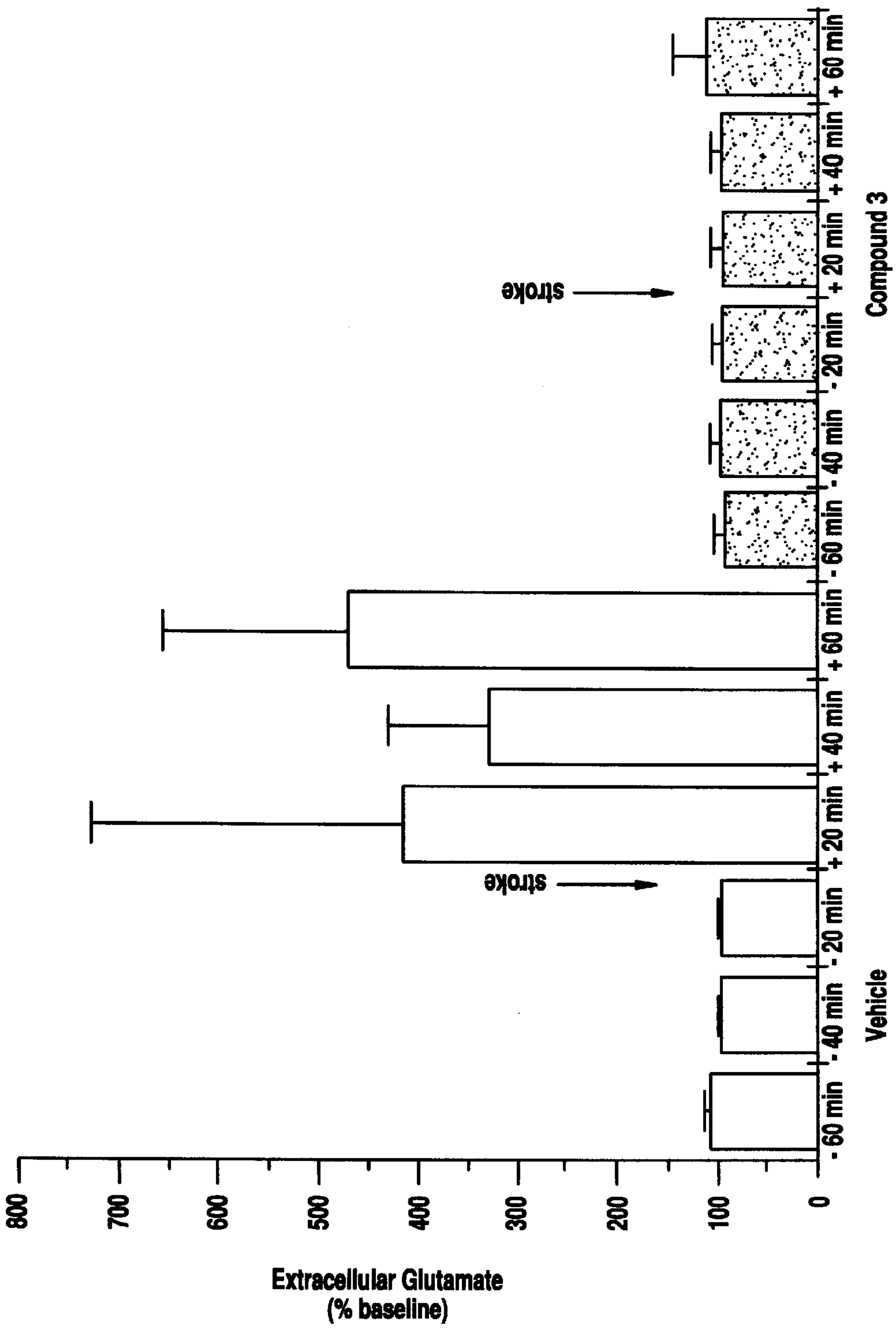
FIG. 8 is a bar graph plotting in vivo extracellular glutamate increases in the parietal cortex of rats treated with a vehicle or 2-(phosphonomethyl)pentanedioic acid after sustaining middle cerebral artery occlusion.
Figure 9:
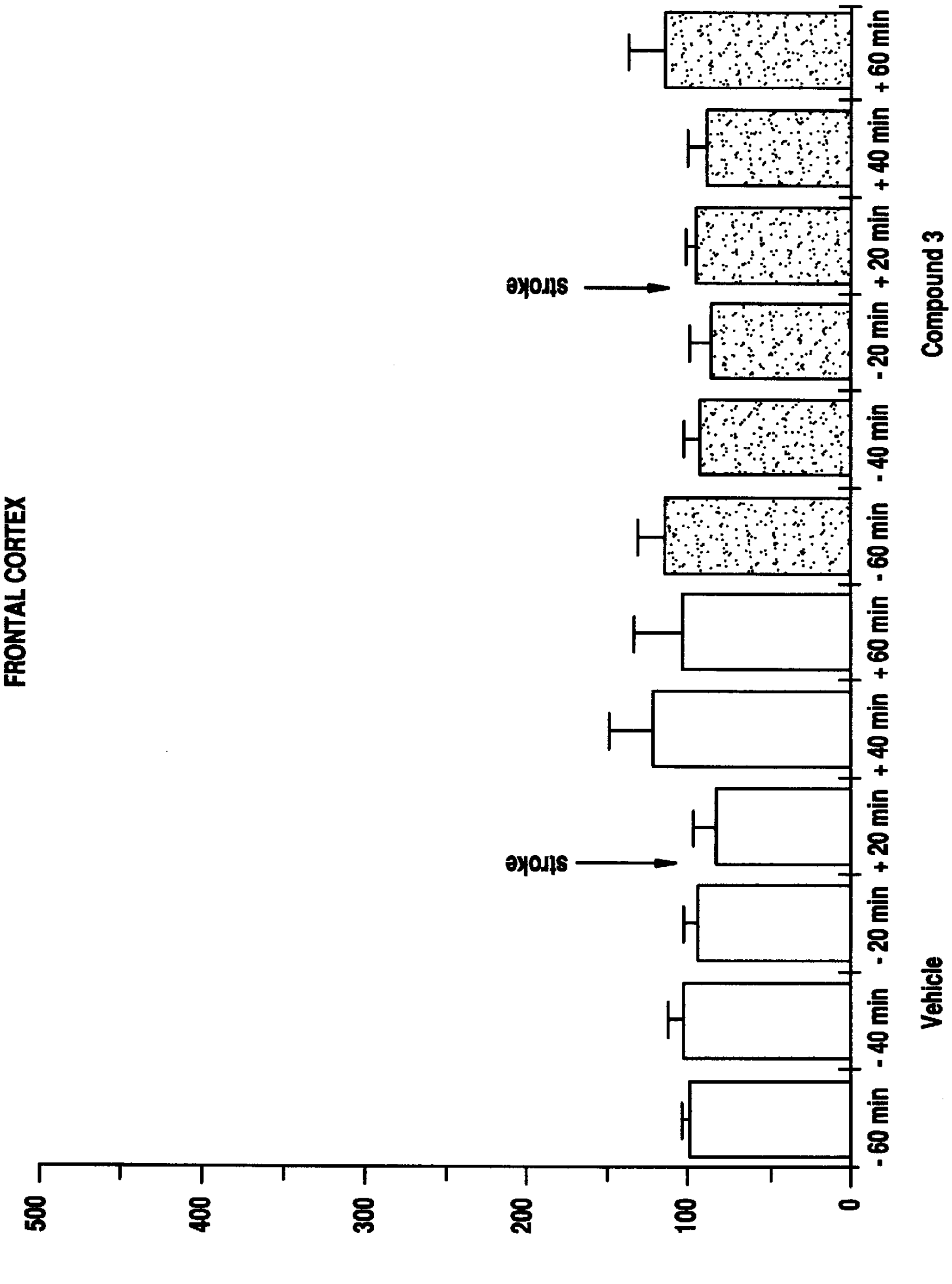
FIG. 9 is a bar graph plotting in vivo extracellular glutamate increases in the frontal cortex of rats treated with a vehicle or 2-(phosphonomethyl)pentanedioic acid after sustaining middle cerebral artery occlusion.

The results are graphically presented in FIGS. 7, 8 and 9.

The results show that 2-(phosphonomethyl)pentanedioic acid treatment (100 mg/kg IP followed by 20 mg/kg/hr IV) significantly attenuated stroke-induced extracellular glutamate increases in the striatum (FIG. 7) as compared to vehicle treated rats ($p<0.05$), and completely prevented concurrent glutamate changes in the parietal cortex ($p<0.01$; FIG. 8). In contrast, there was no significant effect of the stroke itself on glutamate in the frontal cortex and no subsequent difference between the vehicle and 2-(phosphonomethyl)-pentanedioic acid treated groups (FIG. 9). Values are expressed as % baseline where baseline constitutes the mean of three consecutive 20 minute samples preceding stroke. Absolute basal (pretreatment) values for glutamate (mean±SEM) in caudate, parietal and frontal cortices were 0.25+0.1, 1.1+0.3 and 0.6+0.1 $\mu$M, respectively, in the vehicle treated rats, and 0.46+0.1, 2.0+0.7 and 0.9+0.3 $\mu$M, respectively, in the 2-(phosphonomethyl)pentanedioic acid treated rats.

Protocol for In Vivo Assay of NAALADase Inhibitors on Stroke-Induced Rise in Brain Glutamate Levels Male Sprague Dawley rats (270–330 g, n=5–6 per group) were implanted with concentric microdialysis probes similar to previously described procedures (Britton et al., *J. Neurochem.*, Vol. 67, pp. 324–329 (1996)). In brief, under halothane anaesthesia, probes (constructed in-house using Cuprophane capillary membrane; 10K mw cut off; 2 mm dialyzing length) were implanted into the frontal cortex (AP=+3.5; ML=3; DIV=3), caudate nucleus (AP=0; ML=3; DV=6.6), and parietal cortex (AP=−2; ML=5; DV=3) (coordinates in mm relative to bregma and dura, respectively), regions believed to represent core and penumbral areas of ischemia-induced injury. Glutamate levels in dialysate were determined using precolumn o-phthaldialdehyde derivatization, followed by HPLC with fluorometric detection.

Approximately 20 hours after probe implantation, the rats were dialyzed with perfusion fluid (125 mM NaCl, 2.5 mM KCl, 1.18 mM $MgCl_2$ and 1.26 mM $CaCl_2$) at a rate of 2.5 $\mu$l/min. Following a 60 minute stabilization period, dialysis samples were collected every 20 minutes. After collecting 3 baseline samples, the rats were anaesthetized with halothane and subjected to temporary ischemia using the filament method of MCAO (Britton et al., *Life Sciences*, Vol. 60, No. 20, pp. 1729–1740 (1997)). In brief, the right external carotid artery (ECA) was exposed and its branches coagulated. A 3-0 monofilament nylon suture was introduced into the internal carotid artery via an arteriotomy in the ECA and advanced until it lodged in the proximal region of the anterior cerebral artery, thus occluding the origin of the MCA. The endovascular suture was retracted to allow reperfusion 2 hours after occlusion.

Body temperature was maintained normothermic throughout stroke surgery and reperfusion procedures. The rats were dosed IP with 100 mg/kg 2-(phosphonomethyl) pentanedioic acid at −20 minute pre-occlusion and IV with 20 mg/kg/hr for 4 hours at the time of occlusion. Dialysis samples were collected every 20 minutes from unanesthetized rats. Following 24 hours of reperfusion, the rats were sacrificed, their brains were removed, and 7 coronal sections (2 mm thick) were taken from the region beginning 1 mm from the frontal pole and ending just rostral to the cortico-cerebellar junction. Analysis of ischemic cerebral damage was achieved using TTC staining and computer assisted image analysis as described by Britton et al. (1997), supra.

In Vitro Assay of NAALADase Inhibitors on Myelination in Dorsal Root Ganglia-Schwann Cell Co-Cultures Inhibition of NAALADase results in significant increase in the number of myelinated axons and myelin thickness as compared to vehicle-treated mice following sciatic nerve cryolesion (*Soc. Neurosci. Abstr.*, Vol. 23, No. 2, p. 2302 (1997)). The inventors hypothesized that NAALADase may play a role in signaling myelin formation and inhibition of NAALADase may facilitate myelination. To test this hypothesis, the inventors examined the effects of several NAALADase inhibitors in a well established in vitro model system of myelination. Dorsal root ganglia-Schwann cell co-cultures were established as previously described (Einheber et al., *J. Cell. Biol.*, Vol. 123, p. 1223). Following 7 days in co-culture, myelination was initiated following the addition of serum and ascorbic acid with various doses of NAALADase inhibitors (1 nM to 10 $\mu$M) or progesterone (20 nM; positive control). The extent of myelination was examined between days 14–21 using immunocytochemical staining for myelin basic protein (MBP), a known myelin marker. Qualitative analysis of the immunostained cultures revealed a significant dose-response related increase in the number of myelinated axons following the addition of NAALADase inhibitors as compared to axons in vehicle-treated cultures. As depicted in FIGS. 5A–C and 6A–C, a two week treatment of the NAALADase inhibitors 2-(phosphonomethyl)pentanedioic acid and 2-[[(pentafluorobenzyl)hydroxyphosphinyl]methyl] pentanedioic acid (1 nM) caused a significant increase in the immunostaining of MBP. Cultures treated with high dose 2-(phosphonomethyl)pentanedioic acid or 2-[[(pentafluorobenzyl)hydroxyphosphinyl]methyl] pentanedioic acid (1 $\mu$M) had a greater extent of myelination than cultures treated with maximal doses of ascorbic acid and progesterone. These results suggest that inhibition of NAALADase may facilitate myelination and may be useful clinically in the treatment of demyelinating diseases.

In Vivo Assay of NAALADase Inhibitors on Myelin Formation Following Sciatic Nerve Cryolesion It was recently demonstrated that NAALADase is down-regulated in glial cells as they start to form myelin and is absent in myelinating Schwann cells. Based on this data, the inventors hypothesized that inhibition of NAALADase may affect the signaling mechanism between axons and Schwann cells and result in increasing myelination. To test this hypothesis, the inventors examined the effect of 2-(phosphonomethyl)pentanedioic acid (Compound 3) on nerve regeneration and myelination following cryolesion of the sciatic nerve in male mice.

The results are provided below in TABLE X and graphically presented in FIGS. 10A and 10B.

TABLE X

IN VIVO EFFECT OF NAALADASE INHIBITORS ON MYELIN FORMATION FOLLOWING SCIATIC NERVE CRYOLESION

| | 2-(phosphono-methyl)pentane-dioic acid | vehicle |
|---|---|---|
| ratio of # of myelinated axons (drug/vehicle) | 1.5 | |
| # of myelinated lamellae (ave. + SEM) | 16.53 ± 0.65 | 13.77 ± 0.09 |
| % increase of myelinated lamellae over vehicle | 20% | |
| significance by t-test | p < 0.005 | |

Figure 10A:
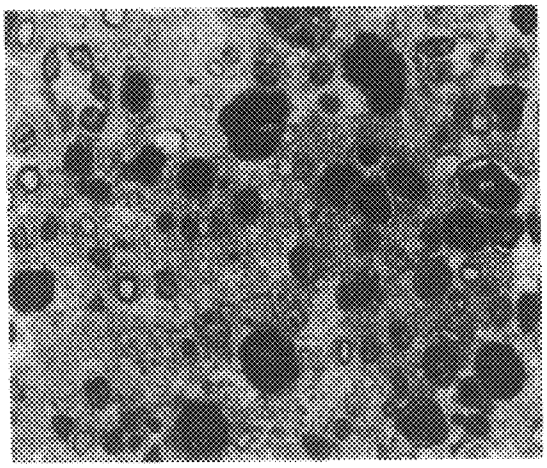
FIG. 10A is a photomicrograph of mouse sciatic nerve treated with a vehicle following cryolesion.
Figure 10B:
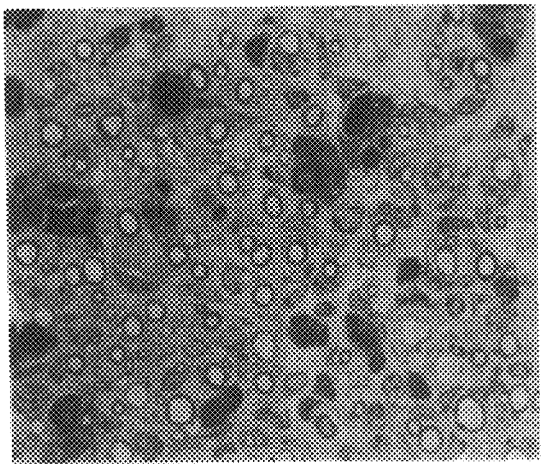
FIG. 10B is a photomicrograph of mouse sciatic nerve treated with 2-(phosphonomethyl)pentanedioic acid following cryolesion.

As detailed in FIGS. 10A and 10B, both light and transmission electron microscopy (TEM) examination of the nerve 3 mm distal to the site of cryolesion demonstrated a significant increase in the number of myelinated axons (1.5-fold increase) and myelin thickness (20% increase, $p<0.005$), as compared to nerves in mice treated with vehicle.

FIGS. 10A and 10B show photomicrographs of this effect. Sections were stained with toluidine blue which stains myelin. Sciatic nerves treated with 2-(phosphonomethyl) pentanedioic acid containing implants, compared with sciatic nerves treated with vehicle containing implants, exhibited an increase in myelinated axon number as well as an increase in myelin thickness.

Protocol for In Vivo Assay of NAALADase Inhibitors on Myelin Formation Following Sciatic Nerve Cryolesion Cryolesion of the mouse sciatic nerve was performed according to Koenig et al., *Science*, Vol. 268, pp. 1500–1503 (June 1995). In brief, each mouse was anesthetized and its sciatic nerve was exposed in the upper thigh and cryolesioned using a copper cryode (diameter=0.5 mm) that was dipped in liquid nitrogen and repeatedly applied to the upper part of the nerve. The extent of the lesion was approximately 1 mm.

2-(Phosphonomethyl)pentanedioic acid was incorporated into silicone strips according to the method of Connold et al., *Developmental Brain Res*, Vol. 28, pp. 99–104 (1986), and was implanted at the site of cryolesion on day 0 and replaced on days 3, 6, 9 and 12. Approximately 2.5 μg/day of 2-(phosphonomethyl)-pentanedioic acid was released from the silicone implants each day. Both right and left sciatic nerves of each mouse were lesioned; right-side nerves were treated with silicone implant strips containing vehicle alone while left-side nerves were treated with silicone implants containing 2-(phosphonomethyl)-pentanedioic acid. Fifteen days after surgery, the mice were sacrificed and their sciatic nerve segments were collected and processed for light microscopy and TEM analysis. Randomly chosen fields 2–3 mm distal to the lesion were qualitatively analyzed by light microscopy using 1-micrometer-thick toluidine blue stained cross sections and photographic images were captured.

In Vivo Assay of NAALADase Inhibitors on Parkinson's Disease

To examine the effect of NAALADase inhibitors on Parkinson's Disease in vivo, MPTP lesioned mice were treated with 2-(phosphonomethyl)pentanedioic acid (Compound 3) or a vehicle.

Figure 11:
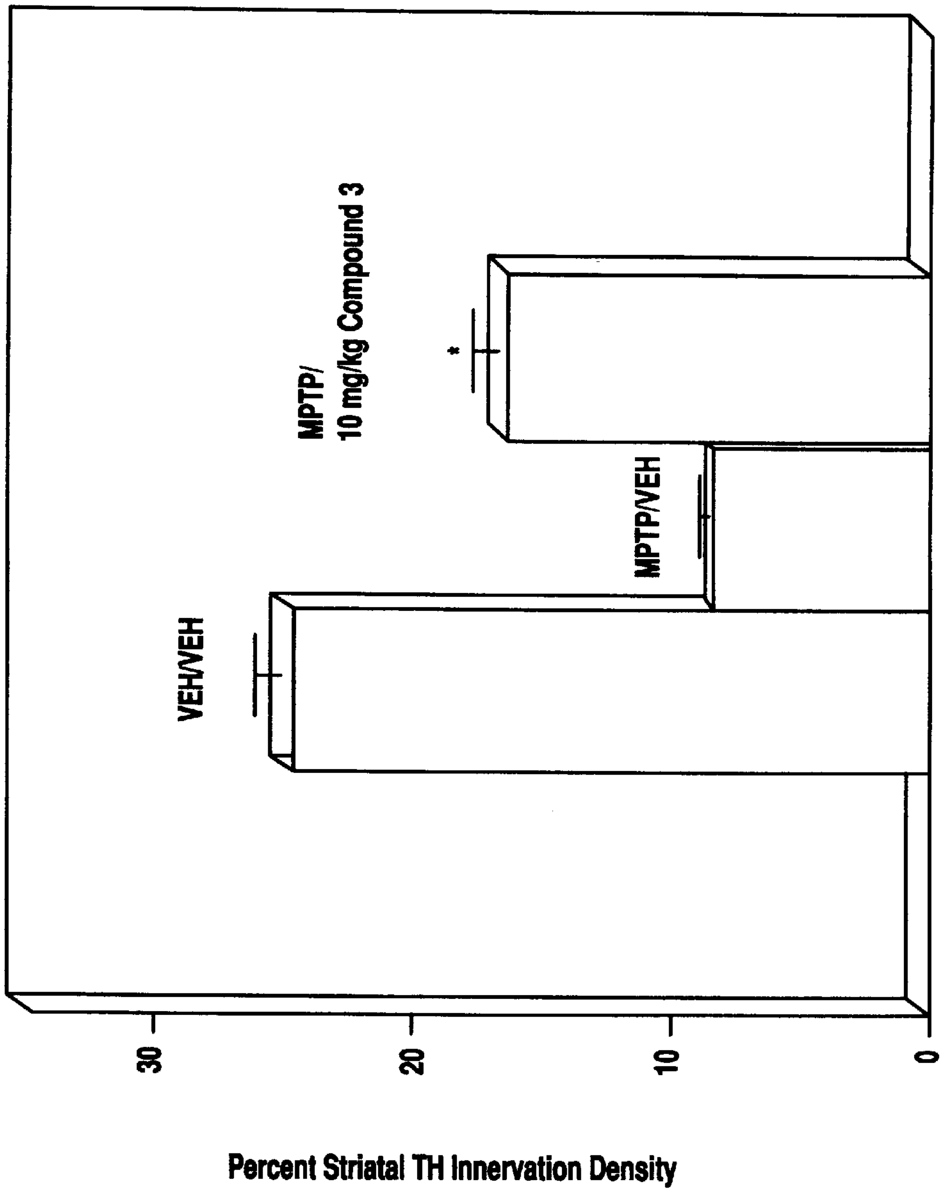
FIG. 11 is a bar graph plotting percent striatal TH innervation density against the treatment of mice with vehicle alone, vehicle following MPTP, or 2-(phosphonomethyl) pentanedioic acid following MPTP.

The percent of dopaminergic neurons for each group of mice is provided below in TABLE XI and graphically presented in FIG. 11.

TABLE XI

IN VIVO EFFECT OF NAALADASE INHIBITORS ON PARKINSON'S DISEASE

| | Percent Strial TH Innervation Density (mean ± SEM) |
|---|---|
| vehicle/vehicle | 24.74 ± 1.03 |
| MPTP/vehicle | 7.82 ± 0.68 |
| MPTP/2-(phosphonomethyl)-pentanedioic acid | 16.28 ± 0.98 |

Mice treated with MPTP and vehicle exhibited a substantial loss of functional dopaminergic terminals as compared to non-lesioned mice (approximately 68% loss). Lesioned mice receiving 2-(phosphonomethyl)pentanedioic acid (10 mg/kg) showed a significant recovery of TH-stained dopaminergic neurons ($p<0.001$). These results indicate that 2-(phosphonomethyl)pentanedioic acid protects against MPTP-toxicity in mice.

Protocol for In Vivo Assay of NAALADase Inhibitors on Parkinson's Disease

MPTP lesioning of dopaminergic neurons in mice was used as an animal model of Parkinson's Disease, as described by Steiner, *Proc. Natl. Acad. Sci.*, Vol. 94, pp. 2019–2024 (March 1997). In brief, four week old male CD1 white mice were dosed IP with 30 mg/kg of MPTP for 5 days. 2-(Phosphonomethyl)pentanedioic acid (10 mg/kg) or a vehicle was administered SC along with the MPTP for 5 days, as well as for an additional 5 days following cessation of MPTP treatment. At 18 days following MPTP treatment, the mice were sacrificed and their brains were removed and sectioned. Immunostaining was performed on saggital and coronal brain sections using anti-tyrosine hydroxylase (TH) antibodies to quantitate survival and recovery of dopaminergic neurons.

In Vivo Assay of NAALADase Inhibitors on Dynorphin-Induced Spinal Cord Injury

To examine the neuroprotective effect of NAALADase inhibitors on excitotoxic spinal cord injury in vivo, rats which had sustained dynorphin-induced spinal cord injury were treated with a vehicle or 2-(phosphono-methyl) pentanedioic acid.

Figure 12:
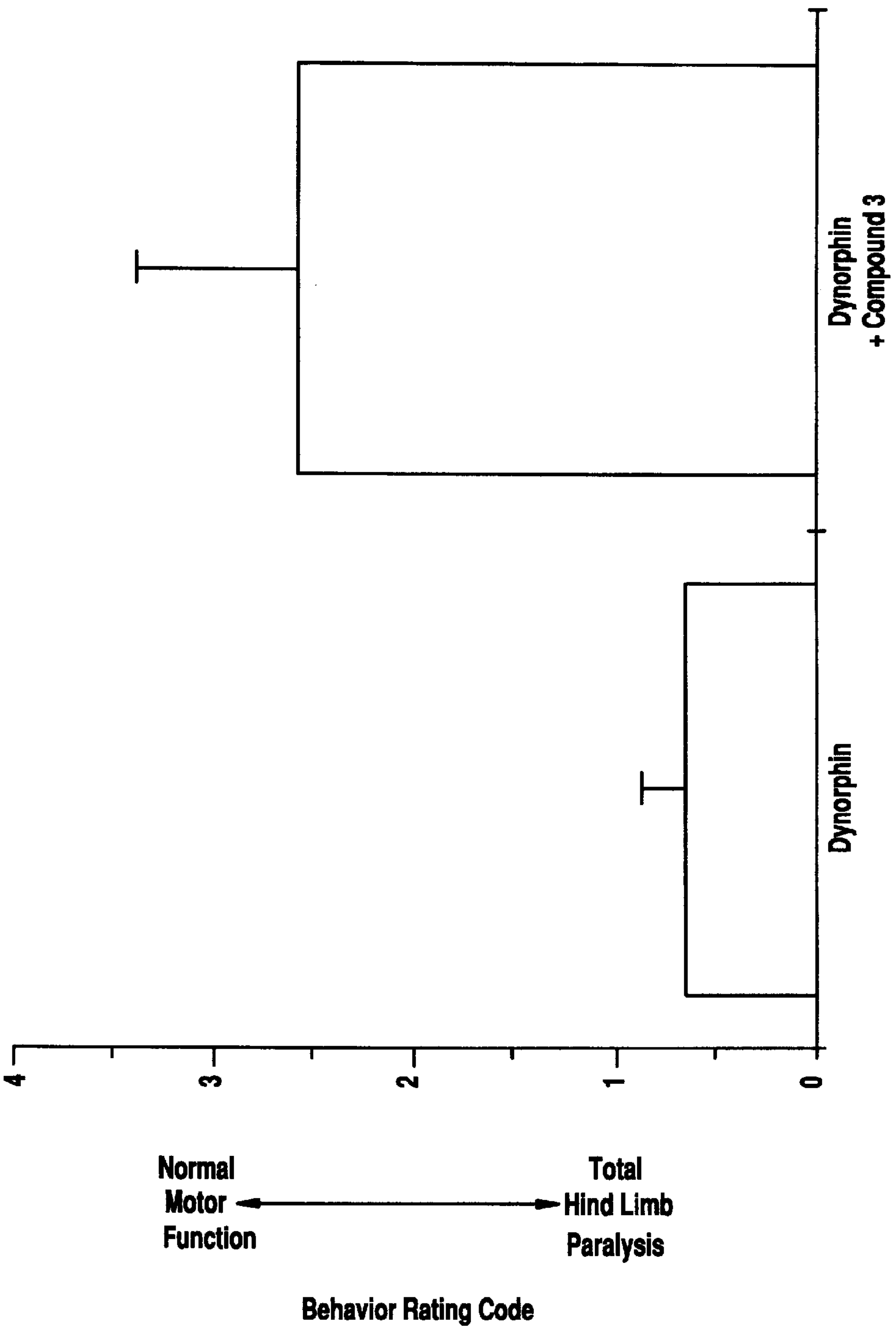
FIG. 12 is a bar graph plotting the neurological function code against the treatment of rats with dynorphin A alone or 2-(phosphonomethyl)pentanedioic acid with dynorphin A.

The results are graphically presented in FIG. 12.

When co-administered with dynorphin A, 2-(phosphonomethyl)pentanedioic acid (4 μmoles) caused significant improvement in motor scores by 24-hour post-injection, as compared to vehicle treated rats ($p<0.05$, Kruskal-Wallis comparison). The rats were characterized as ambulatory or not on the basis of their assigned neurological scores (0 to 4). At 24 hours post-injection, 73% of the 15 rats co-treated with 2-(phosphonomethyl)pentanedioic acid were ambulatory, in contrast to 14% of the 14 vehicle co-treated rats ($p<0.05$). These results indicate that 2-(phosphonomethyl)pentanedioic acid provides effective protection against dynorphin-induced spinal cord injury.

Protocol for In Vivo Assay of NAALADase Inhibitors on Dynorphin-Induced Spinal Cord Injury Spinal Subarachnoid Injections Dynorphin-induced spinal cord injury was performed according to Long et al., *JFET*, Vol. 269, No. 1, pp. 358–366 (1993). In brief, spinal subarachnoid injections were delivered using 30-gauge needles inserted between the L4–L5 vertebrae of male Sprague-Dawley rats (300–350 g). The rats were anesthetized with halothane and dorsal midline incisions were made immediately rostral to the pelvic girdle. By using the vertebral processes as guides, the needle was advanced to pass into the subarachnoid space surrounding the cauda equina. Correct needle placement was verified by CSF flow from the needle after its insertion. Injections were delivered using a Hamilton microsyringe in a total volume of 20 μl which contained dynorphin (20 nmol), the cannula flush and 2-(phosphonomethyl)pentanedioic acid or vehicle. After injections, the incisions were treated with the topical antibacterial furazolidone and closed with wound clips. Rapid recovery from the halothane anesthesia enabled neurological evaluations to be made within 5 minutes of injections.

Neurological Evaluations

Neurological function was evaluated using a 5-point ordinal scale, with scores being assigned as follows: 4=normal motor function; 3=mild paraparesis, with the ability to support weight and walk with impairment; 2=paraparesis, with the ability to make walking movements without fully supporting weight; 1=severe paraparesis, in which rats could make limited hind limb movement, but not walking movement; and 0=flaccid paralysis, with complete absence of any hind limb movement. Neurological evaluations were made 24 hours after dynorphin A injection.

Statistics

Differences in the neurological scores among treatment groups were determined by means of the Mann-Whitney U test or the Kruskal-Wallis test.

In Vitro Assay of NAALADase Inhibitors on Amyotrophic Lateral Sclerosis (ALS)

To examine the neuroprotective effect of NAALADase inhibitors on Amyotrophic Lateral Sclerosis (ALS), spinal cord organotypic cultures were treated with threohydroxyaspartate (THA), 2-phosphonomethyl)pentanedioic acid, or THA combined with 2-(phosphonomethyl)pentanedioic acid, and assayed for choline acetyltransferase (ChAT) activity.

The ChAT activity for each treatment of the spinal cord organotypic cultures is provided below in TABLE XII and graphically presented in FIG. 13.

TABLE XII

NEUROPROTECTIVE EFFECT OF NAALADASE INHIBITORS IN SPINAL CORD CULTURE MODEL OF ALS

| Treatment | ChAT Activity (% of Control) |
|---|---|
| control | 100 ± 22.1 |
| 2-(phosphonomethyl)-pentanedioic acid alone | 108 ± 18.4 |
| THA alone | 36 ± 12.1 |
| 2-(phosphonomethyl)-pentanedioic acid and THA | 121 ± 18.8 |

Figure 13:
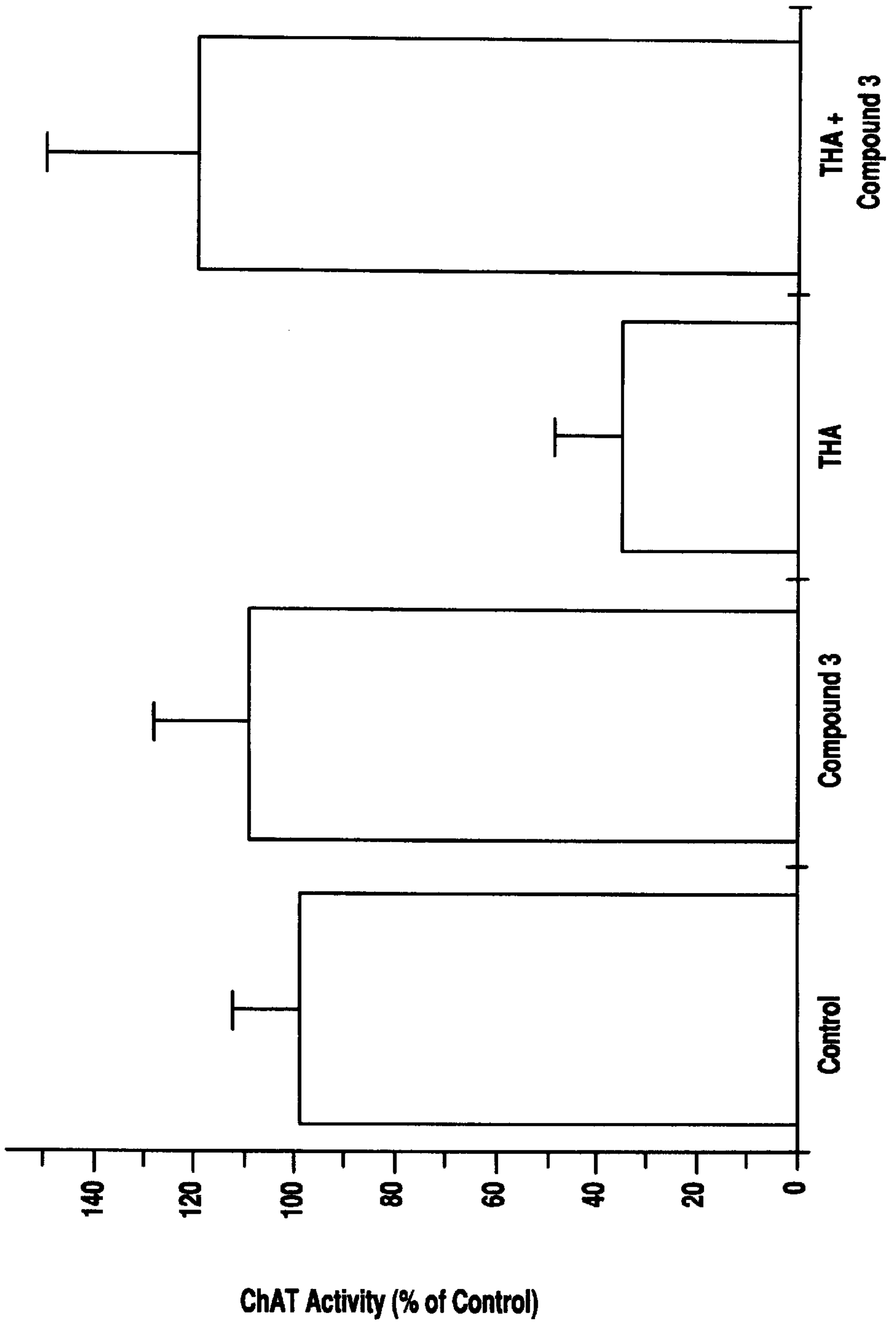
FIG. 13 is a bar graph plotting the ChAT activity of rat spinal cord organotypic cultures against the treatment of the cultures with 2-(phosphonomethyl)pentanedioic acid alone, threohydroxyaspartate (THA) alone, or THA with 2-(phosphonomethyl)pentanedioic acid.

As shown in FIG. 13, treatment of the spinal cord organotypic cultures with 100 $\mu$M THA resulted in a reduction of ChAT activity to approximately 36% of control cultures. Co-incubation of the cultures with THA and 2-(phosphonomethyl)pentanedioic acid (100 mM–10 $\mu$M) significantly protected the cultures from THA toxicity.

Figure 14:
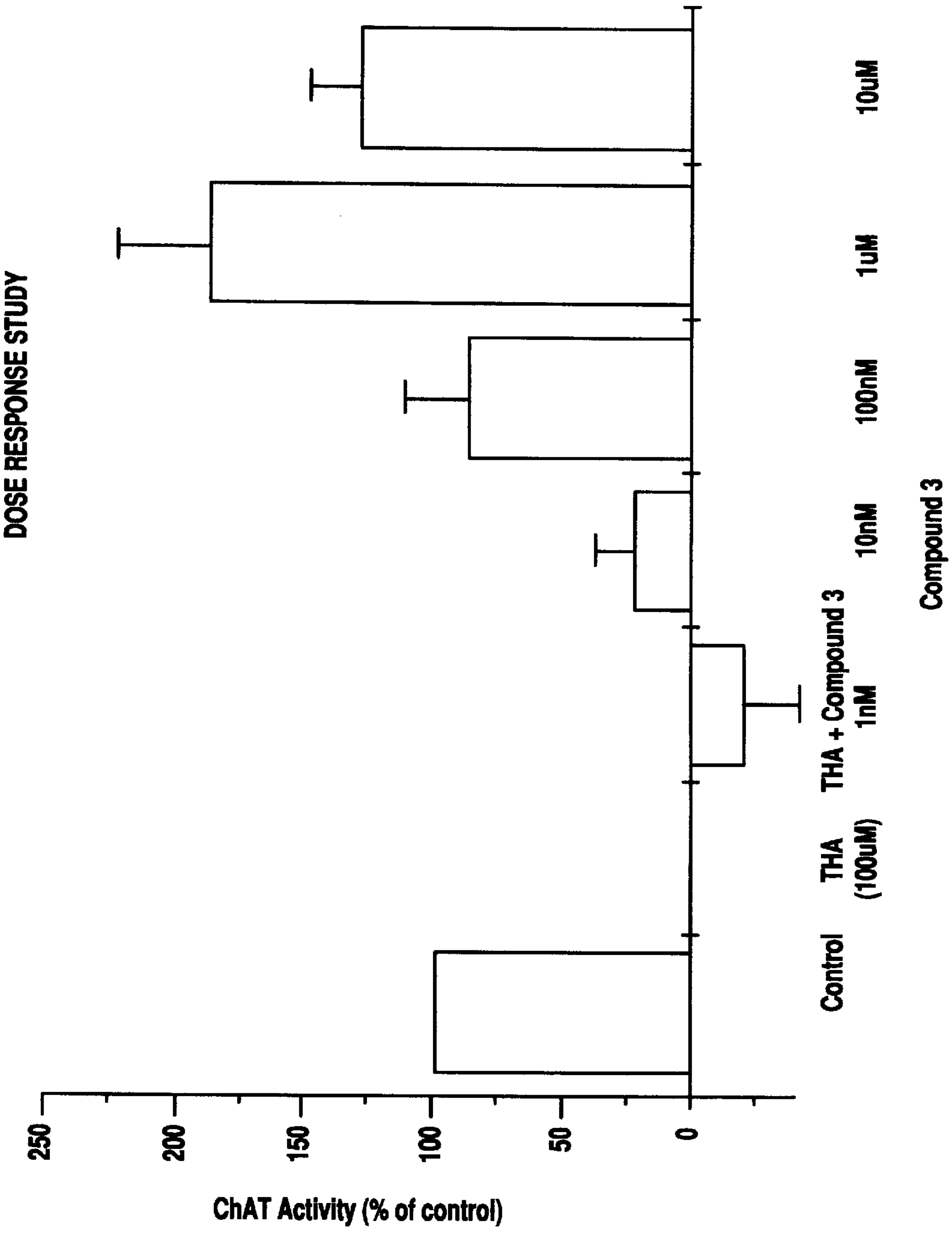
FIG. 14 is a bar graph plotting the ChAT activity of rat spinal cord organotypic cultures against various doses of 2-(phosphonomethyl)pentanedioic acid with which the cultures were treated in the presence of THA.

The dose-response of this effect is provided below in TABLE XIII and graphically presented in FIG. 14.

TABLE XIII

NEUROPROTECTIVE EFFECT OF NAALADASE INHIBITORS IN SPINAL CORD CULTURE MODEL OF ALS

| | ChAT Activity (% of Control) |
|---|---|
| control | 100.0 |
| THA | 0 |
| THA and 1 nM 2-(phosphonomethyl)-pentanedioic acid | −23.9 ± 18.6 |
| THA and 10 nM 2-(phosphonomethyl)-pentanedioic acid | 23.1 ± 12.5 |
| THA and 100 nM 2-(phosphonomethyl)-pentanedioic acid | 87.5 ± 21.7 |
| THA and 1 $\mu$M 2-(phosphonomethyl)-pentanedioic acid | 187.7 ± 32.8 |
| THA and 10 $\mu$M 2-(phosphonomethyl)-pentanedioic acid | 128.7 ± 17.2 |

Spinal cord cultures were incubated with various doses of 2-(phosphonomethyl)pentanedioic acid (1 nM to 10 $\mu$M) in the presence of THA (100 $\mu$M) for 14 days. As shown in FIG. 14, 2-(phosphonomethyl)pentanedioic acid (Compound 3) exhibited dose-dependent protection against THA-induced toxicity with maximal effects at 1 $\mu$M.

Protocol for In Vivo Assay of NAALADase Inhibitors on Amyotrophic Lateral Sclerosis (ALS)

Spinal Cord Organotypic Cultures

Organotypic cultures were prepared from lumbar spinal cord of 8 day old rats, as described by Rothstein et al., *J. Neurochem.*, Vol. 65, No. 2 (1995), and Rothstein et al., *Proc. Natl. Acad. Sci. USA*, Vol. 90, pp. 6591–6595 (July. 1993). In brief, lumbar spinal cords were removed and sliced into 300 $\mu$M-thick-dorsal-ventral sections, and five slices were placed on Millipore CM semipermeable 30-mm-diameter membrane inserts. The inserts were placed on 1 ml of culture medium in 35-mm-diameter culture wells. Culture medium consisted of 50% minimal essential medium and phosphate-free HEPES (25 mM), 25% heat-inactivated horse serum, and 25% Hanks' balanced salt solution (GIBCO) supplemented with D-glucose (25.6 mg/ml) and glutamine (2 mM), at a final pH of 7.2. Antibiotic and antifungal agents were not used. Cultures were incubated at 37° C. in 5% $CO_2$ containing humidified environment (Forma Scientific). Culture medium, along with any added pharmacological agents, was changed twice weekly.

Chronic Toxicity Model with THA

For all experiments, cultures were used 8 days after preparation at which time threohydroxyaspartate (THA; 100 $\mu$M), 2-(phosphonomethyl)pentanedioic acid (100 pM–10 $\mu$M), or THA (100 $\mu$M) ±2-(phosphonomethyl)pentanedioic acid (100 pM–10 $\mu$M) were added to the culture medium. Drugs were incubated for an additional 13 to 20 days with the 100 $\mu$M THA. At the end of this period, cultures were collected assayed for ChAT activity as described below.

ChAT Assays

To determine choline acetyltransferase (ChAT) activity, the spinal cord tissues in each dish (five slices) were pooled and frozen (−75° C.) until assay. ChAT activity was measured radiometrically by described methods using [$^3$H] acetyl-CoA (Amersham; Fonnum, 1975). Protein content of tissue homogenate was determined by a Coomassi Protein Assay kit (Pierce, Rockford, Ill.).

In Vivo Assay of NAALADase Inhibitors on Ethanol Consumption in Alcohol-Preferring Rats To test the effect of NAALADase inhibitors on ethanol consumption, alcohol-preferring rats were treated with saline or a 50, 100 or 200 mg/kg dose of 2-(phosphonomethyl)pentanedioic acid (Compound 3) prior to ethanol access. The ethanol intake of the rats following treatment is graphically presented in FIG. 15.

Figure 15:
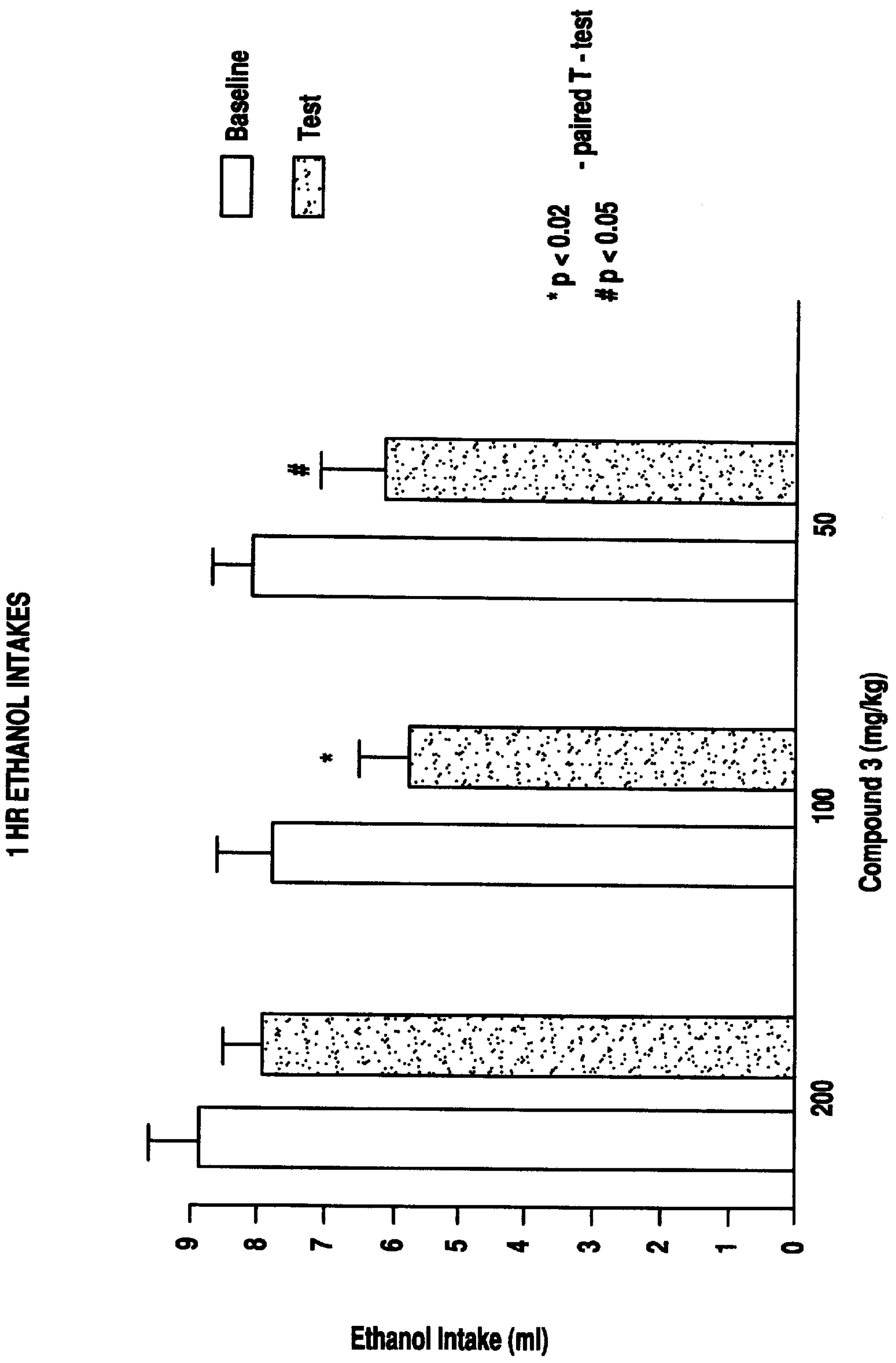
FIG. 15 is a bar graph plotting the ethanol intake of alcohol-preferring rats against various doses of 2-(phosphonomethyl)pentanedioic acid with which the rats were treated.

As shown in FIG. 15, the 200 mg/kg dose of 2-(phosphonomethyl)pentanedioic acid exhibited no effect, whereas both the 50 and 100 mg/kg doses significantly reduced ethanol consumption by approximately 25% ($p<0.05$) during the 1 hour access period. Body weights and 24 hour water intakes were not altered at any of the 3 doses. If 2-(phosphonomethyl)pentanedioic acid is acting centrally, these data suggest that NAALADase may be involved in neuronal systems regulating alcohol-drinking behavior.

Saline Baseline: 8.9±0.7

200 mg/kg 2-(phosphonomethyl)pentanedioic acid: 8±0.5

Saline Baseline: 7.8±0.8

100 mg/kg 2-(phosphonomethyl)pentanedioic acid: 5.8±0.7

Saline Baseline: 8.1±0.6

50 mg/kg 2-(phosphonomethyl)pentanedioic acid: 6.2±0.9

Protocol for In Vivo Assay of NAALADase Inhibitors on Ethanol Consumption in Alcohol-Preferring Rats The effect of systemic administration of 2-(phosphonomethyl)pentanedioic acid was examined on ethanol intake in the alcohol-preferring (P) line of rats, as described by Panocka et al., *Pharm. Biochem. and Behavior*, Vol. 52, No. 2, pp. 255–259 (1995) and Murphy et al., *Alcohol*, Vol. 2, pp. 349–352 (1985). In brief, 2-(phosphonomethyl)pentanedioic acid (50, 100 and 200 mg/kg IP) was tested in female P rats (n=8) given daily 1 hour scheduled access to a 10% (v/v) ethanol solution. A within-subject design was used where 2-(phosphonomethyl) pentanedioic acid treatments were tested once per week. Baseline ethanol drinking consisted of the mean of the 3 days prior to testing in which saline injections were given. 2-(Phosphonomethyl)pentanedioic acid or saline, administered IP in 1 ml/kg volumes, were injected 10–15 minutes prior to ethanol access. 24 hour water and daily body weights were recorded to assess non-specific drug effects. Results were analyzed using paired t-tests with baseline and test day values serving as the independent variables. Ethanol intake was recorded as amount of solution consumed (mls).

Figure 16B:
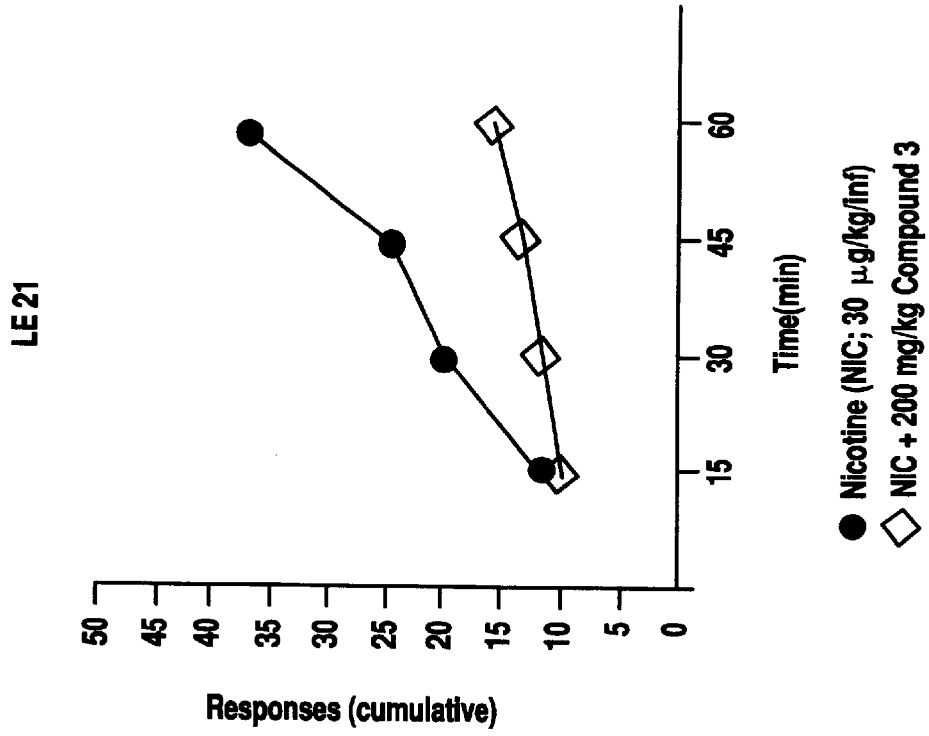
FIG. 16 is a graph plotting the cumulative nicotine intake of rats during a 1 hour test session, before which the rats had been trained to self-administer nicotine and pretreated with a vehicle or 2-(phosphonomethyl)-pentanedioic acid.
Figure 16A:
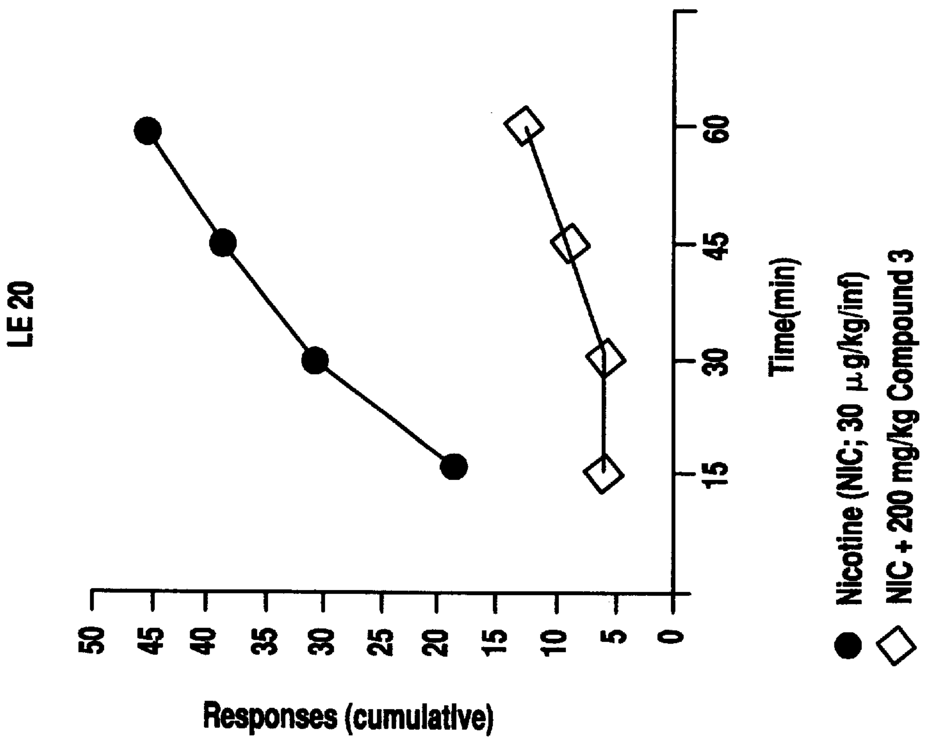

In Vivo Assay of NAALADase Inhibitors on Nicotine Self-Administration in Male Long-Evans Rats To test the effect of NAALADase inhibitors on nicotine self-administration, male Long-Evans rats trained to self-administer nicotine were treated with a 200 mg/kg dose of 2-(phosphonomethyl)pentanedioic acid (Compound 3) prior to nicotine access. The cumulative nicotine intake of the rats following treatment is graphically presented in FIG. 16.

Figure 17A:
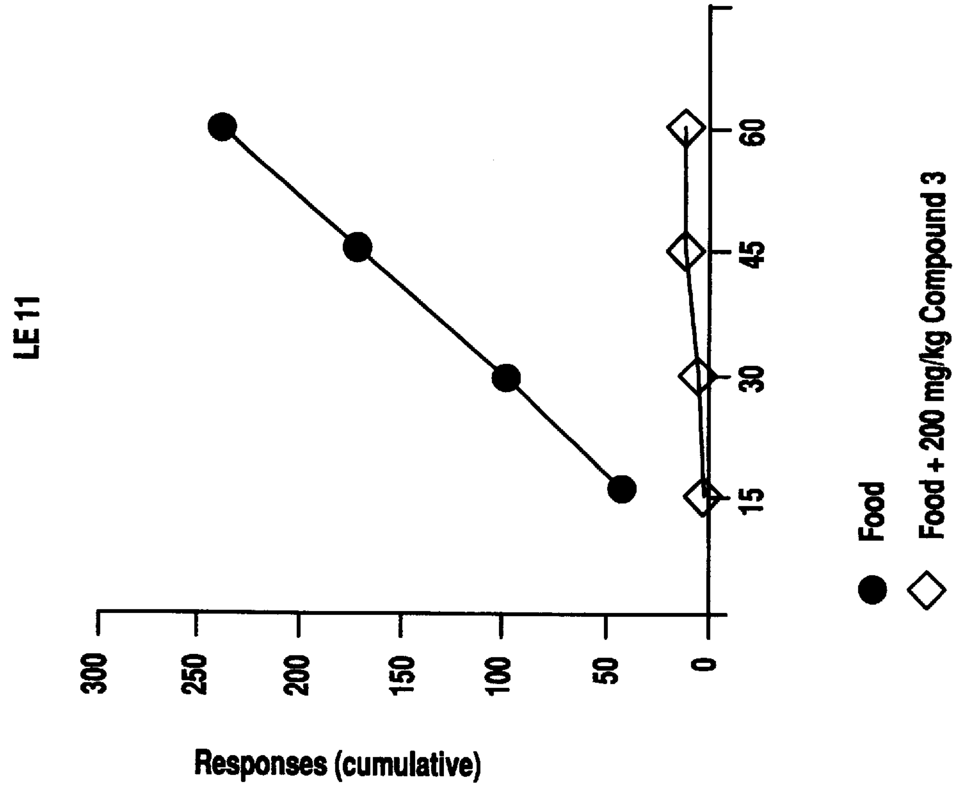
FIG. 17 is a graph plotting the cumulative food intake of rats during a 1 hour test session, before which the rats had been trained to self-administer nicotine and pretreated with a vehicle or 2-(phosphonomethyl)-pentanedioic acid.
Figure 17B:
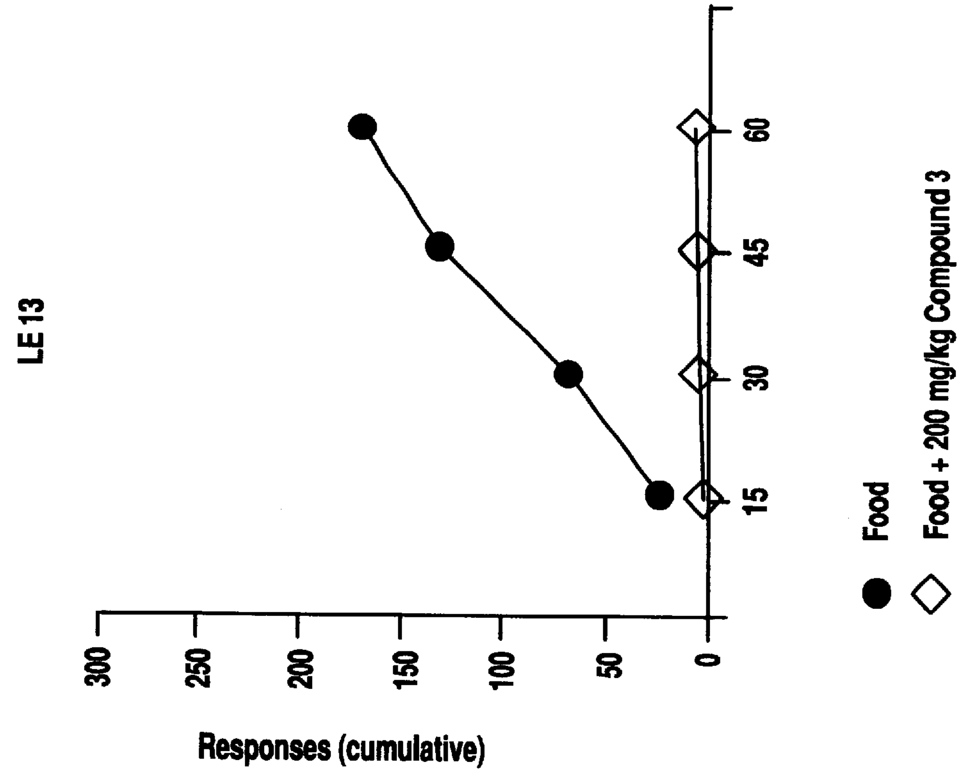

The results show that the 200 mg/kg dose of 2-(phosphonomethyl)pentanedioic acid reduced nicotine self-administration from 23 to 5 infusions during the 1 hour access period. As graphically presented in FIG. 17, the cumulative food intake of the rats also decreased during the same period of time. While these data suggest that factors other than 2-(phosphonomethyl)pentanedioic acid may be responsible for the reduction in nicotine self-administration, they do not disprove NAALADase's involvement in the neuronal systems regulating nicotine use. The effect on the rats' food intake could be attributed to toxicity caused by an excessive drug dose.

Protocol for In Vivo Assay of NAALADase Inhibitors on Nicotine Self-Administration in Male Long-Evans Rats Male Long-Evans rats were trained to self-administer nicotine on a fixed ratio schedule of reinforcement, as described by Corrigall et al., *Psychopharmacology*, Vol. 104, No. 2, pp. 171–176 (1991) and Corrigall et al., *Psychopharmacology*, Vol. 107, Nos. 2–3, pp. 285–289 (1992). In brief, male Long-Evans rats were food deprived for a short period of time (24–48 hours) and trained to press a lever in an operant responding chamber on an FR-1 schedule of food reinforcement. Once trained, each rat was surgically prepared with a chronic intravenous catheter implanted into the jugular vein. The rats were allowed 1 week to recover from surgery.

After 1 week, nicotine self-administration studies were initiated on an FR-1 with a 60 second signaled time-out following each infusion. During time-out, responding on the lever had no scheduled consequence. Nicotine self-administration sessions were 60 minutes in duration. Each nicotine infusion contained 30 $\mu$g of nicotine/kg rat and were delivered in a volume of 54 $\mu$l over an infusion duration of 0.3 seconds. 15 minutes before the self-administration sessions, the rats were pre-treated intraperitoneally with 2-(phosphonomethyl)-pentanedioic acid at doses of 10, 20 and 30 mg/kg. Food intake was monitored during the nicotine self-administration sessions to assess non-specific drug effects.

Figure 30:
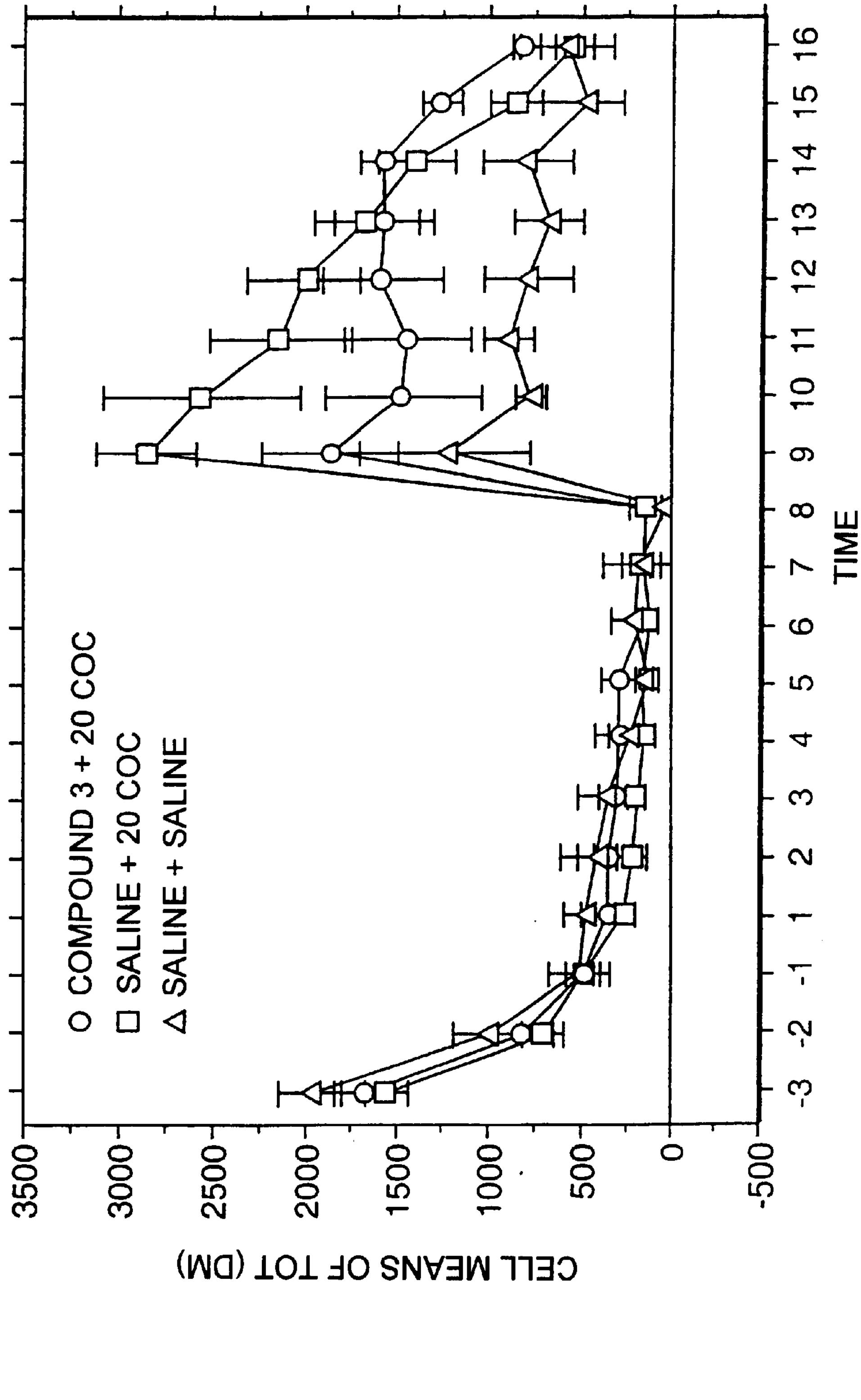
FIG. 30 is a graph plotting cocaine (20 mg/kg)-induced locomotor activity of rats against the days following treatment with 2-(phosphonomethyl)pentanedioic acid with cocaine, saline with cocaine, and saline with saline.

In Vivo Assay of NAALADase Inhibitors on Behavioral Sensitization to Cocaine in Sprague-Dawley Rats NAALADase hydrolyzes the abundant neuropeptide NAAG to liberate glutamate (GLU). The inventors hypothesized that inhibition of NAALADase could attenuate sensitization by preventing this source of GLU. The inventors evaluated the influence of the NAALADase inhibitor 2-(phosphonomethyl)pentanedioic acid (Compound 3) upon the sensitization which develops to the psychomotor stimulant effects of cocaine. Male Sprague-Dawley rats received home cage injections of cocaine (20 mg/kg/day×5 days; i.p.) or sale (1.0 ml/kg). Fifteen minutes prior to injections, they received 2-(phosphonomethyl)pentanedioic acid at 10 and 50 mg/kg doses. Cocaine (20 mg/kg)-induced locomotor activity was assessed 3 days later. Acute cocaine increased activity of cocaine exposure (e.g. sensitization). In animals which had received 2-(phosphonomethyl)pentanedioic acid with cocaine, the enhancement of activity was significantly reduced. 2-(phosphonomethyl)pentanedioic acid on its own did not alter basal locomotor activity or the response to saline. The results are graphically presented in FIG. 30. The data show that 2-(phosphonomethyl)pentanedioic acid attenuates the development of cocaine-induced sensitization. Given the postulated role of GLU in sensitization, it is suggested that NAALADase inhibitors may prevent behavioral adaptations which occur as a consequence of repeated cocaine administration.

In Vitro Assay of NAALADase Inhibitors on Cancer

Figure 18:
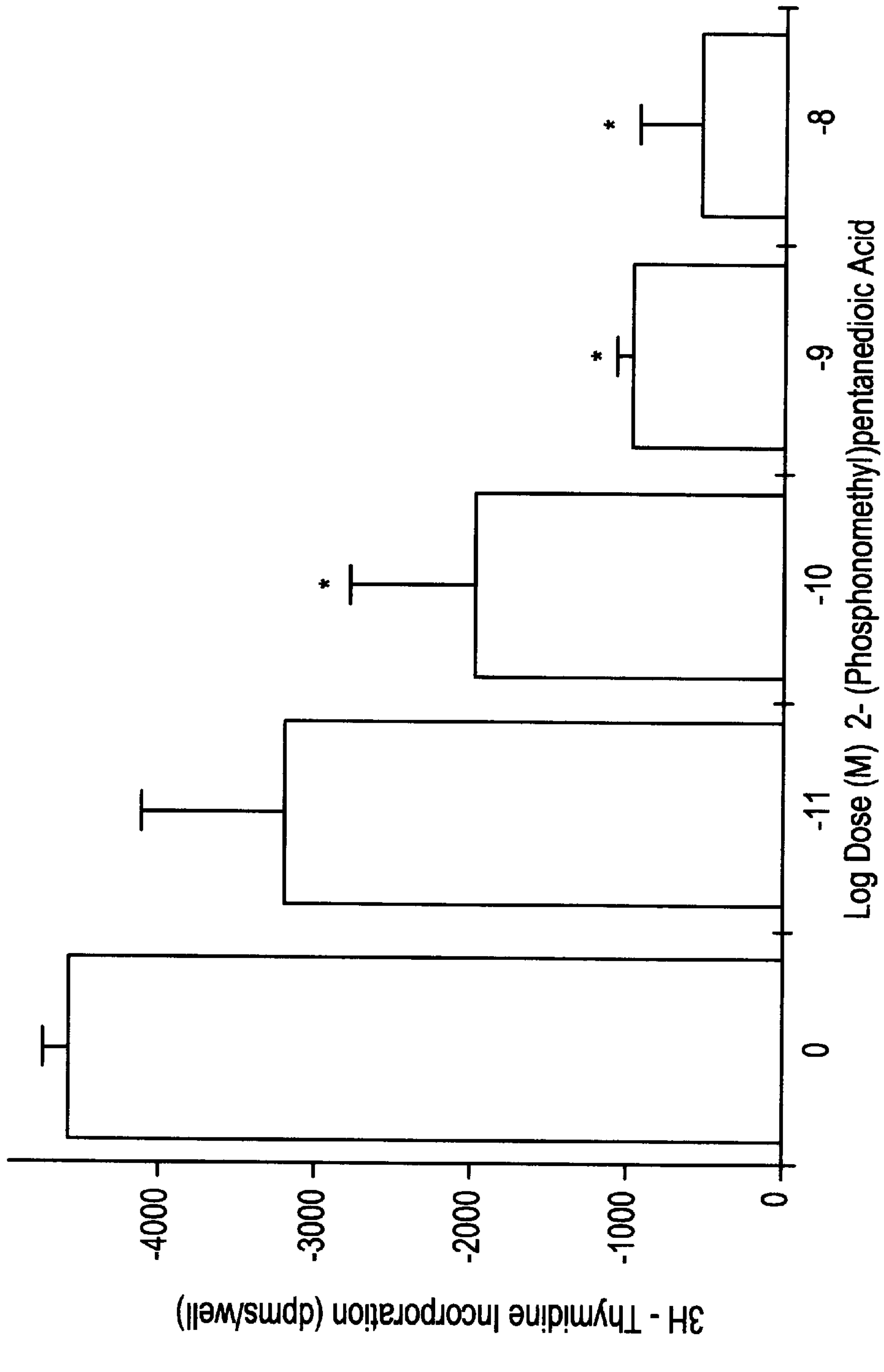
FIG. 18 is a bar graph plotting in vitro cancer cell growth against various doses of quisqualic acid with which LNCaP cells were treated.
Figure 19:
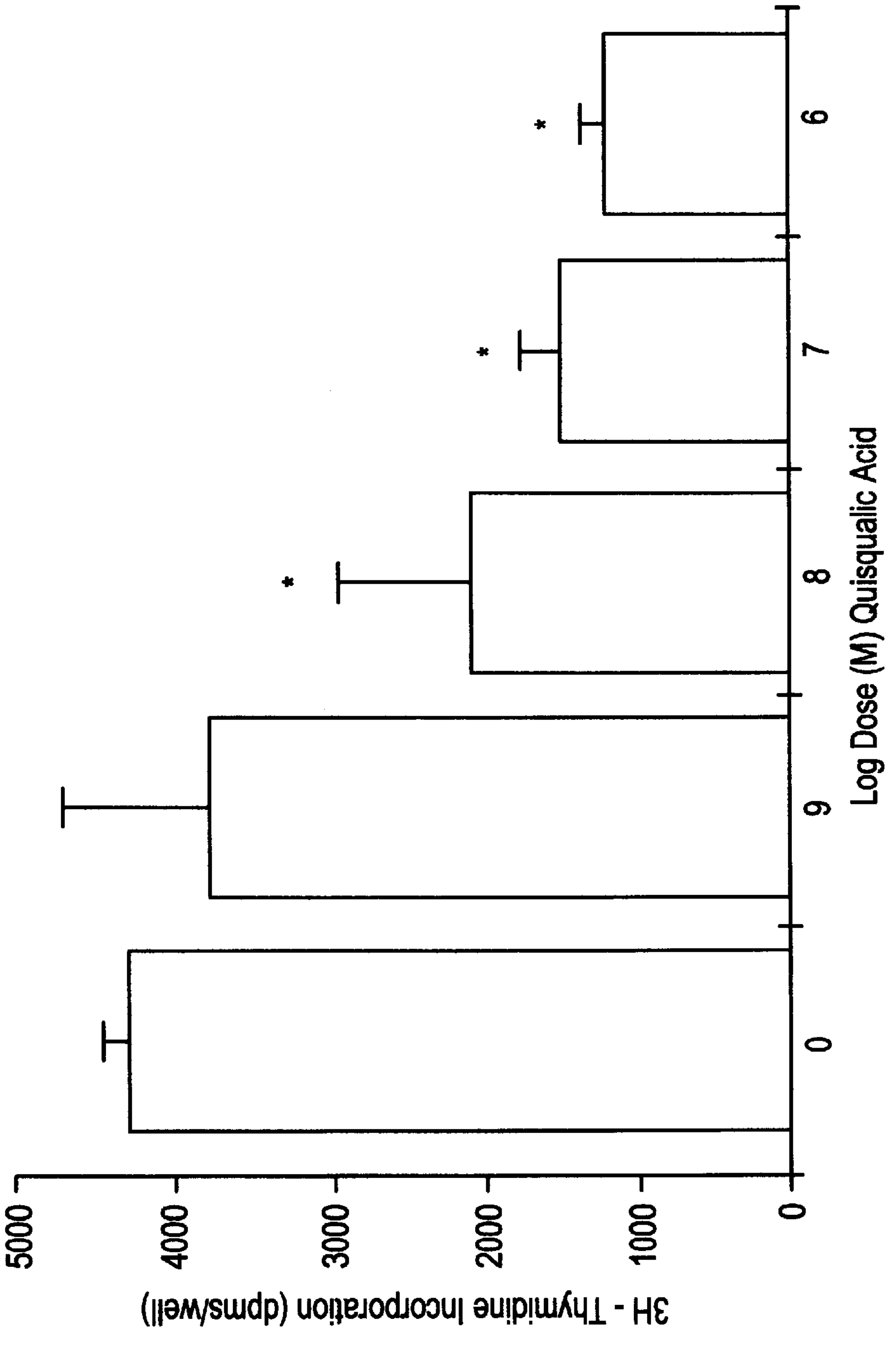
FIG. 19 is a bar graph plotting in vitro cancer cell growth against various doses of 2-(phosphonomethyl)-pentanedioic acid with which LNCaP cells were treated.

To examine the effect of NAALADase inhibitors on cancer cell line, LNCaP cells (a prostate cancer cell line) were treated with quisqualate acid (in concentrations ranging from 10 nM to 1 $\mu$M) and 2-(phosphonomethyl) pentanedioic acid (in concentrations ranging from 100 pM to 10 nM). The 3H-thymidine measurement for each concentration of quisqualate acid and 2-(phosphonomethyl) pentanedioic acid is provided in TABLE XIV below and graphically represented in FIG. 18 and FIG. 19, respectively.

TABLE XIV

| 3H-Thymidine Incorporation (dpm/well) | | |
|---|---|---|
| Dose | Quisqualic Acid | 2-(phosphonomethyl)-pentanedioic acid |
| Control | 4813 ± 572 | 4299 ± 887 |
| 10 pM | — | 3078 ± 1006 |
| 100 pM | — | 2062 ± 595 |
| 1 nM | 3668 ± 866 | 1001 ± 52 |
| 10 nM | 2137 ± 764 | 664 ± 366 |
| 100 nM | 1543 ± 312 | — |
| 1 μM | 1295 ± 181 | — |

The results show that LNCaP cell proliferation (as measured by the incorporation of 3H-thymidine) decreased significantly as the concentration of the NAALADase inhibitors increased, suggesting that the compounds of the present invention would be effective in treating cancer, particularly prostate cancer.

Protocol for In Vitro Cancer Assay

Cells in RPMI 1640 medium containing 10% Fetal Calf Serum (FCS) are plated in 24 well plates and allowed to adhere for 24 hours before addition of quisqualic acid ($10^{-9}$ to $10^{-6}$) or 2-(phosphonomethyl)pentanedioic acid ($10^{-11}$ to $10^{-8}$) for 7 days. On the 7th day, the cells are pulsed with 3H-thymidine for 4 hours, harvested and measured for radioactivity. Values represent means +/− SEM of 6 separate cell wells for each treatment. All experiments are performed at least twice.

To control for non-specific cytostatic effects of quisqualate acid and 2-(phosphonomethyl)pentanedioic acid, the agents are simultaneously evaluated on a non-NAALADase containing prostate cell line, DU145 (Carter et al., *Proc. Natl. Acad. Sci. USA*, (93) 749–753, 1996). If the treatments with quisqualate acid and 2-(phosphonomethyl) pentanedioic have no significant effect on cell growth, the NAALADase inhibiting activity of the agents are uniquely responsible for their cytostatic effects on prostate carcinoma cell lines.

Cell Lines and Tissue Culture

LNCaP cells are obtained from Dr. William Nelson at the Johns Hopkins School of Medicine in Baltimore, Md. DU145 cells are obtained from American Type Culture Collection (Rockville, Md.). Cells are grown in RPMI-1640 media supplemented with 5% heat-inactivated fetal calf serum, 2 mM-glutamine, 100 units/ml penicillin, and 100 μg/ml streptomycin (Paragon) in a humidified incubator at 37° C. in a 5% $CO_2$/95% air atmosphere.

[3H] Thymidine Incorporation Assays

The cells are suspended at $1\times10^{-3}$ cells/ml in RPMI-1640 media and seeded into 24-well plates at 500 μl per well. After 24 hour incubation, various concentrations of quisqualic acid (Sigma) or the potent NAALADase inhibitor 2-(phosphonomethyl)pentanedioic acid (synthesized according to the methods of Jackson et al., *J. Med. Chem.*, Vol. 39, No. 2, pp. 619–622, is added to the wells and the plates are returned to the incubator. On days 3, 5 and 7, media and drug are refreshed. On the 8th day following seeding, each well is pulsed with 1 μCi $^3$H-thymidine (New England Nuclear) for 4 hours. Media is then removed and the wells washed 2 times with phosphate buffered saline (pH=7.4). The contents of each well is subsequently solubilized 250 μl of 0.2 N NaOH and transferred to scintillation vials. 5 ml UltimaGold (Packard) scintillation cocktail is added and radioactivity is quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra are obtained using a Bruker spectrometer. Chemical shifts are reported in parts per million relative to tetramethylsilane as internal standard. Analytical thin-layer chromatography (TLC) is conducted on prelayered silica gel GHLF plates (Analtech, Newark, Del.). Visualization of the plates is accomplished by using UV light, phosphomolybdic acid-ethanol, and/or iodoplatinate charring. Flash chromatography is conducted on Kieselgel 60, 230–400 mesh (E. Merck, Darmstadt, West Germany). Solvents are either reagent or HPLC grade. Reactions are run at ambient temperature and under a nitrogen atmosphere unless otherwise noted. Solutions are evaporated under reduced pressure on a Buchi rotary evaporator.

In Vivo Assay of NAALADase Inhibitors on Cancer

To examine the effect of NAALADase inhibitors on cancer in vivo, ncr male mice injected with LNCaP cells and Copenhagan syngenic rats injected with Dunning G cells were administered subcutaneously and/or intratumorally with various doses of 2-(phosphonomethyl)-pentanedioic acid (Compound 3). The mean tumor volume ($mm^3$) and tumor:control ratio (% T/C) following treatment are graphically presented in FIGS. 20–24.

Figure 20:
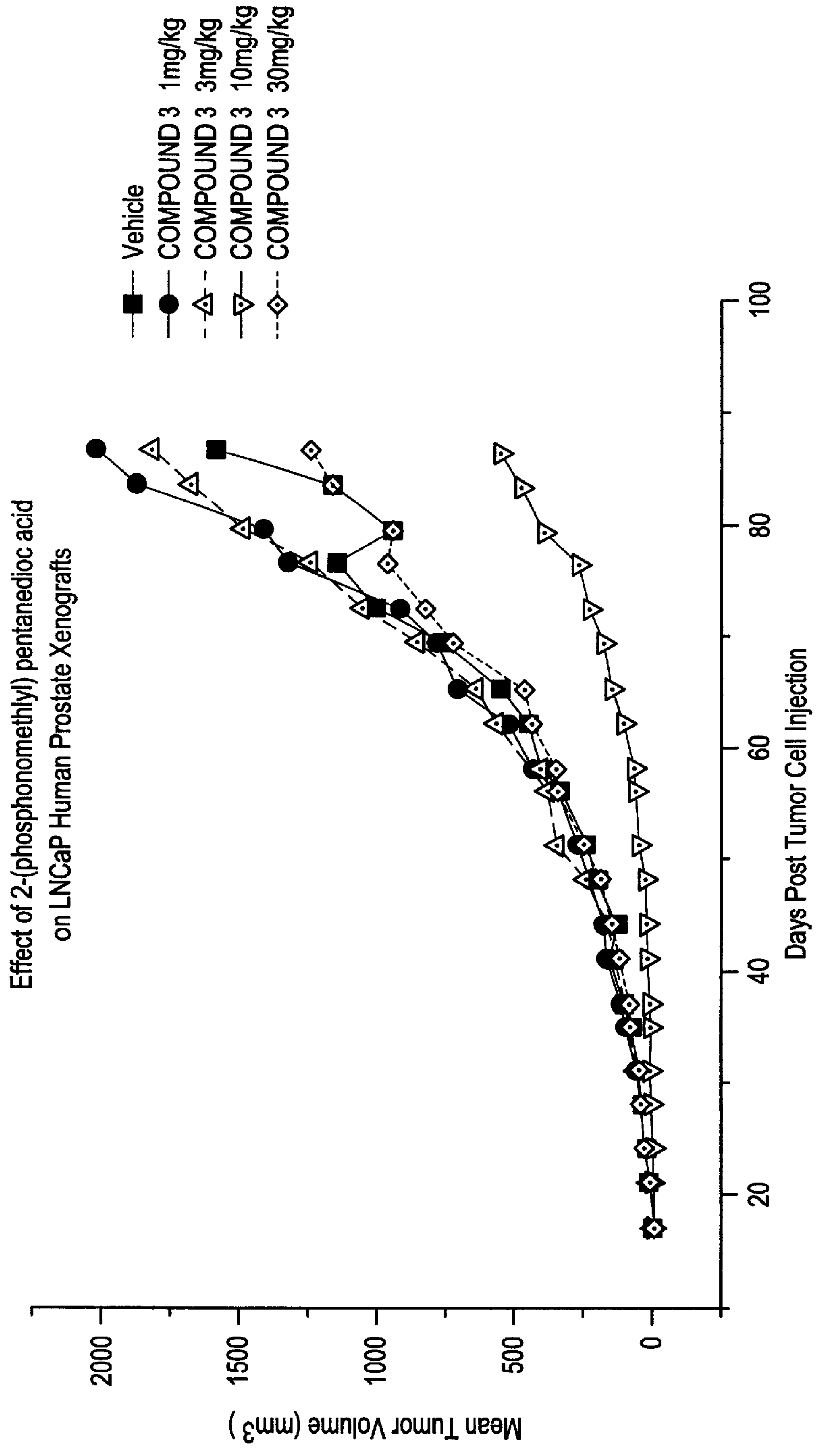
FIG. 20 is a graph plotting in vivo mean LNCaP tumor volume against the number of days following subcutaneous treatment with various doses of 2-(phosphonomethyl)-pentanedioic acid.
Figure 21:
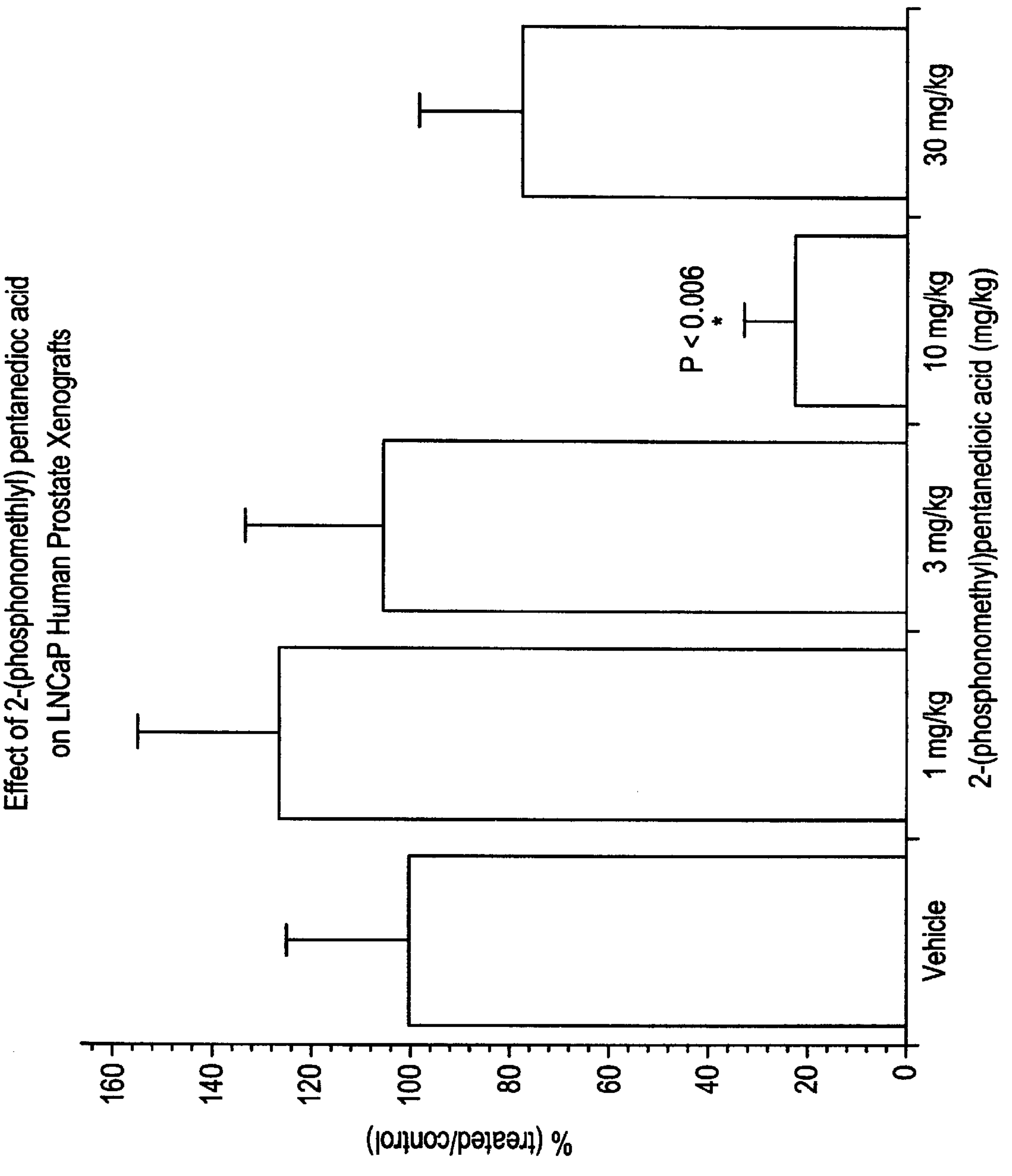
FIG. 21 is a bar graph plotting the tumor:control ratio in mice subcutaneously treated with a vehicle or 2-(phosphonomethyl)pentanedioic acid following injection with LNCaP cells.

The results show that LNCaP tumors responded to the subcutaneous treatment with Compound 3. The lower doses of 1 and 3 mg/kg and the highest dose of 30 mg/kg apparently had no effect on tumor growth (FIG. 20). The 10 mg/kg dose significantly inhibited tumor growth to 24% of controls at day 86 (p=0.006) (FIG. 21).

Figure 22:
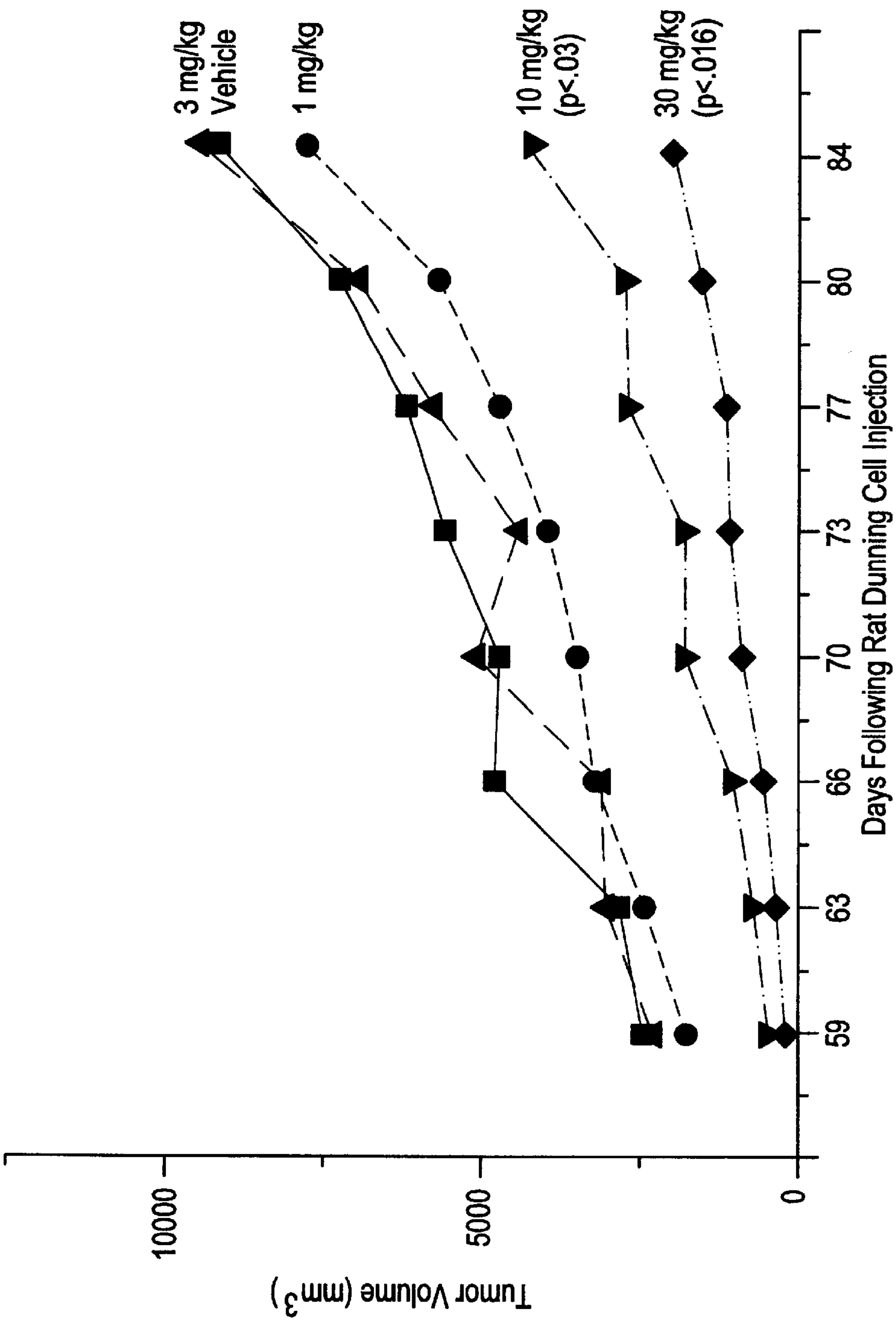
FIG. 22 is a graph plotting in vivo mean Dunning G tumor volume against the number of days following subcutaneous treatment with various doses of 2-(phosphonomethyl) pentanedioic acid.
Figure 23:
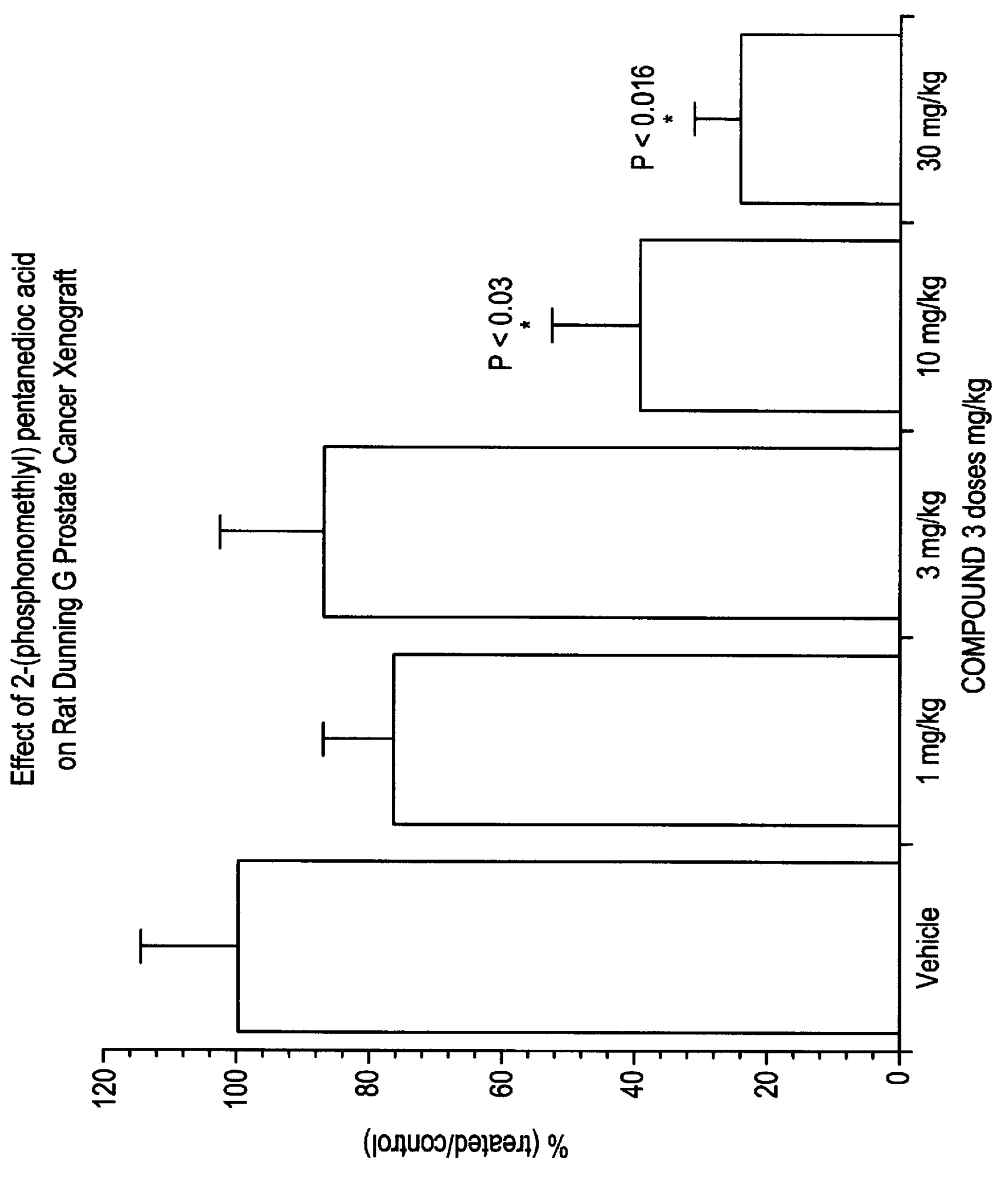
FIG. 23 is a bar graph plotting the tumor:control ratio in rats subcutaneously treated with a vehicle or 2-(phosphonomethyl)pentanedioic acid following injection with Dunning G cells.

The Dunning G tumors also responded to the subcutaneous treatment with Compound 3. The lower doses of 1 and 3 mg/kg had no effect on tumor growth while the two higher doses, 10 and 30 g/kg, significantly decreased tumor size (FIG. 22). The tumor size decreased to 38% of controls (p=0.03) at the 10 mg/kg dose and to 22% of controls at the 30 mg/kg dose (FIG. 23).

Figure 24:
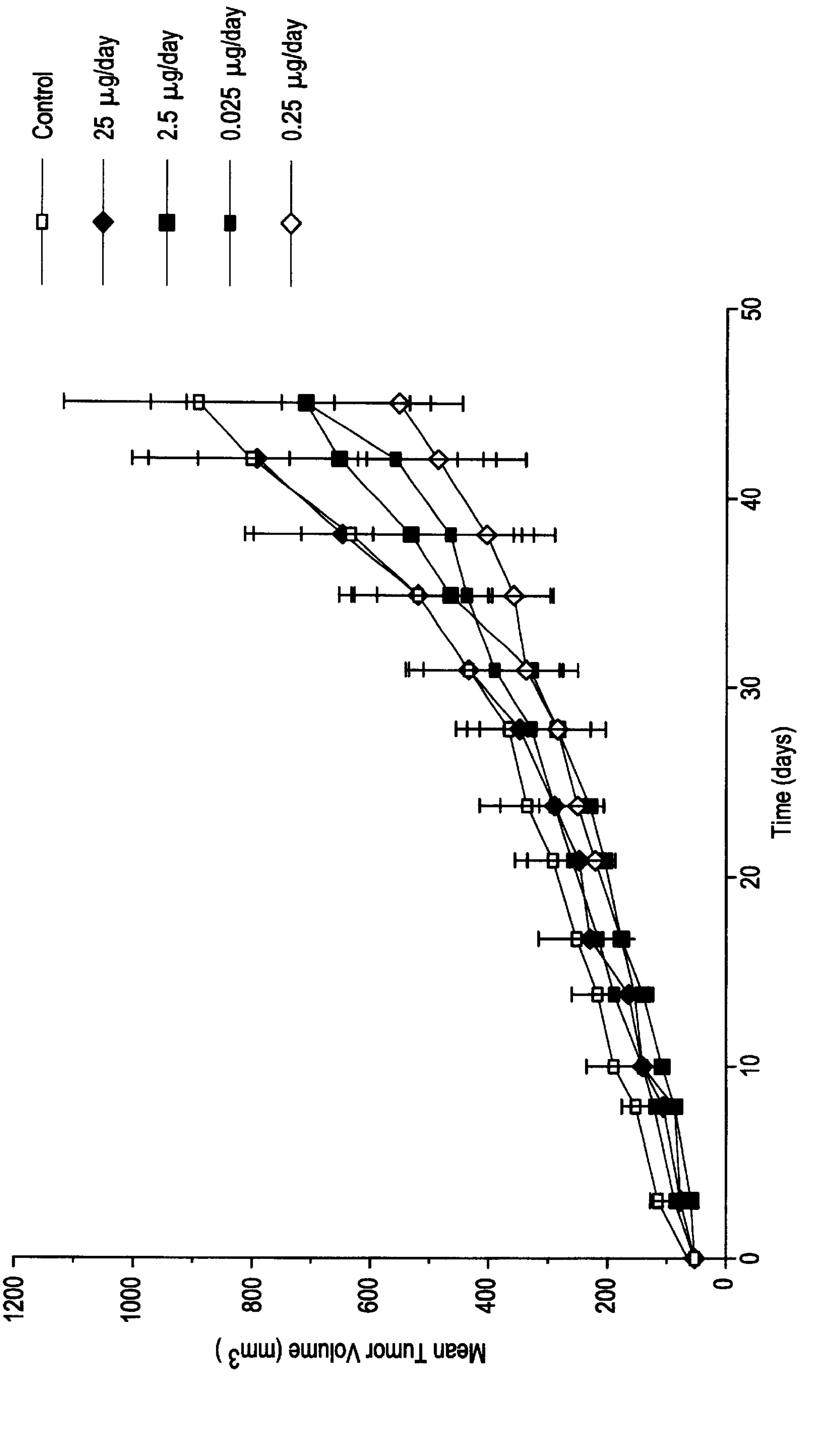
FIG. 24 is a graph plotting in vivo mean Dunning G tumor volume against the number of days following intratumoral treatment with various doses of 2-(phosphonomethyl) pentanedioic acid.

The LNCaP tumors also responded to the intratumoral treatment with Compound 3. The three lower dose levels (0.025, 0.25 and 2.5 μg/day) slowed tumor growth substantially though the greatest reduction was seen with the 0.025 μg/day dose (TABLE XV). Tumor volume after 42 days of treatment in the control group was 807.3±197.3 $mm^3$ compared with 465.7±176 $mm^3$ in the group treated with 0.025 μg/day (FIG. 24).

TABLE XV

| Antitumor Activity of 2-(Phosphonomethyl)pentanedioic Acid (Compound 3) | | |
|---|---|---|
| Treatment Group | Optimal % T/C | Regressions |
| Control | 100 | 0/7 |
| Intratumoral 2-(Phosphonomethyl)-pentanedioic Acid | | |
| 25.0 μg/day | 76 | 0/7 |
| 2.5 μg/day | 45 | 0/7 |
| 0.25 μg/day | 51 | 1/7 |
| 0.025 μg/day | 42 | 1/7 |

Protocol for In Vivo Cancer Assay

Subcutaneous Drug Delivery

LNCaP MODEL (Compound 3):

Ncr nude male mice, age 5 to 6 weeks, were injected in the right flank with $5\times10^6$ LNCaP cells in Matrigel™ (0.1 ml total injection volume). Two weeks following cell injection, daily subcutaneous (s.c.) injections of Compound 3 were initiated at the following doses: 1, 3, 10 and 30 mg/kg. Controls received 50 mM HEPES s.c. daily. Once tumors were palpable they were measured twice a week.

DUNNING G MODEL (Compound 3):

Male Copenhagen syngenic rats, age 8 to 10 weeks, were injected in both flanks with $10^7$ Dunning G cells. Two weeks following cell injection, daily s.c. injections of Compound 3 were initiated at the following doses: 1, 3, 10 and 30 mg/kg. Controls received 50 mM HEPES s.c. daily. Tumors were measured twice a week.

Intratumoral Drug Delivery:

LNCaP MODEL (Compound 3):

Ncr nude male mice, age 5 to 6 weeks, were injected in the right flank with $10^7$ LNCaP cells in Matrigel™ (0.1 ml total injection volume). When the tumors reached a predetermined size (50 to 60 $mm^3$), mice were randomly placed into treatment groups of 6 to 8 mice each. Compound 3 was administered intratumorally daily in a volume of 0.05 ml in the following doses: 25, 2.5, 0.25 and 0.025 μg. Controls received 50 μl of 50 mM HEPES intratumorally daily. Tumors were measured twice a week.

Response to treatment was monitored in two ways. First, mean tumor volume for each group was presented as tumor: control ratio (% T/C) and these values were compared at one point in time. Second, tumor volume versus time was monitored.

In Vivo Assay of Daily Dosages of NAALADase Inhibitors on Angiogenesis

C57B1 female mice age 8 to 10 weeks (5/group) were injected subcutaneously with 0.5 mL of Matrigel™, 150 ng/mL of the angiogenic factor basic FGF (bFGF) and with 0, 0.47 μM or 4.7 μM 2-(phosphonomethyl)pentanedioic acid (Compound 3). The injected Matrigel™ rapidly formed a gel. On the same a day as the Matrigel™ injection, daily subcutaneous injections of 2-(phosphonomethyl)-pentanedioic acid around the Matrigel™ plug were initiated. Seven days post Matrigel™ injection, Matrigel™ plugs were excised and histology was performed.

The concentrations of the daily dosages as well as the coinciding initial Matrigel™ plug compositions are provided below in TABLE XVI.

TABLE XVI

Concentrations of Daily Dosaqes of NAALADase Inhibitors

| Daily Subcutaneous Injection Concentration | Initial Concentrations in Matrigel ™ |
|---|---|
| Vehicle | 50 mM Hepes |
| 3 mg/kg | 0.47 μM Compound 3 in 50 mM Hepes |
| 30 mg/kg | 4.7 μM Compound 3 in 50 mM Hepes |

Figure 25A:
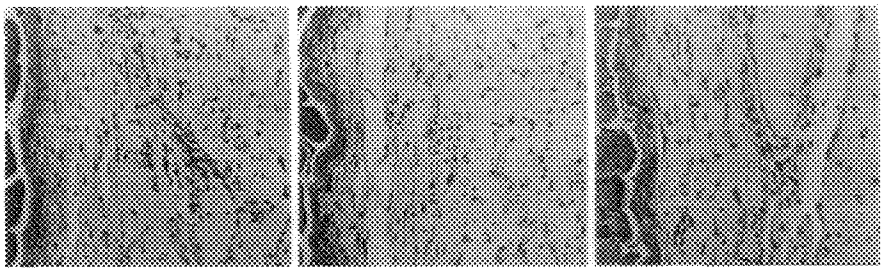
FIG. 25A is a set of microphotographs of Matrigel™ plugs subcutaneously injected into mice and treated with a vehicle alone following injection of an angiogenic factor.
Figure 25B:
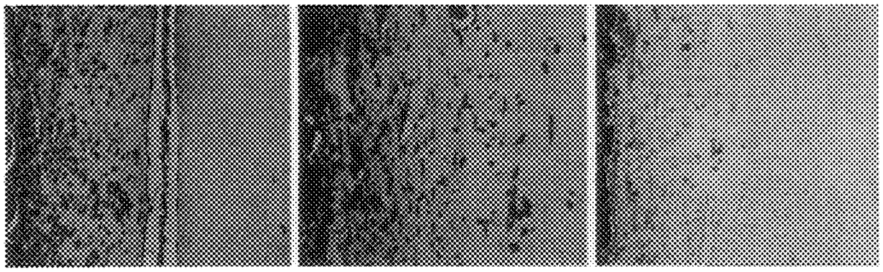
FIG. 25B is a set of microphotographs of Matrigel™ plugs subcutaneously injected into mice and treated with daily 3 mg/kg dosages of 2-(phosphonomethyl)pentanedioic acid following injection of an angiogenic factor.
Figure 25C:
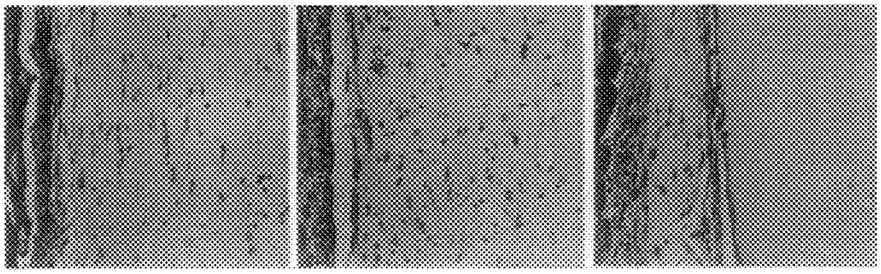
FIG. 25C is a set of microphotographs of Matrigel™ plugs subcutaneously injected into mice and treated with daily 30 mg/kg dosages of 2-(phosphonomethyl) pentanedioic acid following injection of an angiogenic factor.

As detailed in FIG. 25A, a good angiogenic response was observed in the vehicle dose group. The resultant decrease in blood vessels or angiogenesis in the Matrigel™ plugs from the 3 mg/kg and 30 mg/kg daily dose groups is shown in FIG. 25B and FIG. 25C, respectively.

In Vivo Assay of a Continuous Dosage of NAALADase Inhibitors on Angiogenesis

Miniosmotic pumps were implanted into C57B1 female mice (5/group) at the Compound 3 concentrations shown in TABLE XVII below. Minipumps filled with vehicle (50 mM Hepes) were also implanted at this time. Twenty-four hours later, mice were each injected subcutaneously with 0.5 mL Matrigel™ and the 150 ng/mL of the angiogenic factor, basic FGF (bFGF). Thirteen days post Matrigel™/bFGF injection, the gels were recovered, fixed in formalin and sections were stained with Trichrome-Masson stain.

TABLE XVII

Concentrations of Continuously Administered NAALADase Inhibitors

| Compound 3 Released by Minipump |
|---|
| 50 mM Hepes |
| 1 μg/day |
| 10 μg/day |
| 100 μg/day |

Figure 26:
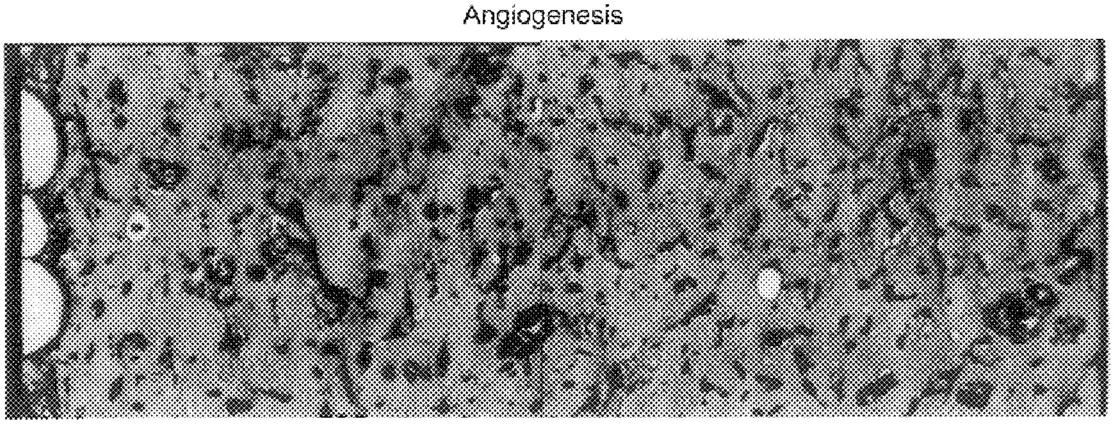
FIG. 26 is a microphotograph of a Matrigel™ plug subcutaneously injected into a mouse and treated with a continuous concentration dosage of a vehicle alone following injection of an angiogenic factor.
Figure 27:
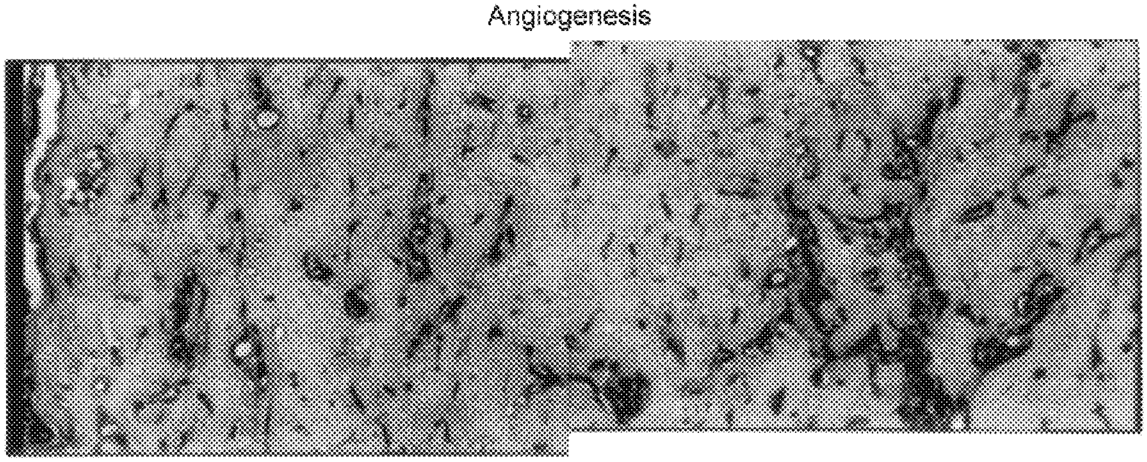
FIG. 27 is a microphotograph of a Matrigel™ plug subcutaneously injected into a mouse and treated with a 1 $\mu$g/day continuous dosage of 2-(phosphonomethyl)-pentanedioic acid following injection of an angiogenic factor.
Figure 28:
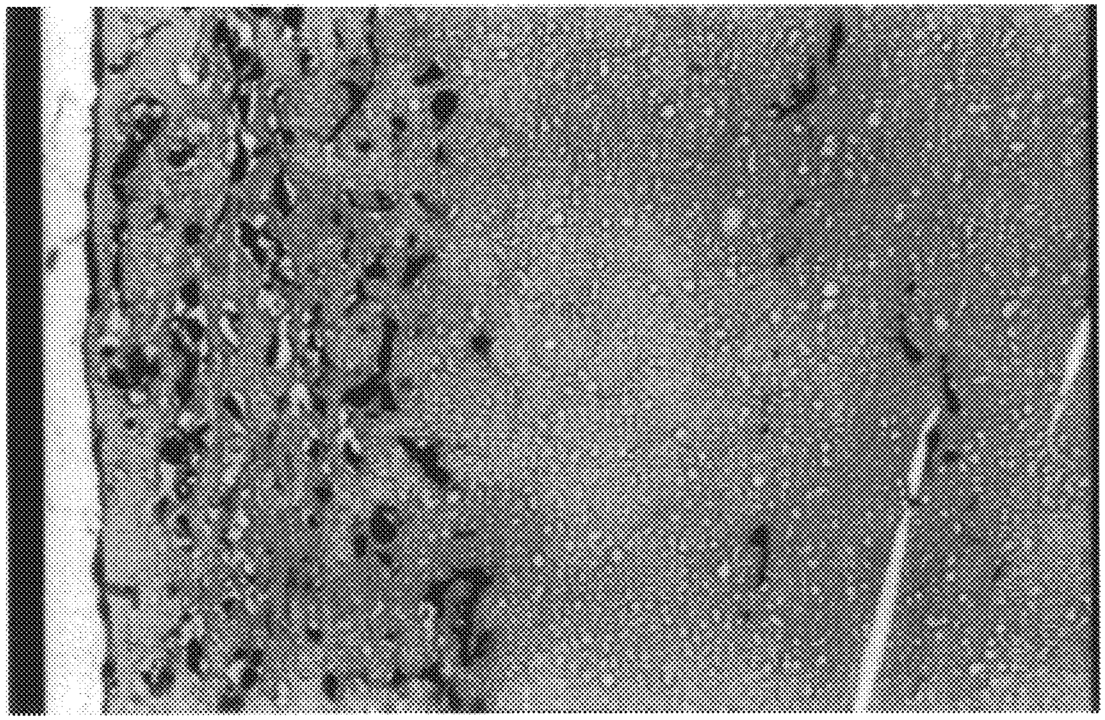
FIG. 28 is a microphotograph of a Matrigel™ plug subcutaneously injected into a mouse and treated with a 10 $\mu$g/day continuous dosage of 2-(phosphonomethyl) pentanedioic acid following injection of an angiogenic factor.
Figure 29:
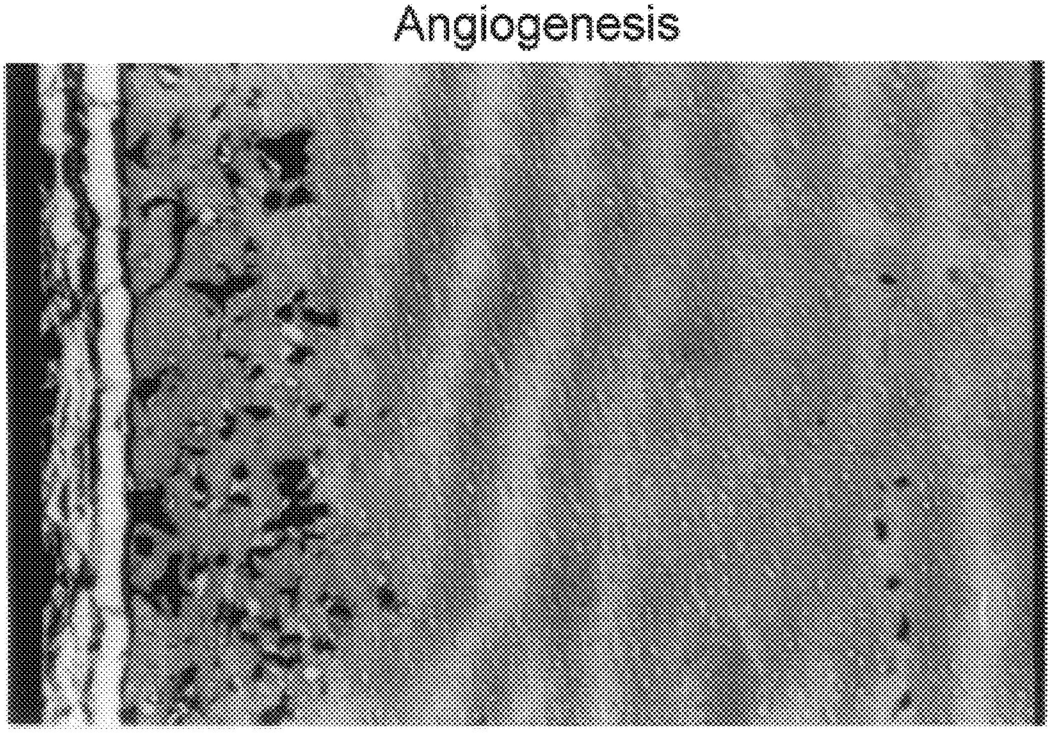
FIG. 29 is a microphotograph of a Matrigel™ plug subcutaneously injected into a mouse and treated with a 100 ag/day continuous dosage of 2-(phosphonomethyl) pentanedioic acid following injection of an angiogenic factor.

A strong angiogenic response was observed in the vehicle and 1 μg/day dose group, as shown in FIG. 26 and 27, respectively. As detailed in FIGS. 28 and 29, respectively, delivery of 10 μg/day and 100 μg/day of Compound 3 significantly decreased angiogenesis in the Matrigel™/bFGF gels.

In Vivo Assay of NAALADase Inhibitors on Diabetic Neuropathy

NAALADase inhibition in an in vivo streptozotocin (STZ)-induced peripheral diabetic neuropathy model was studied. Male Sprague-Dawley rats weighing 200–250 g were rendered diabetic by intravenous injection of 60 mg/kg STZ into the tail vein. Plasma glucose levels were determined 3 weeks after STZ administration. Only STZ-animals with plasma glucose levels >300 mg/dL (17 mM) were used in the study. Thermal pain threshold and withdrawal latency were used to assess the status of the small dorsal root ganglion (DRG) sensory neurons. Pain was monitored using the plantar test (Hargreaves' Method) using a Basile Plantar apparatus built by Ugo Basil, Vaarese, Italy.

Figure 31:
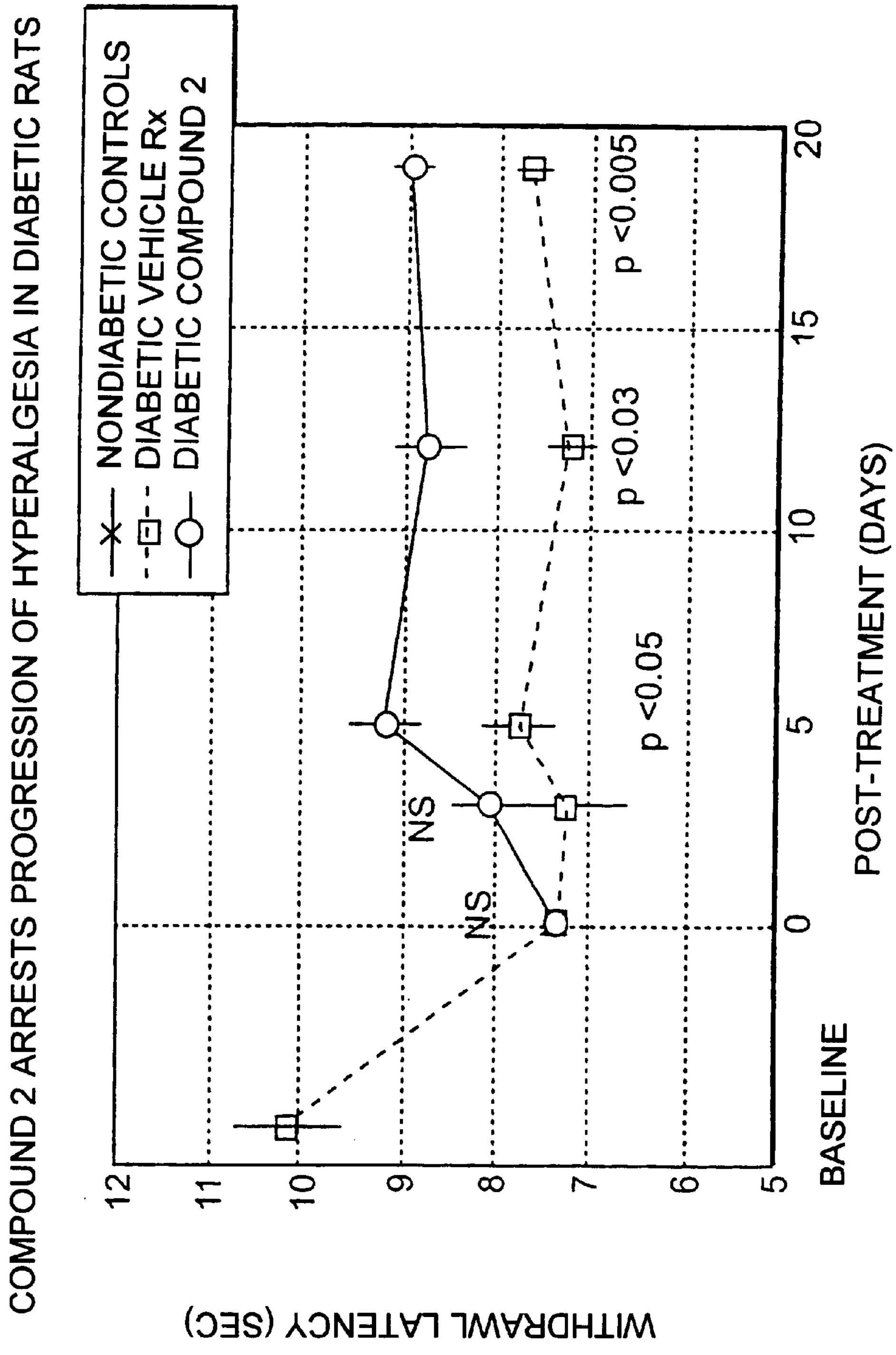
FIG. 31 is a graph plotting withdrawal latency of diabetic rats against the days following treatment with 2-[[(pentafluorobenzyl)hydroxyphosphinyl]methyl] pentanedioic acid.

At two months following the STZ administration, the diabetic animals were hyperalgesic as compared to non-diabetic controls as determined by their difference in withdrawal latency. At this time, the rats were administered either the NAALADase inhibitor 2-[[(pentafluorobenzyl) hydroxyphosphinyl]methyl]pentanedioic acid (50 mg/kg) or vehicle intraperitoneally once per day for 20 days. Thermal pain responses were measured at days 3, 5, 12 and 19 post-dosing. As depicted in FIG. 31, following 5 days of dosing, animals administered 2-[[(pentafluorobenzyl) hydroxyphosphinyl]methyl]pentanedioic acid showed a significant increase in their withdrawal latency compared to vehicle animals. This difference was maintained throughout the observation period.

These data suggest that NAALADase inhibitors protect against experimental diabetic sensory neuropathy and may be useful in the treatment of peripheral neuropathies.

Figure 32:
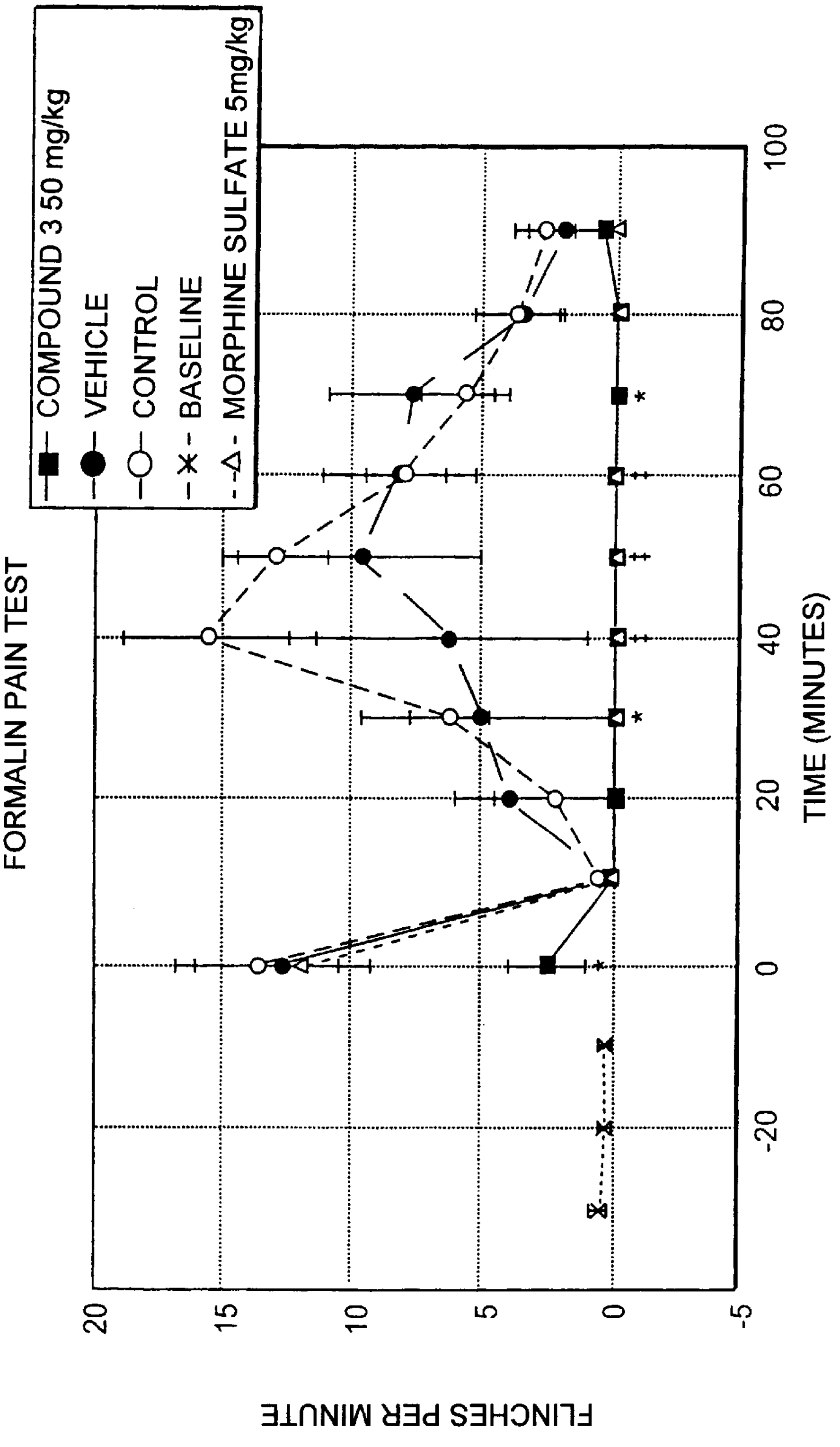
FIG. 32 is a graph plotting the formalin-induced flinching behavior of rats treated with a vehicle or 2-(phosphonomethyl)pentanedioic acid against the time following treatment.
Figure 33:
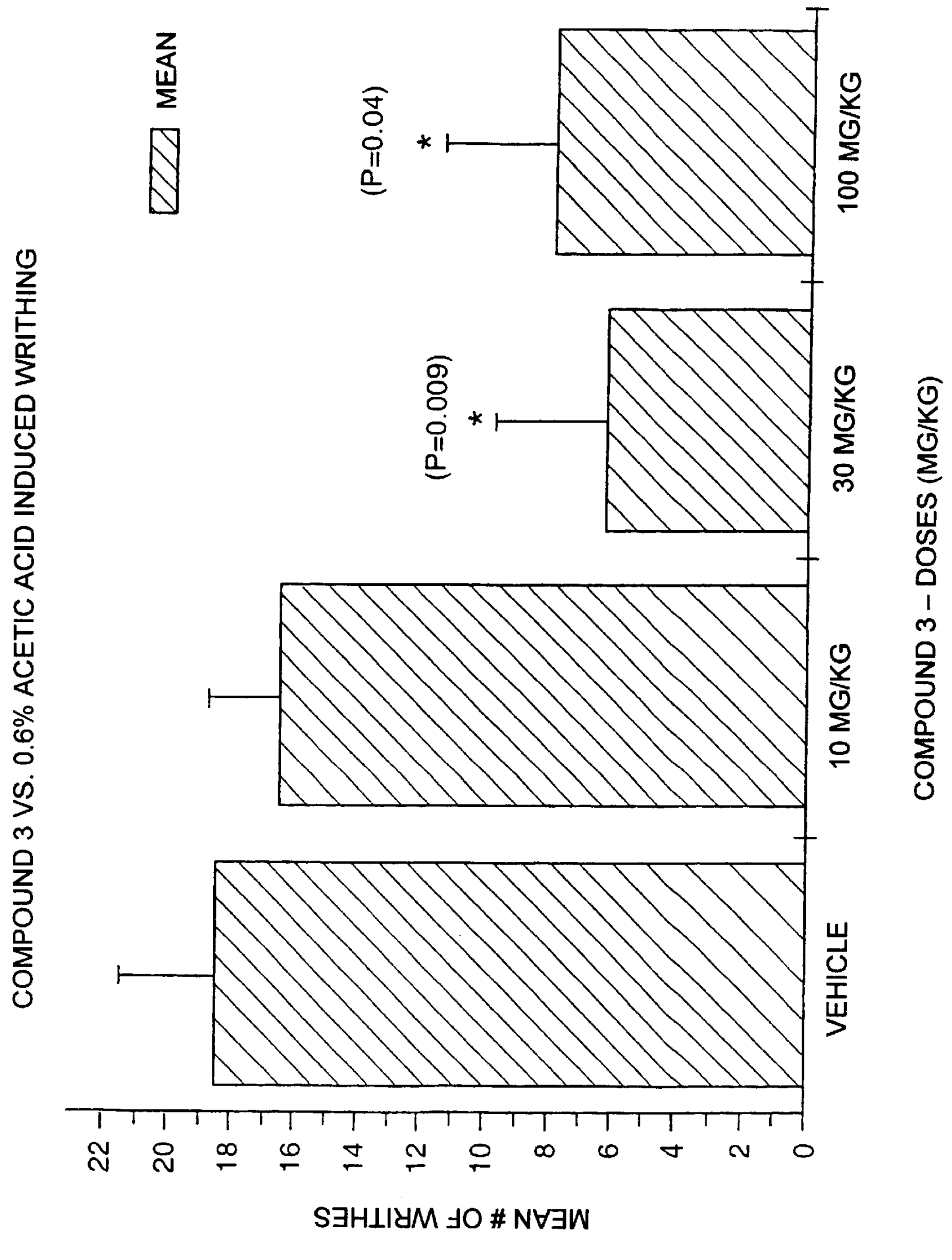
FIG. 33 is a bar graph plotting the acetic acid-induced writhing of rats against doses of a vehicle or 2-(phosphonomethyl)pentanedioic acid with which the rats were treated.
Figure 34:
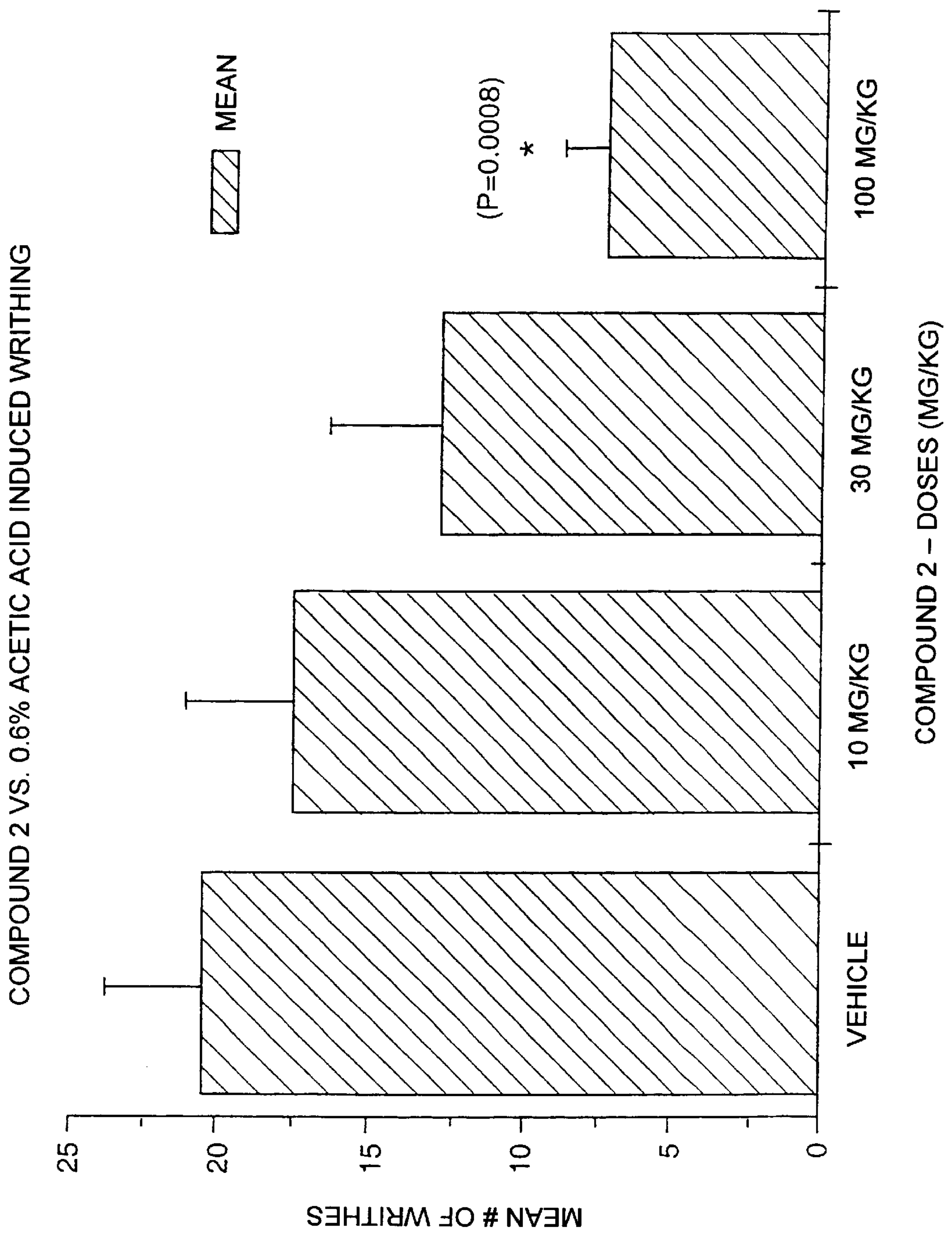
FIG. 34 is a bar graph plotting the acetic acid-induced writhing of rats against doses of a vehicle or 2-[[(pentafluorobenzyl)hydroxyphosphinyl]methyl] pentanedioic acid with which the rats were treated.
Figure 35:
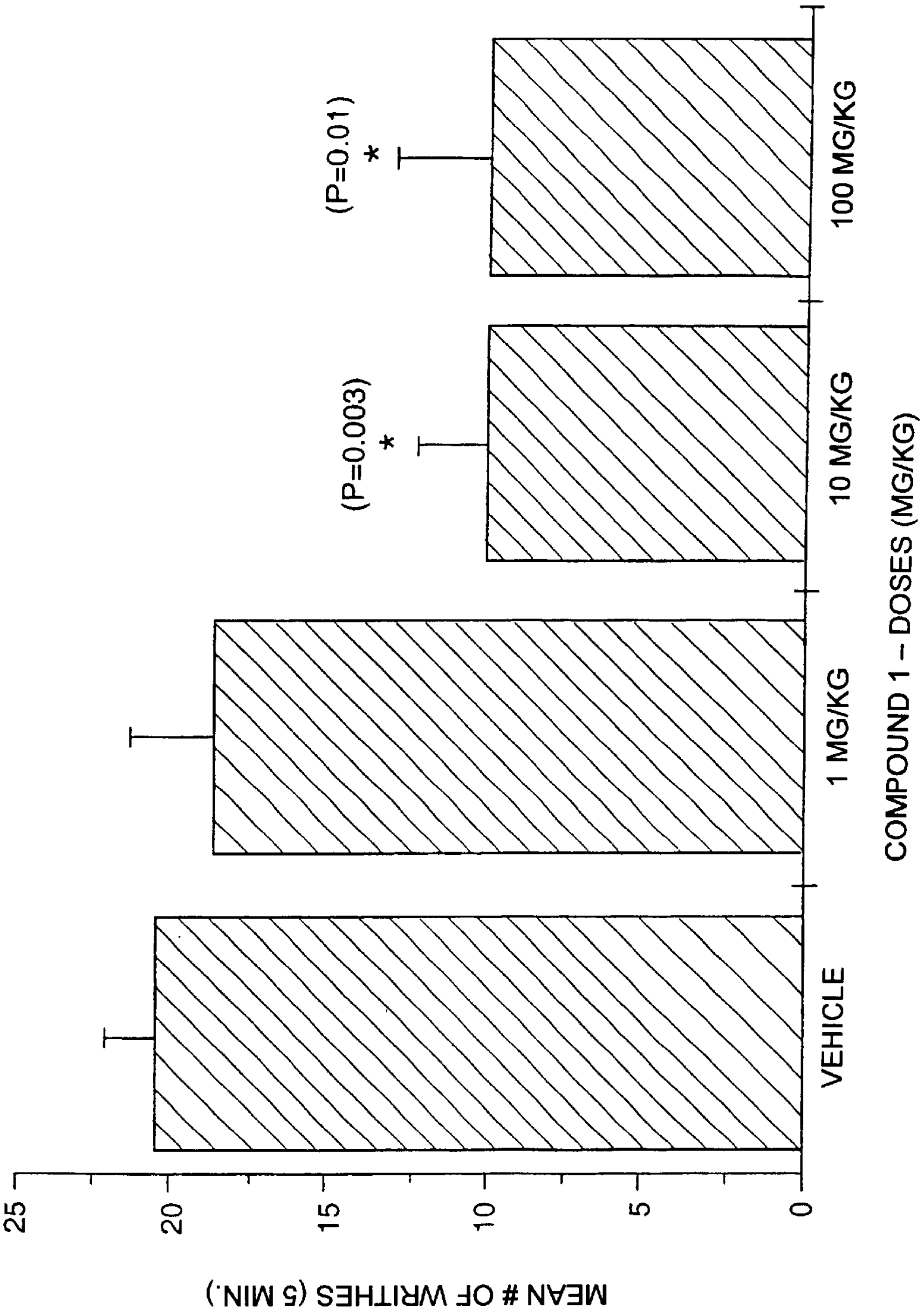
FIG. 35 is a bar graph plotting the acetic acid-induced writhing of rats against doses of a vehicle or 2-(2-sulfanylethyl)pentanedioic acid with which the rats were treated.
Figure 36:
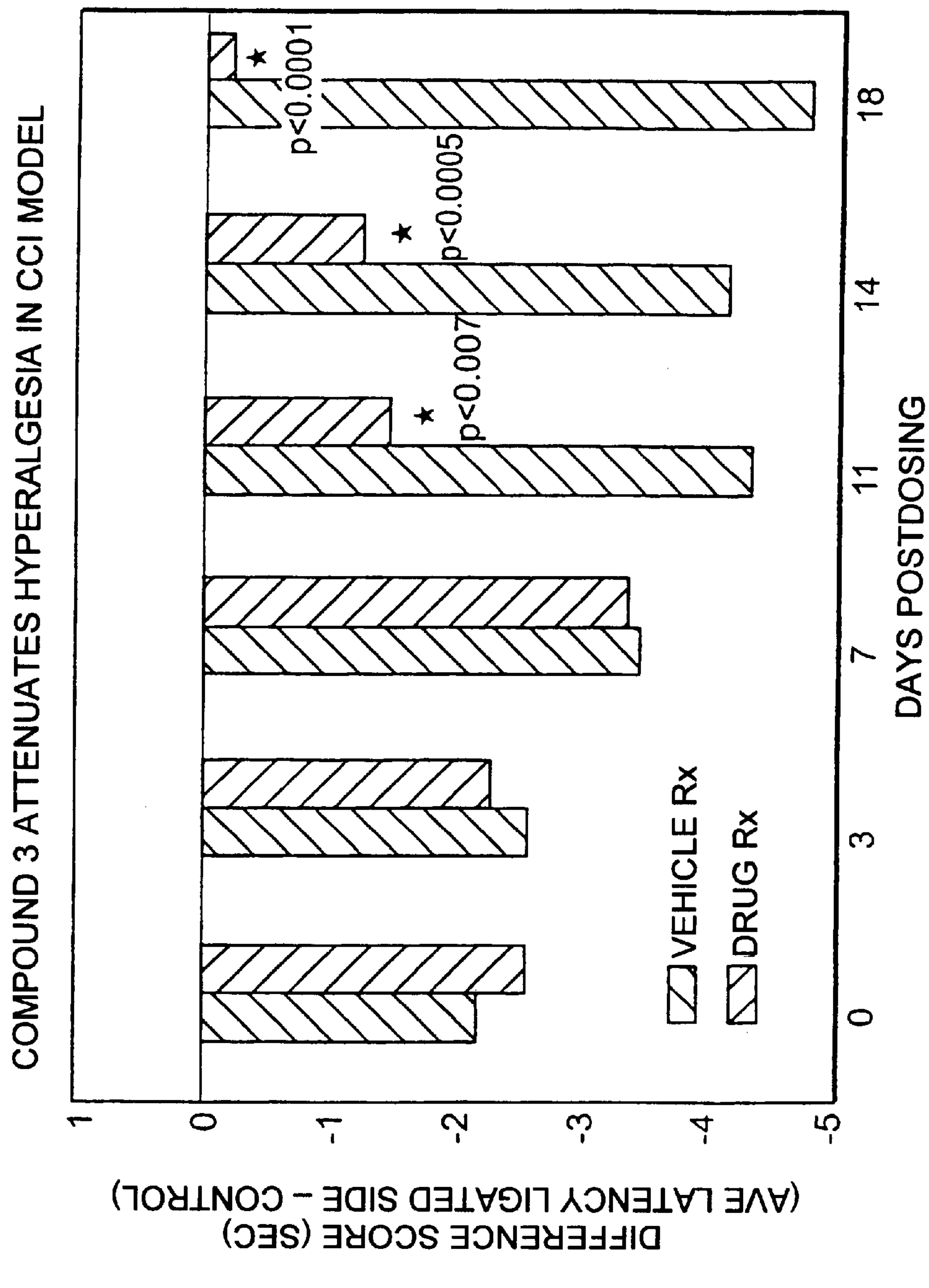
FIG. 36 is a bar graph plotting the chronic constrictive injury-induced hyperalgesia of rats treated a vehicle or 2-(phosphonomethyl)pentanedioic acid against the days postdosing.

In Vivo Assay of NAALADase Inhibitors on Hyperalgesia in Formalin, Acetic Acid, and Chronic Constricture Induced Models of Pain Recent evidence suggest that the excitatory amino acid glutamate plays a major role in both centrally and peripherally mediated nociception. One source of neuronal glutamate is thought to derive from the abundant neuropeptide NAAG which is hydrolyzed by NAALADase to liberate free glutamate. The inventors hypothesized that inhibition of NAALADase could limit pain by preventing this source of glutamate. To test this hypothesis, the inventors examined the possible antinocipetive effects of several NAALADase inhibitors in the formalin-, acetic acid- and chronic constrictive injury (CCI; "Bennett model") models of pain. In the formalin model, rats were dosed i.p. daily with 2-(phosphonomethyl)pentanedioic acid (50 mg/kg) or vehicle for 7 days. On day 7, 5% formalin was injected into the dorsum of the rat's hindpaw. The results are graphically presented in FIGS. 32–36. Pretreatment with 2-(phosphonomethyl)pentanedioic acid robustly attenuated the flinching behavior in both the early and late phases of the formalin model (13.8±6.4 reduced to 2.5±3, p=0.02 and 58.0±9.8 reduced to 0.5±0.58, p=0.0001, respectively; FIG. 32). The 2-(phosphonomethyl)pentanedioic acid treatment was more robust than acute pretreatment with morphine (5 mg/kg). In the acetic acid model of pain, acetic acid (0.6%) induced writhing was significantly attenuated in mice pretreated with 2-(phosphonomethyl)pentanedioic acid (FIG. 33), 2-(2-sulfanylethyl)pentanedioic acid (FIG. 34), 2-[[(pentafluorobenzyl)hydroxyphosphinyl]methyl] pentanedioic acid (FIG. 35), compared to vehicle control animals. Finally, in the CCI induced model of pain, animals were dosed i.p. daily with 2-(phosphonomethyl)-pentanedioic acid (50 mg/kg) starting 10 days after surgery for 18 days. 2-(phosphonomethyl)pentanedioic acid dramatically reduced the hyperalgesia following sciatic nerve constriction as determined by thermal pain response. On day 18, pain was 98% attenuated when compared to a similarly operated vehicle group of rats (difference scores of −0.2±1.9 vs. −4.75±2.4; p=0.0001; FIG. 36). These data suggest that inhibition of NAALADase may be a useful treatment modality for both acute and chronic pain.

EXAMPLES

The following examples are illustrative of the present invention and are not intended to be limitations thereon. Unless otherwise indicated, all percentages are based upon 100% by weight of the final composition.

Example 1

Synthesis of 2-(2-sulfanylethyl)pentanedioic acid 3-(2-Oxotetrahydro-3-thiophenyl)propanoate

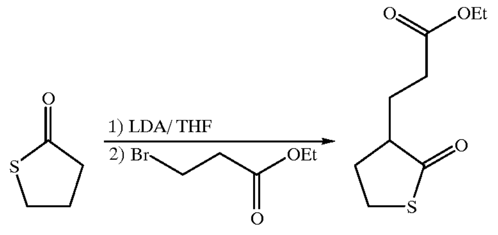

To a cooled solution (−78° C.) of lithium diisopropylamide (LDA) (98 mmol) in THF (100 ml) was added dropwise γ-thiobutyrolactone (10 g, 98 mmol).

After stirring for fifteen minutes, ethyl 3-bromopropanoate (35.4 g, 196 mmol) was added and the reaction allowed to warm to room temperature overnight. The solvent was removed under reduced pressure and the resulting residue was purified by column chromatography yielding 3 g (16%) of clear oil. $^1$H NMR ($CDCl_3$) δ 1.2 (t, 3H), 1.7 (m, 1H), 1.9 (m, 1H), 2.1 (m, 1H), 2.4 (t, 2H), 2.5 (m, 2H), 3.3 (t, 2H), 4.2 (q, 2H).

2-(2-sulfanylethyl)pentanedioic acid

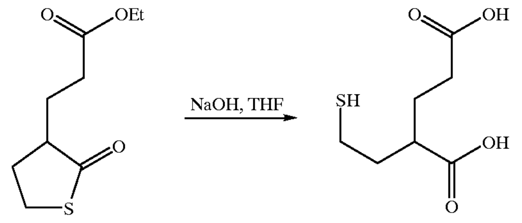

To a solution of ethyl 3-(2-oxotetrahydro-3-thiophenyl) propanoate (0.77 g, 3.81 mmol) in THF (5 ml) was added sodium hydroxide (1 M in water, 5 ml). The mixture was allowed to stir for two days, then the THF was removed under reduced pressure, the aqueous layer was washed with ether, then acidified to pH 1 with HCl and extracted with ethyl acetate. The combined ethyl acetate extracts were dried over magnesium sulfate and the solvent was removed under reduced pressure. The resulting residue was purified by column chromatography yielding a 150 mg of clear oil (20%). $^1$H NMR (d6-DMSO) δ 1.7 (m, 3H), 1.8 (m, 1H), 2.2 (m, 2H), 2.3–2.5 (m, 4H). Analysis calculated for $C_7H_{12}SO_4$: C, 43.74; H, 6.29; S, 16.68. Found: C, 43.61; H, 6.39; S, 16.55.

Example 2

Synthesis of 2-(3-sulfanylpropyl)pentanedioic acid
Scheme VII 2,2-dimethyl-5-[3-[(triphenylmethyl)thio]propyl]-1,3-dioxane-4,6-dione (I)

20 mmol of 3-[(triphenylmethyl)thio]propionic acid (6.9 g) was dissolved with 22 mmol Meldrum's acid (2,2-dimethyl-1,3-dioxane-4,6-dione)(3.2 g) and 31 mmol 4-dimethylaminopyridine (3.85 g) in 100 ml $CH_2Cl_2$. The reaction mixture was cooled to −5° C. and a solution of 22 mmol of dicyclohexyl carbodiimide (4.74 g) in 50 ml $CH_2Cl_2$ was added dropwise over 1 hour. The mixture was left at <0° C. temperature overnight, during which time tiny crystals of dicyclohexylurea precipitated. After filtration, the reaction mixture was washed 4× with 10% $KHSO_4$, 1× with brine and dried with $MgSO_4$ for 2 hours. This solution was used for the second step without characterization or further purification.

The solution from the previous reaction was cooled to −5° C. and 13.3 ml (220 mmol) of 98% acetic acid was added. Then 1.85 g (50 mmol) of $NaBH_4$, was added in small portions while stirring over 1 hour. The reaction mixture was left in the refrigerator overnight and then washed 3× with water and 2× with brine. Organic phase was dried with $MgSO_{41}$ filtered and evaporated to dryness. The residue was dissolved in EtOAc, the precipitated small amount of dicyclohexylurea was filtered off and filtrate was brought to crystallization by addition of hexane. Yield 7.5 g of 2,2-dimethyl-5-[3-[(triphenylmethyl)thio]propyl]-1,3-dioxane-4,6-dione (I) (86%-two steps). $_{13}$C-NMR δ 20.0(q), 26.2(q), 27.2(t), 28.9(t), 32.0(t), 46.2(d), 67.0(s), 105.3(s), 127.0(d), 128.3(d), 130.0(d), 145.2(s), 165.6(s).

2,2-Dimethyl-4,6-dioxo-5-[3-[(triphenylmethyl)thio] propyl]-1,3-dioxane-5-propanoic acid methylester (II)

5 mmol of 2,2-dimethyl-5-[3-[(triphenylmethyl)thio] propyl]-1,3-dioxane-5-propanoic-4,6-dione (I) (2.3 g), was dissolved with 20 mmol methyl-3-bromopropionate (3.34 g=2.18 ml) and 4.6 ml of 4.37 M methanolic solution of sodium methoxide (20 mmol) in 10 ml of methanol. The reaction mixture was heated to 60° C. overnight after which TLC in hexane/ethylacetate 1:1 detected no starting material. The mixture was then evaporated to dryness and mixed with 40 ml of aqueous 10% $KHSO_4$. The organic material was extracted by 3 portions of EtOAc, the organic layers were combined dried with $MgSO_4$ and evaporated. The residue was crystallized from hexane/ethylacetate to yield 2.1 g (77%) of 2,2-dimethyl-4,6-dioxo-5-[3-[(triphenylmethyl)thio]propyl]-1,3-dioxane-5-propanoic acid methyl ester (II), $^{13}C$-NMR ($CDCl_3$) δ 24.6, 29.4, 29.5, 29.6, 31.4, 32.6, 37.7, 51.9, 52.8, 66.8, 105.7, 126.7, 127.9, 129.5, 144.7, 168.4, 172.0.

6-(triphenylmethyl)thiol-1,3,3-hexanetricarboxylic acid (III)

2.56 mmol of 2,2-dimethyl-4,6-dioxo-5-[3-[(triphenylmethyl)thio]propyl]-1,3-dioxane-5-propanoic acid methyl ester (II) (1.4 g) with 18 mmol of sodium hydroxide (0.72 g) was dissolved in a mixture of 5 ml of 1,4-dioxane and 5 ml of water. The mixture was then heated to 100° C. for 1 hour, evaporated to dryness, dissolved in water and precipitated by addition of 1 M sulfuric acid. The precipitate was filtered off, washed with water and dried in a dessicator. Yield 1.36 g of 6-[(triphenylmethyl)thio]-1,3,3-hexanetricarboxylic acid (III) (~100%), $^{13}C$-NMR (MeOH) δ 25.4, 29.2, 30.7, 33.5, 33.7, 58.0, 68.3, 128.1, 129.3, 131.2, 146.7, 174.9, 176.9.

6-[(triphenylmethyl)thio]-1,3-hexanedicarboxylic acid (IV)

2.56 mmol of 6-[(triphenylmethyl)thio]-1,3,3,-hexanetricarboxylic acid (III) (1.36 g) was dissolved in 5 ml of dimethylsulfoxide and the solution was heated to 100° C. for 1 hour, evaporated to dryness, dissolved in water and precipitated by addition of 1 M sulfuric acid. The precipitated oil solidified after 1 hour treatment in an ultrasound bath. The solid was filtered off, washed with water and dried in a dessicator. Yield 1.1 g of 6-[(triphenylmethyl)thio]-1,3-hexanedicarboxylic acid (IV) (89% two steps from II), $^{13}C$-NMR (MeOH) δ 27.9, 28.6, 33.0 (two carbons), 33.1, 45.9, 68.1, 128.1, 129.2, 131.2, 146.8, 177.1, 179.4.

2-(3-sulfanylpropyl)pentanedioic acid (V)

2.46 mmol of 6-[(triphenylmethyl)thio]-1,3-hexanedicarboxylic acid (IV) (1.1 g) with 5 mmol triisopropylsilane (0.79 g) was dissolved in a mixture of 3 ml $CH_2Cl_2$/3 ml trifluoroacetic acid and left to stand at room temperature for 1 hour. The mixture was then evaporated to dryness and washed 3× with hexane. The remaining oily residue was dissolved in water, filtered and lyophilized to yield 0.35 g of 2-(3-sulfanylpropyl)pentanedioic acid (V) (76%), $^{13}C$-NMR (MeOH) δ 25.2(t), 28.8(t), 32.4(t), 33.0(t), 33.2(t), 45.9(d), 177.2(s), 179.6(s).

Example 3

Synthesis of 2-(4-sulfanylbutyl)pentanedioic acid 2-(4-sulfanylbutyl)pentanedioic acid was prepared using the methods described above for 2-(3-sulfanylpropyl) pentanedioic acid.

$^{13}C$-NMR (MeOH) δ 25.1(t), 27.4(t), 28.8(t), 33.0(t), 33.2(t), 35.4(t), 46.3(d), 177.2(s), 179.7(s).

Example 4

Synthesis of 2-(3-sulfanyl-2-methylpropyl) pentanedioic acid 2-(3-sulfanyl-2-methylpropyl)pentanedioic acid (mixture of two diastereoisomers) was prepared using the methods described above for 2-(3-sulfanylpropyl)pentanedioic acid.

$^{13}C$-NMR (MeOH) δ 18.9(q), 19.5(q), 29.1(t), 29.6(t), 31.7(t), 32.6(t), 32.9(t), 33.0(t), 35.5(d), 35.9(d), 39.2(t), 39.7(t), 44.2(d), 44.3(d), 177.0(s), 177.1(s), 179.7(s), 179.9 (s).

Example 5

A patient is at risk of injury from an ischemic event. The patient may be pretreated with an effective amount of a compound or a pharmaceutical composition of the present invention. It is expected that after the pretreatment, the patient would be protected from any injury due to the ischemic event.

Example 6

A patient is suffering from an ischemic event. The patient may be administered during or after the event, an effective amount of a compound or a pharmaceutical composition of the present invention. It is expected that after the treatment, the patient would recover or would not suffer any significant injury due to the ischemic event.

Example 7

A patient has suffered injury from an ischemic event. The patient may be administered an effective amount of a compound or a pharmaceutical composition of the present invention. It is expected that after the treatment, the patient would recover from the injury due to the ischemic event.

Example 8

A patient is suffering from a glutamate abnormality. The patient may then be administered an effective amount of a compound or a pharmaceutical composition of the present invention. It is expected that after the treatment, the patient would be protected from further injury due to the glutamate abnormality or would recover from the glutamate abnormality.

Example 9

A patient is suffering from or has suffered from a nervous insult, such as that arising from a neurodegenerative disease or a neurodegenerative process. The patient may then be administered an effective amount of a compound or a pharmaceutical composition of the present invention. It is expected that after the treatment, the patient would be protected from further injury due to the nervous insult or would recover from the nervous insult.

Example 10

A patient is suffering from Parkinson's disease. The patient may then be administered an effective amount of a compound or a pharmaceutical composition of the present invention. It is expected that after the treatment, the patient would be protected from further neurodegeneration or would recover from Parkinson's disease.

Example 11

A patient is suffering from ALS. The patient may then be administered an effective amount of a compound or a pharmaceutical composition of the present invention. It is expected that after the treatment, the patient would be protected from further neurodegeneration or would recover from ALS.

Example 12

A patient is suffering from epilepsy. The patient may then be administered an effective amount of a compound or a pharmaceutical composition of the present invention. It is expected that after the treatment, the patient would be protected from further neurodegeneration or would recover from epilepsy.

Example 13

A patient is suffering from abnormalities in myelination/demyelination processes. The patient may then be administered an effective amount of a compound or a pharmaceutical composition of the present invention. It is expected that after the treatment, the patient would be protected from further neurodegeneration or would recover from the abnormalities in myelination/demyelination processes.

Example 14

A patient is suffering from or has suffered from a cerebrovascular accident, such as stroke. The patient may then be administered an effective amount of a compound or a pharmaceutical composition of the present invention. It is expected that after the treatment, the patient would be protected from or would recover from any injury due to the cerebrovascular accident.

Example 15

A patient is suffering from a head trauma. The patient may then be administered an effective amount of a compound or a pharmaceutical composition of the present invention. It is expected that after the treatment, the patient would be protected from or would recover from any ischemic brain, spinal or peripheral injury resulting from the head trauma.

Example 16

A patient is suffering from a spinal trauma. The patient may then be administered an effective amount of a compound or a pharmaceutical composition of the present invention. It is expected that after the treatment, the patient would be protected from or would recover from any ischemic injury resulting from the spinal trauma.

Example 17

A patient is about to undergo surgery. The patient may be administered an effective amount of a compound or a pharmaceutical composition of the present invention. It is expected that after the treatment, the patient would not develop any ischemic brain, spinal or peripheral injury resulting from or associated with the surgery.

Example 18

A patient is suffering from focal ischemia, such as that associated with thromboembolytic occlusion of a cerebral vessel, traumatic head injury, edema or brain tumors. The patient may then be administered an effective amount of a compound or a pharmaceutical composition of the present invention. It is expected that after the treatment, the patient would be protected from or would recover from any brain, spinal or peripheral injury resulting from the focal ischemia.

Example 19

A patient is suffering from global ischemia. The patient may then be administered an effective amount of a compound or a pharmaceutical composition of the present invention. It is expected that after the treatment, the patient would be protected from or would recover from any brain, spinal or peripheral injury resulting from the global ischemia.

Example 20

A patient is suffering from a cardiac arrest. The patient may then be administered an effective amount of a compound or a pharmaceutical composition of the present invention. It is expected that after the treatment, the patient would be protected from or would recover from any ischemic brain, spinal or peripheral injury associated with the cardiac arrest.

Example 21

A patient is suffering from hypoxia, asphyxia or perinatal asphyxia. The patient may then be administered an effective amount of a compound or a pharmaceutical composition of the present invention. It is expected that after the treatment, the patient would be protected from or would recover from any ischemic brain, spinal or peripheral injury associated with the hypoxia, asphyxia or perinatal asphyxia.

Example 22

A patient is suffering from a cerebro-cortical injury. The patient may then be administered an effective amount of a compound or a pharmaceutical composition of the present invention. It is expected that after the treatment, the patient would be protected from or would recover from any ischemic brain injury resulting from the cerebro-cortical injury.

Example 23

The patient is suffering from an injury to the caudate nucleus. The patient may then be administered an effective amount of a compound or a pharmaceutical composition of the present invention. It is expected that after the treatment, the patient would be protected from or would recover from any ischemic brain injury resulting from the injury to the caudate nucleus.

Example 24

A patient is suffering from a cortical injury due to a condition identified in these examples. The patient may then be administered an effective amount of a compound or a pharmaceutical composition of the present invention. It is expected that after the treatment, the patient would be protected from further injury, or would exhibit at least 65% to at least 80% recovery from the cortical injury.

Example 25

A patient is suffering from multiple sclerosis. The patient may then be administered an effective amount of a compound or a pharmaceutical composition of the present invention. It is expected that after the treatment, the patient would be protected from further demyelination or would recover from multiple sclerosis.

Example 26

A patient is suffering from a peripheral neuropathy caused by Guillain-Barre syndrome. The patient may then be administered an effective amount of a compound or a pharmaceutical composition of the present invention. It is expected that after the treatment, the patient would be protected from further demyelination or would recover from the peripheral neuropathy.

Example 27

The patient is suffering from alcoholism. The patient may then be administered an effective amount of a compound or a pharmaceutical composition of the present invention. It is expected that after the treatment, the patient's craving for alcohol would be suppressed.

Example 28

A patient is suffering from nicotine dependence. The patient may then be administered an effective amount of a compound or a pharmaceutical composition of the present invention. It is expected that after the treatment, the patient's craving for nicotine would be suppressed.

Example 29

The patient is suffering from cocaine dependence. The patient may then be administered an effective amount of a compound or a pharmaceutical composition of the present invention. It is expected that after the treatment, the patient's craving for cocaine would be suppressed.

Example 30

A patient is suffering from heroine dependence. The patient may then be administered an effective amount of a compound or a pharmaceutical composition of the present invention. It is expected that after the treatment, the patient's craving for heroine would be suppressed.

Example 31

The patient is suffering from compulsive overeating, obesity or severe obesity. The patient may then be administered an effective amount of a compound or a pharmaceutical composition of the present invention. It is expected that after the treatment, the patient's compulsion to eat would be suppressed.

Example 32

A patient is suffering from pathological gambling. The patient may then be administered an effective amount of a compound or a pharmaceutical composition of the present invention. It is expected that after the treatment, the patient's compulsion to gamble would be suppressed.

Example 33

The patient is suffering from ADD. The patient may then be administered an effective amount of a compound or a pharmaceutical composition of the present invention. It is expected that after the treatment, the patient's symptoms of inattention, impulsivity and/or hyperactivity would be suppressed.

Example 34

A patient is suffering from Tourette's syndrome. The patient may then be administered an effective amount of a compound or a pharmaceutical composition of the present invention. It is expected that after the treatment, the patient's simple, complex, respiratory and vocal tics would be suppressed.

Example 35

A patient is suffering from adenocarcinoma of the prostate. The patient may then be administered an effective amount of a compound or a pharmaceutical composition of the present invention. After this initial treatment, the patient may optionally be administered the same or a different compound of the present invention in intermittent or continuous doses by subdural pump. It is expected that the treatment(s) would prevent recurrences of the adenocarcinoma, or inhibit (i.e., arrest development of) or relieve (i.e., cause regression of) the adenocarcinoma tumor cells.

Example 36

A patient is suffering from adenocarcinoma of the prostate. The patient may then be administered an effective amount of a compound or a pharmaceutical composition of the present invention by direct injection into the tumor. After this initial treatment, the patient may optionally be administered an effective amount of the same or a different compound of the present invention in intermittent or continuous doses by implantation of a biocompatible polymeric matrix delivery system. It is expected that the treatment(s) would prevent recurrences of the adenocarcinoma, or inhibit (i.e., arrest development of) or relieve (i.e., cause regression of) the adenocarcinoma tumor cells.

Example 37

A patient is diagnosed with benign prostatic hyperplasia. The patient may then be administered an effective amount of a compound or a pharmaceutical composition of the present invention by direct injection into the tumor. After this initial treatment, the patient may optionally be administered the same or a different compound of the present invention in intermittent or continuous doses by injection, subdural pump or polymeric matrix implant. It is expected that after the treatment(s), the benign prostatic hyperplastic cells would not develop into carcinoma.

Example 38

A patient is suffering from adenocarcinoma of the prostate. The adenocarcinoma does not appear to have metastasized. The patient undergoes surgery to remove the adenocarcinoma. After post-surgical recovery, the patient may be locally administered an effective amount of a compound or a pharmaceutical composition of the present invention in intermittent or continuous doses by injection, subdural pump or polymeric matrix implant. It is expected that after the treatment, the patient would be protected from recurrences of the adenocarcinoma, and any residual tumorous cells would be inhibited (i.e., arrested in development) or relieved (i.e., caused to regress).

Example 39

A patient is suffering from metastatic adenocarcinoma of the prostate. Although the adenocarcinoma appears to have metastasized, the patient nevertheless undergoes surgery to remove the adenocarcinoma. The patient may then be locally administered an effective amount of a compound or a pharmaceutical composition of the present invention approximately from the time of initial diagnosis through post-surgical recovery. After post-surgical recovery, the patient may continue the same treatment by a regimen of periodic local administration, and carefully monitored for adverse side-effects. It is expected that after the treatments, the patient would be protected from recurrences of the adenocarcinoma, and any residual tumorous cells would be inhibited (i.e., arrested in development) or relieved (i.e., caused to regress).

Example 40

A patient is suffering from cancer as defined herein. An effective amount of a compound or a pharmaceutical composition of the present invention may be administered directly to the cancer cells. After this initial treatment, the patient may be optionally administered an effective amount of the same or a different compound or pharmaceutical composition of the present invention by direct injection, subdural pump or implantation of a biocompatible polymeric matrix delivery system. It is expected that after the treatment(s), the patient would be protected from recurrences of the cancer, and the cancer would be inhibited (i.e., arrested in development) or relieved (i.e., caused to regress).

Example 41

A patient is at risk of injury from a cancerous tumor growth, invasion, or metastasis. The patient may be pretreated with an effective amount of a compound or a pharmaceutical composition of the present invention. It is expected that after the pretreatment, the patient would be protected from any injury due to a cancerous tumor growth, invasion, or metastasis.

Example 42

A patient is suffering from a cancerous tumor growth, invasion, or metastasis. The patient may be administered during or after the inception of the tumor, an effective amount of a compound or a pharmaceutical composition of the present invention. It is expected that after the treatment, the patient would recover or would not suffer any significant injury due to the cancerous tumor growth, invasion, or metastasis.

Example 43

A patient is suffering from a neovascular disease of the eye. A patient may be administered an effective amount of a compound or a pharmaceutical composition of the present invention. It is expected that after the treatment, the patient would recover or would not suffer any significant injury due to the neovascular disease of the eye.

Example 44

A patient is suffering from rheumatoid arthritis. A patient may be administered an effective amount of a compound or a pharmaceutical composition of the present invention. It is expected that after the treatment, the patient would recover or would not suffer any significant injury due to the rheumatoid arthritis.

Example 45

A patient is suffering from peripheral vascular disorder. A patient may be administered an effective amount of a compound or a pharmaceutical composition of the present invention. It is expected that after the treatment, the patient would recover or would not suffer any significant injury due to the peripheral vascular disorder.

Example 46

A patient is suffering from metastatic adenocarcinoma of cancer, as defined herein. Although the adenocarcinoma appears to have metastasized, the patient nevertheless undergoes surgery to remove the adenocarcinoma. The patient may then be locally administered an effective amount of a compound or a pharmaceutical composition of the present invention approximately from the time of initial diagnosis through post-surgical recovery. After post-surgical recovery, the patient may continue the same treatment by a regimen of periodic local administration, and carefully monitored for adverse side-effects. It is expected that after the treatments, the patient would be protected from recurrences of the adenocarcinoma, and any residual tumorous cells would be inhibited (i.e., arrested in development) or relieved (i.e., caused to regress).

Example 47

A female patient wishes to become temporarily infertile, so as not to become pregnant during sexual intercourse. An effective amount of a compound or a pharmaceutical composition of the present invention may then be administered to the patient. It is expected that after the treatment, angiogenesis necessary for fertility would be inhibited and the patient would be protected from pregnancy for the length of time that continued treatments were periodically administered.

Example 48

A patient is suffering from a dermatologic ulcer. A patient may be administered an effective amount of a NAALADase inhibitor or a pharmaceutical composition of the present invention. It is expected that after the treatment, the patient would recover or would not suffer any significant injury due to the dermatologic ulcer.

Example 49

A patient is suffering from a soft tissue wound. A patient may be administered an effective amount of a compound or a pharmaceutical composition of the present invention. It is expected that after the treatment, the patient would recover or would not suffer any significant injury due to the soft tissue wound.

Example 50

A patient is suffering from a cardiovascular disease. A patient may be administered an effective amount of a compound or a pharmaceutical composition of the present invention. It is expected that after the treatment, the patient would recover or would not suffer any significant injury due to the cardiovascular disease.

Example 51

A patient is diagnosed with a disease, disorder or condition as identified in these examples. An effective amount of a compound or a pharmaceutical composition of the present invention may then be administered to the patient intravenously, intramuscularly, intraventricularly to the brain, rectally, subcutaneously, intranasally, through a catheter with or without a pump, orally, through a transdermal patch, topically, or through a polymer implant. After the treatment, the patient's condition would be expected to improve.

Example 52

A patient is diagnosed with a disease, disorder or condition as identified in these examples. A compound or a pharmaceutical composition of the present invention may then be administered to the patient in the form of a 100 mg/kg bolus, optionally followed by a 20 mg/kg per hour intravenous infusion over a two-hour period. After the treatment, the patient's condition would be expected to improve.

The invention being thus described, it will be obvious that the same may be varied in many ways. Such variations are not to be regarded as a departure from the spirit and scope of the invention and all such modifications are intended to be included within the scope of the following claims.

We claim:

1. A compound of formula I

I

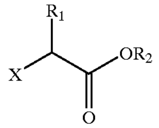

or a pharmaceutically acceptable salt, hydrate, metabolite, or prodrug thereof, wherein:

X is a moiety of formula II

II

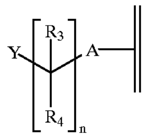

n is 1, 2, 3 or 4;

Y is $SR_5$;

A is $CH_2$;

R, $R_2$, $R_3$, $R_4$, $R_5$, and $R_6$ are indepencicntly hydrogen, $C_1$–$C_9$, straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, (arbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl, or oxy, wherein said alkyl, alkenyl, cycloalkyl, cycloalkenyl and $Ar_1$, are independently unsubstituted or substituted with one or more substituent(s);

$R_1$ is $(CH_2)_2COOR$ or $(CH_2)_2CONHR$; and $Ar_1$ is a carbocyclic or heterocyclic moiety, which is unsubstituted or substituted with one or more substituent(s).

2. The compound of claim 1, wherein $Ar_1$ is selected from the group consisting of phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

3. The compound of claim 1, wherein said one or more substituent(s) of said alkyl, alkenyl, cycloalkyl, cycloalkenyl, and $Ar_1$, are independently selected from the group consisting of $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, oxy, and carbocyclic and heterocyclic moieties.

4. The compound of claim 1, wherein:

A is $CH_2$; and n is 1.

5. The compound of claim 4, wherein:

$R_1$ is $—(CH_2)_2COOR_9$;

$R_9$ is hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_2$, wherein $R_9$ is unsubstituted or substituted with one or more substituent(s); and $Ar_2$ is a carbocyclic or heterocyclic moiety which is unsubstituted or substituted with one or more substituent(s).

6. The compound of claim 5, wherein:

$R_1$ is $(CH_2)_2COOH$; and $R_2$ is hydrogen.

7. The compound of claim 6, which is selected from the group consisting of:

2-(2-sulfanylethyl)pentanedioic acid;

2-(2-sulfanylpropyl)pentanedioic acid;

2-(2-sulfanylbutyl)pentanedioic acid;

2-(2-sulfanylpentyl)pentanedioic acid;

2-(2-sulfanylhexyl)pentanedioic acid;

2-(2-phenyl-2-sulfanylethyl)pentanedioic acid;

2-(2-naphthyl-2-sulfanylethyl)pentanedioic acid;

2-(2-(4-pyridyl)-2-sulfanylethyl)pentanedioic acid;

2-(1-methyl-2-sulfanylethyl)pentanedioic acid;

2-(1-ethyl-2-sulfanylethyl)pentanedioic acid;

2-(1-benzyl-2-sulfanylethyl)pentanedioic acid;

2-(1-methyl-2-sulfanylpropyl)pentanedioic acid;

2-(1-ethyl-2-sulfanylpropyl)pentanedioic acid;

2-(1-propyl-2-sulfanylpropyl)pentanedioic acid;

2-(1-butyl-2-sulfanylpropyl)pentanedioic acid;

2-[2-(methylsulfanyl)-3-phenylpropyl]pentanedioic acid;

2-[2-(ethylsulfanyl)-3-phenylpropyl]pentanedioic acid;

2-[2-(propylsulfanyl)-3-phenylpropyl]pentanedioic acid;

2-[2-(butylsulfanyl)-3-phenylpropyl]pentanedioic acid;

2-[2-(methylsulfanyl)-3-(4-pyridyl)propyl]-pentanedioic acid;

2-(2-(ethylsulfanyl)-3-(4-pyridyl)propyl]-pentanedioic acid;

2-[2-(propylsulfanyl)-3-(4-pyridyl)propyl]-pentanedioic acid;

2-[2-(butylsulfanyl)-3-(4-pyridyl)propyl]-pentanedioic acid; and pharmaceutically acceptable salts, hydrates, metabolites, and prodrugs thereof.

8. The compound of claim 7, which is selected from the group consisting of:

2-(2-sulfanylethyl)pentanedioic acid;

2-(2-sulfanylpropyl)pentanedioic acid;

2-(2-sulfanylbutyl)pentanedioic acid;

2-(2-sulfanylhexyl)pentanedioic acid;

2-(2-phenyl-2-sulfanylethyl)pentanedioic acid;

2-(2-(4-pyridyl)-2-sulfanylethyl)pentanedioic acid;

2-(1-methyl-2-sulfanylpropyl)pentanedioic acid;

2-(1-ethyl-2-sulfanylpropyl)pentanedioic acid;

2-(1-propyl-2-sulfanylpropyl)pentanedioic acid;

2-(1-butyl-2-sulfanylpropyl)pentanedioic acid; and pharmaceutically acceptable salts, hydrates, metabolites, and prodrugs thereof.

9. The compound of claim 1, wherein:

A is $CH_2$; and n is 2, 3 or 4.

10. The compound of claim 9, which is selected from the group consisting of:

2-(3-sulfanylpropyl)pentanedioic acid;

2-(3-sulfanyl-2-methylpropyl)pentanedioic acid;

2-(3-sulfanyl-3-methylpropyl)pentanedioic acid;

2-(3-sulfanyl-3-phenylpropyl)pentanedioic acid;

2-[3-sulfanyl-2-(phenylmethyl)propylpentanedioic acid;

2-(4-sulfanylbutyl)pentanedioic acid;

2-[2-(sulfanylmethyl)butyl]pentanedioic acid;

2-(3-sulfanyl-4-phenylbutyl)pentanedioic acid;

2-[3-sulfanyl-4-(4-pyridinyl) butyl]pentanedioic acid;

2-(4-sulfanyl-2-methylbutyl)pentanedioic acid;

2-(4-sulfanyl-3-methylbutyl)pentanedioic acid;

2-(4-sulfanyl-4-methylbutyl)pentanedioic acid; and 2-(3-sulfanyloctyl)pentanedioic acid.

11. The compound of claim 10, which is selected from the group consisting of:

2-(3-sulfanylpropyl)pentanedioic acid;

2-(3-sulfanyl-2-methylpropyl)pentanedioic acid; and 2-(4-sulfanylbutyl)pentanedioic acid.

12. The compound of claim 1, which is effective for treating stroke in an animal when administered at least 60 minutes following onset of stroke.

13. The compound of claim 11, which is effective for treating stroke in an animal when administered at least 180 minutes following onset of stroke.

14. The compound of claim 12, which is effective for treating stroke in an animal when administered at least 360 minutes following onset of stroke.

15. A pharmaceutical composition comprising:

(i) an effective amount of a compound of claim 1 and (ii) a pharmaceutically acceptable carrier.

16. The pharmaceutical composition of claim 15, wherein the amount of the compound of formula I is effective for inhibiting NAALADase enzyme activity in an animal.

17. The pharmaceutical composition of claim 15, wherein the amount of the compound of formula I is effective for treating a glutamate abnormality in an animal.

18. The pharmaceutical composition of claim 15, wherein the amount of the compound of formula I is effective for effecting a neuronal activity in an animal.

19. The pharmaceutical composition of claim 15, wherein the amount of the compound of formula I is effective for treating a compulsive disorder in an animal.

20. The pharmaceutical composition of claim 15, wherein the amount of the compound of formula I is effective for treating a prostate disease in an animal.

21. The pharmaceutical composition of claim 15, wherein the amount of the compound of formula I is effective for inhibiting angiogenesis in an animal.

22. The pharmaceutical composition of claim 15, wherein $Ar_1$, is selected from the group consisting of phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

23. The pharmaceutical composition of claim 15, wherein said one or more substituent(s) of said alkyl, alkenyl, cycloalkyl, cycloalkenyl and $Ar_1$, are independently selected from the group consisting of $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, oxy, and carbocyclic and heterocyclic moieties.

24. The pharmaceutical composition of claim 15, wherein:

A is $CH_2$; and n is 1.

25. The pharmaceutical composition of claim 24, wherein:

$R_1$ is $—(CH_2)_2COOR_9$;

$R_9$ is hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_2$, wherein $R_9$ is unsubstituted or substituted with one or more substituent(s); and $Ar_2$ is a carbocyclic or heterocyclic moiety which is unsubstituted or substituted with one or more substituent(s).

26. The pharmaceutical composition of claim 25, wherein:

$R_1$ is $(CH_2)_2COOH$; and $R_2$ is hydrogen.

27. The pharmaceutical composition of claim 26, wherein the compound of formula I is selected from the group consisting of:

2-(2-sulfanylethyl)pentanedioic acid;

2-(2-sulfanylpropyl)pentanedioic acid;

2-(2-sulfanylbutyl)pentanedioic acid;

2-(2-sulfanylpentyl)pentanedioic acid;

2-(2-sulfanylhexyl)pentanedioic acid;

2-(2-phenyl-2-sulfanylethyl)pentanedioic acid;

2-(2-naphthyl-2-sulfanylethyl)pentanedioic acid;

2-(2-(4-pyridyl)-2-sulfanylethyl)pentanedioic acid;

2-(1-methyl-2-sulfanylethyl)pentanedioic acid;

2-(1-ethyl-2-sulfanylethyl)pentanedioic acid;

2-(1-benzyl-2-sulfanylethyl)pentanedioic acid;

2-(1-methyl-2-sulfanylpropyl)pentanedioic acid;

2-(1-ethyl-2-sulfanylpropyl)pentanedioic acid;

2-(1-propyl-2-sulfanylpropyl)pentanedioic acid;

2-(1-butyl-2-sulfanylpropyl)pentanedioic acid;

2-[2-(methylsulfanyl)-3-phenylpropyl]pentanedioic acid;

2-[2-(ethylsulfanyl)-3-phenylpropyl]pentanedioic acid;

2-[2-(propylsulfanyl)-3-phenylpropyl]pentanedioic acid;

2-[2-(butylsulfanyl)-3-phenylpropyl]pentanedioic acid;

2-[2-(methylsulfanyl)-3-(4-pyridyl)propyl]-pentanedioic acid;

2-[2-(ethylsultanyl)-3-(4-pyridyl)propyl]-pentanedioic acid;

2-[2-(propylsulfanyl)-3-(4-pyridyl)propyl]-pentanedioic acid;

2-[2-(butylsulfanyl)-3-(4-pyridyl)propyl]-pentanedioic acid; and pharmaceutically acceptable salts, hydrates, metabolites, and prodrugs thereof.

28. The pharmaceutical composition of claim 27, wherein the compound of formula I is selected from the group consisting of:

2-(2-sulfanylethyl)pentanedioic acid;

2-(2-sulfanylpropyl)pentanedioic acid;

2-(2-sulfanylbutyl)pentanedioic acid;

2-(2-sulfanylhexyl)pentanedioic acid;

2-(2-phenyl-2-sulfanylethyl)pentanedioic acid;

2-(2-(4-pyridyl)-2-sulfanylethyl)pentanedioic acid;

2-(1-methyl-2-sulfanylpropyl)pentanedioic acid;

2-(1-ethyl-2-sulfanylpropyl)pentanedioic acid;

2-(1-propyl-2-sulfanylpropyl)pentanedioic acid;

2-(1-butyl-2-sulfanylpropyl)pentanedioic acid; and pharmaceutically acceptable salts, hydrates, metabolites, and prodrugs thereof.

29. The pharmaceutical composition of claim 15, wherein:

A is $CH_2$; and n is 2, 3 or 4.

30. The pharmaceutical composition of claim 29, wherein the compound of formula I is selected from the group consisting of:

2-(3-sulfanylpropyl)pentanedioic acid;

2-(3-sulfanyl-2-methylpropyl)pentanedioic acid;

2-(3-sulfanyl-3-methylpropyl)pentanedioic acid;

2-(4-sulfanylbutyl)pentanedioic acid;

2-(4-sulfanyl-2-methylbutyl)pentanedioic acid;

2-(4-sulfanyl-3-methylbutyl)pentanedioic acid; and 2-(4-sulfanyl-4-methylbutyl)pentanedioic acid.

31. The pharmaceutical composition of claim 30, wherein the compound of formula I is selected from the group consisting of:

2-(3-sulfanylpropyl)pentanedioic acid;

2-(3-sulfanyl-2-methylpropyl)pentanedioic acid; and 2-(4-sulfanylbutyl)pentanedioic acid.

32. The pharmaceutical composition of claim 17, wherein the glutamate abnormality is stroke.

33. The pharmaceutical composition of claim 32, comprising the compound of formula I in an effective amount for treating stroke in an animal when administered at least 60 minutes following onset of stroke.

34. The pharmaceutical composition of claim 32, comprising the compound of formula I in an effective amount for treating stroke in an animal when administered at least 180 minutes following onset of stroke.

35. The pharmaceutical composition of claim 32, comprising the compound of formula I in an effective amount for treating stroke in an animal when administered at least 360 minutes following onset of stroke.

* * * * *